(12) United States Patent
Kukolj et al.

(10) Patent No.: US 7,294,457 B2
(45) Date of Patent: Nov. 13, 2007

(54) DIRECT BINDING ASSAY FOR IDENTIFYING INHIBITORS OF HCV POLYMERASE

(75) Inventors: George Kukolj, Mont-Royal (CA); Pierre Louis Beaulieu, Rosemère (CA); Ginette McKercher, Montreal (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 829 days.

(21) Appl. No.: 10/211,455

(22) Filed: Aug. 2, 2002

(65) Prior Publication Data
US 2003/0108862 A1 Jun. 12, 2003

Related U.S. Application Data

(60) Provisional application No. 60/310,272, filed on Aug. 7, 2001.

(51) Int. Cl.
*C12Q 1/70* (2006.01)
*G01N 33/53* (2006.01)
*A01N 43/50* (2006.01)

(52) U.S. Cl. .......................... 435/5; 435/7.1; 514/396

(58) Field of Classification Search ................ 435/5, 435/7.1; 514/396
See application file for complete search history.

(56) References Cited

U.S. PATENT DOCUMENTS 6,770,666 B2 * 8/2004 Hashimoto et al. ......... 514/394

FOREIGN PATENT DOCUMENTS

| WO | WO 01 47883 A | 7/2001 |
|----|---------------|--------|
| WO | WO 02 04425 A | 1/2002 |
| WO | WO 02 070739 A | 9/2002 |
| WO | WO 03 007945 A | 1/2003 |
| WO | WO 03 010140 A | 2/2003 |
| WO | WO 03 010141 A | 2/2003 |

OTHER PUBLICATIONS

McKercher et al., Specific inhibitors of HCV polymerase identified using an NS5B with lower affinity for template/primer substrate, Nucleic Acids Research, 2004, vol. 32, No. 2, pp. 422-431.*
Hijkata, Makoto et al; Gene mapping of the putative structural region of the hepatitis C virus genome by in Vitro processing analysis; PNAS; 1991, V. 88; 5547-5551.
Grakoui Abash et al.; Expression and Identification of Hepatitis C Virus Polyprotein Cleavage Products; J. Virol.;1993, V. 67, No. 3;1385-1395.
Grakoui, Abash et al.; A second hepatitis C virus-encoded proteinase; PNAS; 1993, V.90; 10583-10587.
Hijkata, Makoto et al.; Two Distinct Proteinase Activities Required for the Processing of a Putative Nonstructural Precursor Protein of Hepatitis C Virus; J. Virol.;1993; V. 67, No. 8; 4665-4675.

Kim, J.-E. et al.; Subcellular localization of hepatitis C viral proteins in mammalian cells; Arch. Virol.;1999; V. 144; 329-343.
Bartenschlager, Ralf et al.: Nonstructural Protein 3 of the Hepatitis C Virus Encodes a Serine-Type Proteinase Required for Cleavage at the NS3/4 and NS4/5 Junctions; J. Virol.; 1993; V. 67 No. 7; 3835-3844.

(Continued)

*Primary Examiner*—Mark L. Shibuya
(74) *Attorney, Agent, or Firm*—Michael Morris; Mary-Ellen M. Devlin; David Dow

(57) ABSTRACT

A method for identifying compounds binding to HCV polymerase comprising the steps of: contacting said HCV polymerase or an analog thereof with a probe formula I:

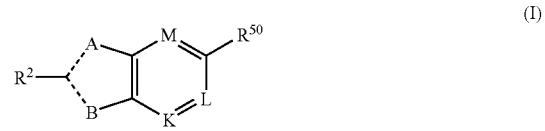

wherein A is O, S, N, $NR^1$, or $CR^1$, wherein $R^1$ is defined herein;
----- represents either a single or a double bond;
$R^2$ is selected from: H, halogen, $R^{21}$, $OR^{21}$, $SR^{21}$, $COOR^{21}$, $SO_2N(R^{22})_2$, $N(R^{22})_2$, $CON(R^{22})_2$, $NR^{22}C(O)R^{22}$ or $NR^{22}C(O)NR^{22}$ wherein $R^{21}$ and each $R^{22}$ is defined herein;
B is $NR^3$ or $CR^3$, wherein $R^3$ is defined herein;
with the proviso that, when A is not N, then one of A or B is either $CR^1$ or $CR^3$,
K is N or $CR^4$, wherein $R^4$ is defined herein;
L is N or $CR^5$, wherein $R^5$ has the same definition as $R^4$ defined above;
M is N or $CR^7$, wherein $R^7$ has the same definition as $R^4$ defined above;
$R^5$ is $C(Y^1)Z$ wherein $Y^1$ is O or S; and
Z is $N(R^{6a})R^6$ or $OR^6$, wherein $R^{6a}$ is H or alkyl or $NR^{61}R^{62}$ wherein $R^{61}$ and $R^{62}$ are defined herein; and $R^6$ is H, alkyl, cycloalkyl, alkenyl, Het, alkyl-aryl, alkyl-Het; or $R^6$ is

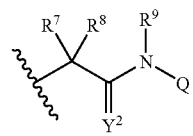

wherein $R^7$ and $R^8$ and Q are as defined herein;
$Y^2$ is O or S;
$R^9$ is H, $(C_{1-6}$ alkyl), $(C_{3-7})$cycloalkyl or $(C_{1-6})$alkyl-$(C_{3-7})$cycloalkyl, aryl, Het, $(C_{1-6})$alkyl-aryl or $(C_{1-6})$alkyl-Het, all of which optionally substituted with $R^{90}$; or $R^9$ is covalently bonded to either of $R^7$ or $R^8$ to form a 5- or 6-membered heterocycle; or a salt thereof; where the probe comprises a detectable label attached to any suitable position, whereby said probe binds to an HCV polymerase or an analog thereof and is capable of being displaced by an inhibitor thereof.

16 Claims, 7 Drawing Sheets

OTHER PUBLICATIONS

Love, Robert A. et al.; The Crystal Structure of Hepatitis C Virus NS3 Proteinase Reveals a Trypsin-like Fold and a Structural Zinc Binding Site; Cell; 1996; V. 87; 331-342.

Kwong, Ann D. et al.; Hepatitus C virus NS3/4A protease; Antiviral Res.; 1998; V. 40; 1-18.

Kim, Dong Wook et al.; C-Terminal Domain of the Hepatitis C Virus NS3 Protein Contains an RNA Helicase Activity; Biochem. Biophys. Res. Comm.; 1995; V. 215, No. 1; 160-165.

Gale, Michael J. Jr. et al.; Evidence That Hepatitis C Virus Resistance to Interferon is Mediated through Repression of the PKR Protein Kinase by the Nonstructural 5A Protein; Virol.; 1997; V. 230; 217-227.

Reed, Karen E. et al.; Phosphorylation of the Hepatitis C Virus NS5A Protein In Vitro and In Vivo: Properties of the NS5A-Associated Kinase; J. Virol.; 1997; V.71, No. 10; 7187-7197.

Lesburg, Charles A. et al.; Crystal structure of the RNA-dependent RNA polymerase from hepatitis C virus reveals a fully encircled active site; Nature Struct. Biol.; 1999, V. 6, No. 10; 937-943.

Zhong, Weidong et al.; Template/Primer Requirements and Single Nucleotide Incorporation by Hepatitis C Virus Nonstructural Protein 5B Polymerase; J. Virol.; 2000; V. 74, No. 19; 9134-9143.

Yamashita, Tatsuya et al.; RNA-dependent RNA Polymerase Activity of the Soluble Recombinant Hepatitis C Virus NS5B Protein Truncated at the C-Terminal Region; J. Biol. Chem.; 1998; V. 273, No. 25; 15479-15486.

Ferrari, Eric et al.; Characterization of Soluble Hepatitis C Virus RNA-Dependent RNA Polymerase Expressed in *Escherichia coli*; J. Virol.;1999; V. 73, No. 2; 1649-1654.

Zhang, Ji-Hu et al.; A Simple Statistical Parameter for Use in Evaluation and Validation of High Throughput Screening Assays; J. Biomol. Screen.; 1999; V. 4, No. 2; 67-73.

Simons, John N, et al.; Indentification of two flavivirus-like genomes in the GB hepatitis agent; PNAS; 1995; V. 92; 3401-3405.

Bukh, Jens et al.; Toward a Surrogate Model for Hepatitis C Virus: An Infectious Molecular Clone of the GB Virus-B Hepatitis Agent; Virology; 1999; V. 262; 470-478.

Yanagi, Masayuki et al.; Transcripts from a single full-length cDNA clone of hepatitis C virus are infectious when directly transfected into the liver of a chimpanzee; 1997; PNAS; V. 94; 8738-8743.

Carroll, Steven S. et al.; Only a Small Fraction of Purified Hepatitis C RNA-Dependent RNA Polymerase is Catalytically Competent: Implications for Viral Replication and in Vitro Assays; Biochemistry; 2000; V. 39; 8243-8249.

Tomei, Licia et al.; Biochemical characterization of a hepatitis C virus RNA-dependent RNA polymerase mutant lacking the C-terminal hydrophobic sequence; J. Gen. Virol.; 2000; V. 81; 759-767.

Behrens, Sven-Erik et al.; Indentification and properties of the RNA-dependent RNA polymerase of hepatitis C virus; The EMBO Journal; 1996; V. 15 No. 1;12-22.

De Francesco, Raffaele et al.; RNA-Dependent RNA Polymerase: of Hepatitis C Virus; Methods Enzymology;1996; V. 275; 58-67.

Lohmann, Volker et al.; Biochemical Properties of Hepatitis C Virus NS5B RNA-Dependent RNA Polymerase and Identification of Amino Acid Sequence Motifs Essential for Enzymatic Activity; J. Virol.;1997; V. 71; No. 11; 8416-8428.

Lohmann, Volker et al.; Biochemical and Kinetic Analyses of NS5B RNA-Dependent RNA Polymerase of the Hepatitis C Virus; J. Virology; 1998; V. 249; 108-118.

Yuan Z-H et al.; Expression, Purification, and Partial Characterization of HCV RNA Polymerase; 1997; V. 232; 231-235.

Luo, Guangxiang et al.; De Novo Initiation of RNA Synthesis by the RNA-Dependent RNA Polymerase (NS5B) of Hepatitis C Virus; J. Virology; 2000; V. 74, No. 2; 851-863.

Oh, Jong-Won et al.; A Recombinant Hepatitis C Virus RNA-Dependent RNA Polymerase Capable of Copying the Full-Length Viral RNA; J. Virol.; 1999, V. 73, No. 9; 7694-7702.

Sun, Xin-Lai et al.; De Novo RNA Synthesis Catalyzed by HCV RNA-Dependent RNA Polymerase; Biochem. Biophys. Res. Commun.; 2000, V. 268; 798-803.

Zhong, Weidong et al.; De Novo Initiation of RNA Synthesis by Hepatitis C Virus Nonstructural Protein 5B Polymerase; J. Virol.; 2000; V. 74, No. 4; 2017-2022.

Bressanelli, Stephane et al.; Crystal structure of the RNA-dependent RNA polymerase of hepatitis C virus; PNAS; 1999; V. 96, No. 23;13034-13039.

Ago, Hideo et al.; Crystal structure of the RNA-dependent RNA polymerase of hepatitis C virus; Structure; 1999; V. 7; No. 11;1417-1426.

* cited by examiner

Titration of Probe with HCV NS5B Polymerase d21—His
*Fluorescence Anisotropy Analysis*

Kd = 1.26E−08   rf = 6.01E−02   rb = 2.55E−01   Qb/Qf = 0.78   Bkg = 0

Z' value in the Polarization assay

A.

Kd for compound A with His-NS5Bd21

| Variable | Value | Std. Err. |
|---|---|---|
| Kd of inhibitor | 3.0971e-008 | 5.5429e-009 |
| Qb/Qf | 6.6898e-001 | 6.1946e-002 |

B.

Kd for compound B with His-NS5Bd21

| Variable | Value | Std. Err. |
|---|---|---|
| Kd of inhibitor | 4.1498e-008 | 8.1777e-009 |
| Qb/Qf | 7.1835e-001 | 8.0672e-002 |

A.

Kd for compound C with NS5Bd21-His

| Variable | Value | Std. Err. |
|---|---|---|
| Kd of inhibitor | 2.3067e-007 | 5.8224e-008 |
| Qb/Qf | 7.4124e-001 | 9.1773e-002 |

B.

Kd for compound D with NS5Bd21-His

| Variable | Value | Std. Err. |
|---|---|---|
| Kd of inhibitor | 1.0824e-006 | 2.3258e-007 |
| Qb/Qf | 6.5635e-001 | 8.2954e-002 |

Titration of probe i with NS5Bd21-His polymerase in Tris pH 7.5 and 30 mM NaCl
*Fluorescence Anisotropy Analysis*

Kd = 1.53E−08   rf = 7.86E−02   rb = 3.23E−01   Qb/Qf = 0.68   Bkg = 0

Titration of probe i with NS5Bd21-His polymerase in Tris pH 7.5 and 100 mM NaCl
*Fluorescence Anisotropy Analysis*

Kd = 3.89E−08   rf = 8.79E−02   rb = 2.96E−01   Qb/Qf = 0.7   Bkg = 0

Titration of probe i with NS5Bd21-His polymerase in Tris pH 7.5 and 150 mM NaCl
*Fluorescence Anisotropy Analysis*

Kd = 7.83E−08   rf = 8.91E−02   rb = 2.91E−01   Qb/Qf = 0.7   Bkg = 0

Titration of probe i with NS5Bd21-His polymerase in Tris pH 7.5 and 200 mM NaCl
*Fluorescence Anisotropy Analysis*

Kd = 1.22E−07   rf = 8.51E−02   rb = 2.96E−01   Qb/Qf = 0.73   Bkg = 0

Titration of probe i with NS5Bd21-His polymerase in Phosphate buffer pH 6.5
*Fluorescence Anisotropy Analysis*

Kd = 3.33E−08   rf = 8.55E−02   rb = 2.88E−01   Qb/Qf = 0.974   Bkg = 0

Titration of probe i with His-NS5Bd21
*Fluorescence Anisotropy Analysis*

Kd = 1.81E−08   rf = 4.44E−02   rb = 2.64E−01   Qb/Qf = 0.7   Bkg = 0

FIGURE 11

Titration of probe ii with GBV-B polymerase

[GBV-BΔ23-His] (M)

*Fluorescence Anisotropy Analysis*

Kd = 1.79E−06    rf = 9.03E−02    rb = 2.14E−01    Qb/Qf = 1.29    Bkg = 0

FIGURE 12

Titration of probe ii with His-NS5BΔ21 (H77c,1a) polymerase

[His-NS5BΔ21(H77c,1a)] (M)

*Fluorescence Anisotropy Analysis*

Kd = 1.82E−08    rf = 9.22E−02    rb = 2.97E−01    Qb/Qf = 1.18    Bkg = 0

DIRECT BINDING ASSAY FOR IDENTIFYING INHIBITORS OF HCV POLYMERASE

RELATED APPLICATIONS

Benefit of U.S. Provisional Application Ser. No. 60/310,272 filed Aug. 7, 2001, is hereby claimed and said application is incorporated by reference in its entirety.

FIELD OF THE INVENTION

The present invention relates generally to a method for identifying inhibitors of the HCV RNA dependent RNA polymerase. Particularly, this method uses a novel probe in a competitive assay to identify HCV polymerase inhibitors and determine their potency. More particularly, this invention relates to the use of a probe which binds with specificity to the polymerase, and which is capable of being displaced by inhibitors of the enzyme.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system.

HCV is an enveloped positive strand RNA virus in the Flaviviridae family. The single strand HCV RNA genome is of positive polarity and comprises one open reading frame (ORF) of approximately 9600 nucleotides in length, which encodes a linear polyprotein of approx. 3010 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle (Hijikata, M. et al., 1991, Proc. Natl. Acad. Sci. USA. 88, 5547-5551; Grakoui, A. et al., 1993(a), J. Virol. 67,1385-1395). The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases (Hijikata et al., 1991, supra). The generation of the mature non-structural proteins is catalyzed by two virally encoded proteases. The first is the NS2/3 zinc-dependent metalloprotease which auto-catalyses the release of the NS3 protein from the polyprotein. The released NS3 contains a N-terminal serine protease domain (Grakoui A, et al., 1993(b), Proc Natl Acad Sci USA, 90, 10583-7; Hijikata, M. et al., 1993, J. Virol. 67, 4665-4675.) and catalyzes the remaining cleavages from the polyprotein. The released NS4A protein has at least two roles. First, forming a stable complex with NS3 protein and assisting in the membrane localization of the NS3/NS4A complex (Kim et al., Arch Virol. 1999, 144: 329-343) and second, acting as a cofactor for NS3 protease activity. This membrane-associated complex, in turn catalyzes the cleavage of the remaining sites on the polyprotein, thus effecting the release of NS4B, NS5A and NS5B (Bartenschlager, R. et al., 1993, J. Virol., 67, 3835-3844; Grakoui et al., 1993(a) supra; Hijikata et al., 1993 supra; Love, R. A. et al., 1996, Cell, 87, 331-342; reviewed in Kwong AD. et al., 1998, Antiviral Res., 40, 1-18). The C-terminal segment of the NS3 protein also harbors nucleoside triphosphatase and RNA helicase activity (Kim, D. W. et al., 1995, Biochem. Biophys. Res. Comm., 215,160-166). The function of the protein NS4B is unknown. NS5A, a highly phosphorylated protein, seems to be responsible for the Interferon resistance of various HCV genotypes (Gale Jr. et al. 1997 Virology 230, 217; Reed et al., 1997, J. Virol. 71, 7187). NS5B is an RNA-dependent RNA polymerase (RdRp) that is involved in the replication of HCV.

To better understand the mechanism of HCV RNA replication and to develop appropriate in vitro systems, biochemical analyses of the NS5B protein have been performed. Full-length NS5B has been produced and purified as a non-fusion protein from insect cells infected with recombinant baculovirus (S. -E. Behrens et al., 1996, EMBO J., 15:12-22; R. de Francesco et al, 1996, Methods Enzymol., 275:58-67) or as a tagged protein from both insect cells (V. Lohmann et al., 1997, J. Virol., 71:8416-8428; V. Lohmann et al., 1998, Virology 249:108-118) and E. coli (Z. -H. Yuan et al, 1997, BBRC 232:231-235). In vitro, the RdRp activity of recombinant NS5B is dependent on an RNA template and requires RNA or DNA as a primer (S. -E. Behrens et al, 1996, EMBO J. 15:12-22; V. Lohmann et al., 1997, J. Virol., 71:8416-8428). On RNA templates of heteropolymeric sequences, the 3'-OH of the template is used as a primer and elongation proceeds via a "snap-back" mechanism, leading to a double-stranded molecule in which template and product RNA are covalently linked (S. -E. Behrens et a., 1996, EMBO J., 15:12-22; V. Lohman et al., 1998, Virology, 249:108-118; G. Luo et al., 2000, J. Virol. 74:851-863). Recently, several groups also demonstrated that the HCV NS5B protein is able to initiate RNA synthesis de novo (J. Oh et al, 1999, J. Virol. 73:7694-7702; X. Sun et al., 2000, BBRC 268:798-803; W. Zhong et al., 2000, J. Virol. 74:2017-2022).

The NS5B RdRp has been crystallized to reveal a structure reminiscent of other nucleic acid polymerases (S. Bressanelli et al., 1999, PNAS USA 96:13034-13039; H. Ago et al., 1999, Structure 7:1417-1426; C. A. Lesburg et al, 1999, Nature Struct. Biol., 6:937-943). A comprehensive understanding of the differences between HCV and cellular polymerases will facilitate the design of specific inhibitors of HCV replication. Detailed kinetic information will also help in understanding the molecular basis of HCV NS5B-catalyzed nucleotide incorporation and subsequently the mechanistic characterization of the inhibitors.

Previous studies (S. -E. Behrens et a., 1996, EMBO J. 15:12-22; R. de Francesco et al., 1996, Methods Enzymol. 275:58-67; V. Lohmann et al., 1997, J. Virol. 71:8416-8428; V. Lohmann et al., 1998, Virology 249:108-118) provided little information with regard to the proportion of the polymerase RNA complexes that are competent for catalysis. Some recent studies investigated the template and primer requirements for HCV NS5B-directed RNA replication. Templates with 3'-termini free of secondary structures and short primers 2 or 3 nucleotides (nt) long were preferred for efficient initiation of RNA synthesis (W. Zhong et a., 2000, J. Virol. 74:9134-9143). In de novo initiation of RNA synthesis, however, NS5B needs a template with a stable secondary structure and a single-stranded sequence that contains at least one 3'-cytidylate.

Viral polymerases represent attractive targets for therapeutic inhibition of viral replication. The discovery of new antiviral agents often involves screening of large numbers of samples for inhibition of the target activity using either in vitro or in vivo assays. In general, polymerases are assayed by monitoring the incorporation of either $^3$H—, $\alpha$-$^{32}$P or $\alpha$-$^{33}$P-labeled mononucleotides into oligonucleotide products, or by the extension of 5'-end-labeled primers. Products incorporated into the extended primers are captured or separated using common filter assays, acid precipitation, or denaturing gel electrophoresis.

The HCV NS5B polymerase is a prime target in the search for inhibitors of HCV replication. Different preparations of the HCV polymerase exhibit varying efficiencies of product formation with a variety of RNA substrates. Moreover, the activity of purified recombinant NS5B polymerase varies significantly with specific RNA substrates. In addition, the in vitro RNA polymerase activity of NS5B is extremely sensitive to ionic strength, and salt concentrations exceeding 100 mM inhibit the reaction. Hence the ability to determine the potency of inhibitors at various salt concentrations is restricted by this limitation of standard enzymatic reactions. Also, HCV polymerase enzymatic assays disclosed in the prior art provide $IC_{50}$ values as representative measurements of inhibitor potencies. For inhibitors that are competitive with either RNA or NTP, the $IC_{50}$ value is proportional to the concentration of substrates in the assay and will vary depending on the concentration of these components.

In an effort to overcome the limitations of HCV polymerase assays that use sub-optimal and poorly characterized RNA substrates, the Applicants have developed an assay for identifying specific inhibitors of the HCV polymerase that is independent of RNA.

It is therefore an advantage of the present invention to provide an assay that permits a direct measurement of inhibitor potencies (reflected by $K_d$ values as an unequivocal determination of inhibitor potency) under defined conditions, irrespective of the substrate concentration.

The direct binding assay of this invention is amenable to adjustments in salt concentration or pH levels beyond the restricted range required for RNA polymerization. This type of assay is amenable to a high sensitivity and a high throughput format.

It is a further advantage of the present invention to provide a probe that binds to the polymerase with a high affinity, and which is displaced by inhibitors of the enzyme.

It is a further advantage to provide an assay that is applicable to HCV polymerases of different genotypes.

SUMMARY OF THE INVENTION

In a first aspect of the invention, there is provided a method for identifying compounds binding to HCV polymerase comprising the steps of:
a) contacting an HCV polymerase or an analog thereof with a probe being capable of binding to an HCV polymerase or an analog thereof, said probe being displaceable by an inhibitor thereof, so as to form a complex comprising said probe bound to said polymerase;
b) measuring a signal emitted from said probe in said complex to establish a base line level;
c) incubating the product of step a) with a test compound; and
d) measuring the signal from said complex; and
e) comparing the signal from step d) with the signal from step b);

whereby a modulation in said signal is an indication that said test compound binds to said polymerase.

In a preferred aspect of the first embodiment, the probe is selected from: an isomer, enantiomer, diastereoisomer, or tautomer of a probe represented by formula I:

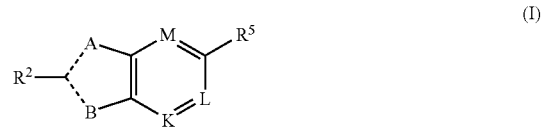

(I)

wherein:
A is O, S, N, NR$^1$, or CR$^1$, wherein R$^1$ is selected from the group consisting of: H, (C$_{1-6}$)alkyl optionally substituted with:
halogen, OR$^{11}$, SR$^{11}$ or N(R$^{12}$)$_2$, wherein R$^{11}$ and each R$^{12}$ is independently H, (C$_{1-6}$)alkyl, (C$_{3-7}$)cycloalkyl, (C$_{1-6}$)alkyl-(C$_{3-7}$)cycloalkyl, (C$_{1-6}$)alkyl-aryl or (C$_{1-6}$) alkyl-Het, said aryl or Het optionally substituted with R$^{10}$; or
both R$^{12}$ are covalently bonded together and to the nitrogen to which they are both attached to form a 5, 6 or 7-membered saturated heterocycle;
----- represents either a single or a double bond;
R$^2$ is selected from: H, halogen, R$^{21}$, OR$^{21}$, SR$^{21}$, COOR$^{21}$, SO$_2$N(R$^{22}$)$_2$, N(R$^{22}$)$_2$, CON(R$^{22}$)$_2$, NR$^{22}$C(O)R$^{22}$ or NR$^{22}$C(O)NR$^{22}$ wherein R$^{21}$ and each R$^{22}$ is independently H, (C$_{1-6}$)alkyl, haloalkyl, (C$_{2-6}$)alkenyl, (C$_{3-7}$)cycloalkyl, (C$_{2-6}$)alkynyl, (C$_{5-7}$)cycloalkenyl, 6 or 10-membered aryl or Het, said R$^{21}$ and R$^{22}$ being optionally substituted with R$^{20}$;
or both R$^{22}$ are bonded together to form a 5, 6 or 7-membered saturated heterocycle with the nitrogen to which they are attached;
B is NR$^3$ or CR$^3$, wherein R$^3$ is selected from (C$_{1-6}$)alkyl, haloalkyl, (C$_{3-7}$)cycloalkyl,
(C$_{6-10}$)bicycloalkyl, 6- or 10-membered aryl, Het, (C$_{1-6}$) alkyl-aryl or (C$_{1-6}$)alkyl-Het, said alkyl, cycloalkyl, bicycloalkyl, aryl, Het, alkyl-aryl and alkyl-Het being optionally substituted with from 1 to 4 substituents selected from: halogen, or
a) (C$_{1-6}$)alkyl optionally substituted with:
—OR$^{31}$ or SR$^{31}$ wherein R$^{31}$ is H, (C$_{1-6}$alkyl), (C$_{3-7}$) cycloalkyl, (C$_{1-6}$)alkyl-(C$_{3-7}$)cycloalkyl, aryl, Het, (C$_{1-6}$)alkyl-aryl or (C$_{1-6}$) alkyl-Het; or
—N(R$^{32}$)$_2$ wherein each R$^{32}$ is independently H, (C$_{1-6}$)alkyl, (C$_{3-7}$)cycloalkyl, (C$_{1-6}$)alkyl-(C$_{3-7}$) cycloalkyl, aryl, Het, (C$_{1-6}$)alkyl-aryl or (C$_{1-6}$) alkyl-Het; or both R$^{32}$ are covalently bonded together and to the nitrogen to which they are attached to form a 5, 6 or 7-membered saturated heterocycle;
b) OR$^{33}$ wherein R$^{33}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$) alkyl-aryl or (C$_{1-6}$)alkyl-Het;
c) SR$^{34}$ wherein R$^{34}$ is H, (C$_{1-6}$)alkyl, (C$_{3-7}$)cycloalkyl, or (C$_{1-6}$)alkyl-(C$_{3-7}$)cycloalkyl, aryl, Het, (C$_{1-6}$) alkyl-aryl or (C$_{1-6}$)alkyl-Het; and
d) N(R$^{35}$)$_2$ wherein each R$^{35}$ is independently H, (C$_{1-6}$) alkyl, (C$_{3-7}$)cycloalkyl, (C$_{1-6}$)alkyl-(C$_{3-7}$)cycloalkyl, aryl, Het, (C$_{1-6}$)alkyl-aryl or (C$_{1-6}$)alkyl-Het; or both R$^{35}$ are covalently bonded together and to the nitrogen to which they are attached to form a 5, 6 or 7-membered saturated heterocycle;

with the proviso that, when A is not N, then one of A or B is either $CR^1$ or $CR^3$;

K is N or $CR^4$, wherein $R^4$ is H, halogen, $(C_{1-6})$alkyl, haloalkyl, $(C_{3-7})$cycloalkyl or $(C_{1-6})$alkyl-$(C_{3-7})$cycloalkyl; or $R^4$ is $OR^{41}$ or $SR^4$, $COR^{41}$ or $NR^4 COR^{41}$ wherein each $R^{41}$ is independently H, $(C_{1-6})$alkyl), $(C_{3-7})$cycloalkyl or $(C_{1-6})$alkyl-$(C_{3-7})$cycloalkyl; or $R^4$ is $NR^{42}R^{43}$ wherein $R^{42}$ and $R^{43}$ are each independently H, $(C_{1-6})$alkyl, $(C_{3-7})$cycloalkyl, $(C_{1-6})$alkyl-$(C_{3-7})$cycloalkyl, or both $R^{42}$ and $R^{43}$ are covalently bonded together and to the nitrogen to which they are attached to form a 5, 6 or 7-membered saturated heterocycle;

L is N or $CR^5$, wherein $R^5$ has the same definition as $R^4$ defined above;

M is N or $CR^7$, wherein $R^7$ has the same definition as $R^4$ defined above;

$R^5$ is $C(Y^1)$-Z wherein $Y^1$ is O or S;

Z is $N(R^{6a})R^6$ or $OR^6$, wherein $R^{6a}$ is H or $(C_{1-6})$alkyl or $NR^{61}R^{62}$ wherein $R^{61}$ and $R^{62}$ are each independently H, $(C_{1-6})$alkyl, $(C_{3-7})$cycloalkyl, $(C_{1-6})$alkyl-$(C_{3-7})$cycloalkyl, or both $R^{61}$ and $R^{62}$ are covalently bonded together and to the nitrogen to which they are both attached to form a 5, 6 or 7-membered saturated heterocycle; or $R^{62}$ is $COOR^{63}$ wherein $R^{63}$ is $(C_{1-6})$alkyl, $(C_{3-6})$cycloalkyl, said alkyl or cycloalkyl being optionally substituted with 6- or 10-membered aryl or Het; or $R^{62}$ is $COR^{64}$ wherein $R^{64}$ is $C_{1-6}$alkyl, $(C_{3-6})$cycloalkyl -6-or 10-membered aryl or Het; and $R^6$ is selected from the group consisting of: H, $(C_{1-6})$alkyl, $(C_{3-6})$cycloalkyl, $(C_{2-6})$alkenyl, 6- or 10-membered aryl, Het, $(C_{1-6})$alkyl-aryl, $(C_{1-6})$alkyl-Het, wherein said alkyl, cycloalkyl, alkenyl, aryl, Het, alkyl-aryl, or alkyl-Het, are all optionally substituted with $R^{60}$ ;

or $R^6$ is

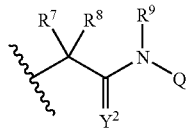

wherein $R^1$ and $R^8$ are each independently H, $(C_{1-6})$alkyl, haloalkyl, $(C_{3-7})$cycloalkyl, 6- or 10-membered aryl, Het, $(C_{1-6})$alkyl-aryl, $(C_{1-6})$alkyl-Het, wherein said alkyl, cycloalkyl, aryl, Het, $(C_{1-6})$alkyl-aryl, $(C_{1-6})$alkyl-Het are optionally substituted with $R^{70}$; or $R^7$ and $R^8$ are covalently bonded together to form second $(C_{3-7})$cycloalkyl or a 4, 5- or 6-membered heterocycle having from 1 to 4 heteroatom selected from O, N, and S; or when Z is $N(R^{6a})R^6$, either of $R^7$ or $R^8$ is covalently bonded to $R^{6a}$ to form a nitrogen-containing 5-or 6-membered heterocycle;

$Y^2$ is O or S;

$R^9$ is H, $(C_{1-6})$alkyl), $(C_{3-7})$cycloalkyl or $(C_{1-6})$alkyl-$(C_{3-7})$cycloalkyl, aryl, Het, $(C_{1-6})$alkyl-aryl or $(C_{1-6})$alkyl-Het, all of which optionally substituted with $R^{90}$; or $R^9$ is covalently bonded to either of $R^7$ or $R^8$ to form a 5- or 6-membered heterocycle;

Q is a 6- or 10-membered aryl, Het, $(C_{1-6})$alkyl-CONH-aryl or $(C_{1-6})$alkyl-CONH-Het, all of which being optionally substituted with:

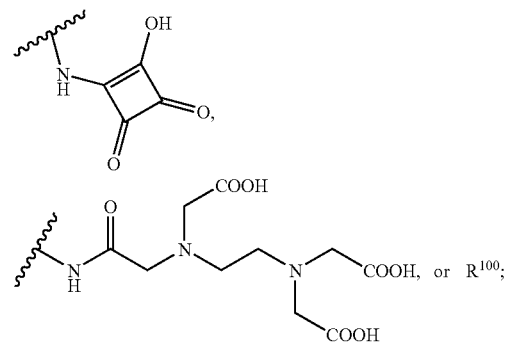

or a salt or a derivative thereof;

wherein Het is defined as 5- or 6-membered heterocycle having 1 to 4 heteroatoms selected from O, N, and S, or a 9- or 10-membered heterobicycle having 1 to 4 heteroatoms selected from O, N and S; and $R^{10}$, $R^{20}$ $R^{60}$, $R^{70}$, $R^{90}$ and $R^{100}$ is each defined as:

1 to 4 substituents selected from: halogen, $OPO_3H$, $NO_2$, cyano, azido, $C(=NH)NH_2$, $C(=NH)NH(C_{1-6})$alkyl or $C(=NH)NHCO(C_{1-6})$alkyl; or 1 to 4 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{150}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SR^{108}$, $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which are attached to form a 5, 6 or 7-membered saturated heterocycle, said alkyl, cycloalkyl, aryl, Het, $(C_{1-6}$alkyl)aryl or $(C_{1-6}$alkyl) Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$; and wherein $R^{150}$ is defined as: —1 to 3 substituents selected from: halogen, $OPO_3H$, $NO_2$, cyano, azido, $C(=NH)NH_2$, $C(=NH)NH(C_{1-6})$alkyl or $C(=NH)NHCO(C_{1-16})$alkyl; or 1 to 3 substituents selected from:
a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{160}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

d) $SR^{108}$, $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{160}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{115}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$ cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{160}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{160}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{160}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{160}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{160}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{160}$;

j) tetrazole, $COOR^{128}$ wherein $R^{128}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said ($C_{1-6}$) alkyl, ($C_{3-7}$)cycloalkyl, or ($C_{1-6}$)alkyl-($C_{3-7}$)cycloalkyl, aryl, Het, ($C_{1-6}$alkyl)aryl and ($C_{1-6}$alkyl)Het being optionally substituted with $R^{160}$; and k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SR^{161}$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, ($C_{1-6}$)alkyl, ($C_{3-7}$)cycloalkyl or ($C_{1-6}$)alkyl-($C_{3-7}$)cycloalkyl; or both $R^{162}$ are covalently bonded together and to the nitrogen to which they are attached to form a 5, 6 or 7-membered saturated heterocycle, wherein said probe comprises a detectable label attached to any suitable position, whereby said probe binds to an HCV polymerase or an analog thereof and is capable of being displaced by an inhibitor thereof.

According to an alternative of this first embodiment, the probe used for the assay does not comprise a detectable label, and the signal measured is the change in intrinsic fluorescence of the HCV polymerase in the presence and absence of said probe.

According to a second aspect of the invention, there is provided the use of a probe according to formula I in the development of an assay for identifying inhibitors of HCV polymerase.

According to a third aspect of the invention, there is provided a kit for testing compounds potentially binding to HCV polymerase, said kit comprising the probe of formula (I) and instructions on how to use said probe for identifying test compounds binding to said polymerase.

BRIEF DESCRIPTION OF THE FIGURES

Having thus generally described the invention, reference will now be made to the accompanying drawings, showing by way of illustration a preferred embodiment thereof, and in which.

$$Z' = 1 - \frac{(3\ SD \text{ of pos. ctrls} + 3\ SD \text{ of neg. ctrls})}{(\text{mean pos. ctrl} - \text{mean neg. ctrl})}$$

Figure 3:
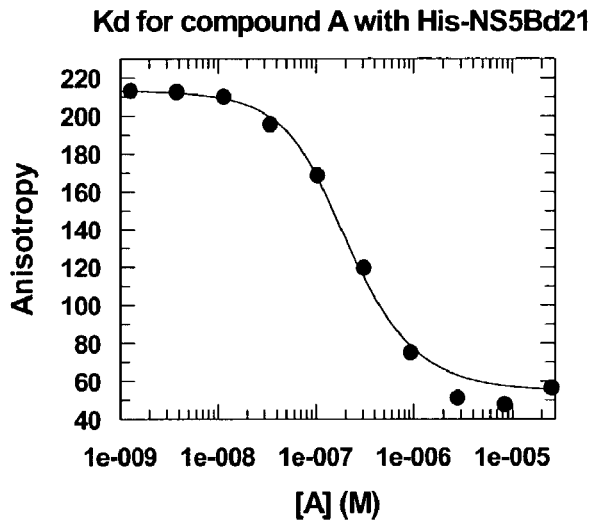
Figure 3:
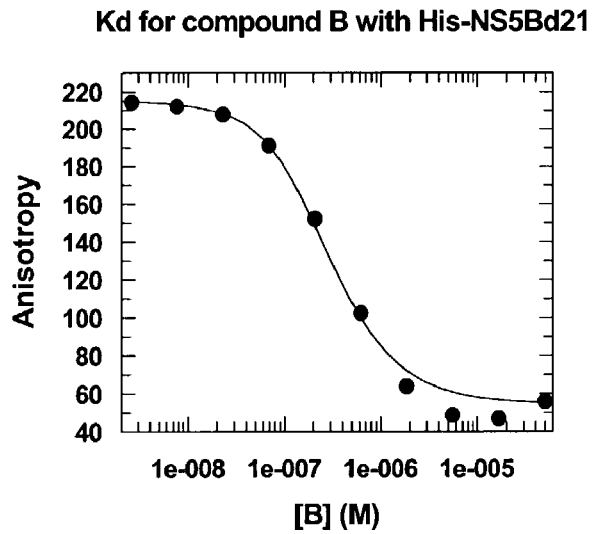

FIG. 3 illustrates $K_d$ determination for Compounds A and B, using the Fluorescence Polarization assay. Standard conditions of the 96-well plate Polarization assay (see Example 4) were used to determine the $K_d$ values of the compounds. $K_d$ values obtained for compound A and B are 31 and 41 nM, respectively, with $Q_b/Q_f$ values of 0.67 and 0.72.

Figure 4:
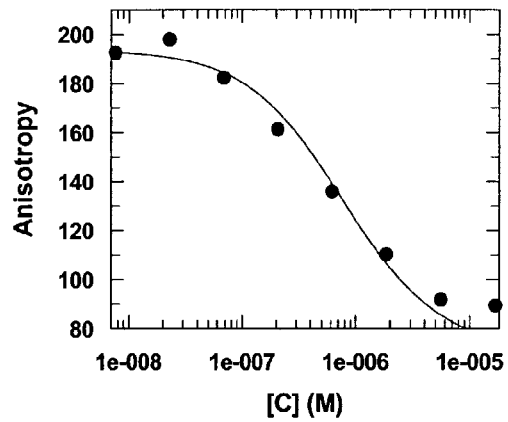
Figure 4:
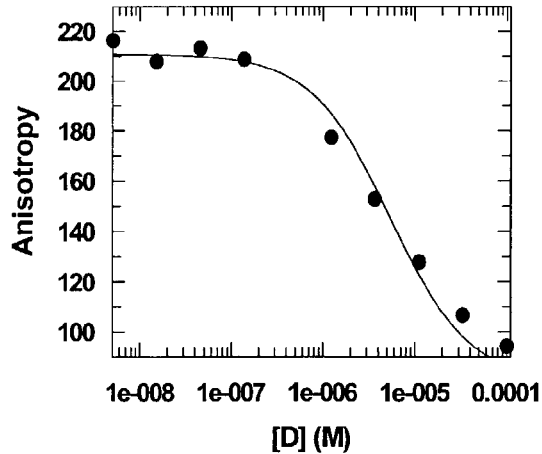

FIG. 4 illustrates $K_d$ determination for Compounds C and D, using the Fluorescence Polarization assay. Standard conditions of the 96-well plate Polarization assay (see Example 4) have been used to determine the $K_d$ values of some of our compounds. $K_d$ values obtained for compound C and D are 231 nM and 1.08 uM, respectively, with $Q_b/Q_f$ values of 0.74 and 0.66.

FIGS. 5 to 8 illustrate the titration of probe (i) with the NS5BΔ21-His in the presence of increasing (from 30 mM to 200 mM) concentration of NaCl. Standard conditions of the Fluorescence anisotropy analysis are described in Example 3. $K_d$ values obtained for this polymerase are 15.3 nM (30 mM NaCl), 39 nM (100 mM NaCl), 78 nM (150 mM NaCl) and finally 122 nM (200 mM NaCl).

Figure 9:
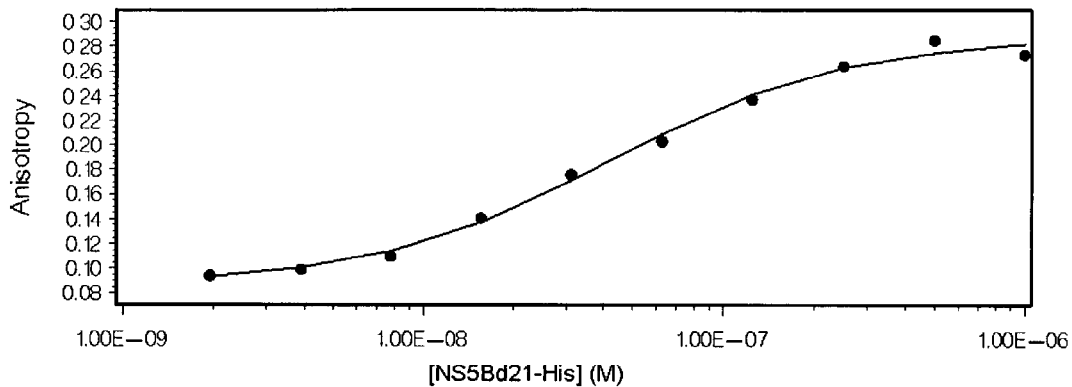

FIG. 9 illustrates the titration of probe (i) with the NS5BΔ21-His in Phosphate buffer pH 6.5. Standard conditions of the Fluorescence anisotropy analysis are described in Example 3. The $K_d$ of probe (i) for this polymerase under these conditions is 33 nM.

Figure 10:
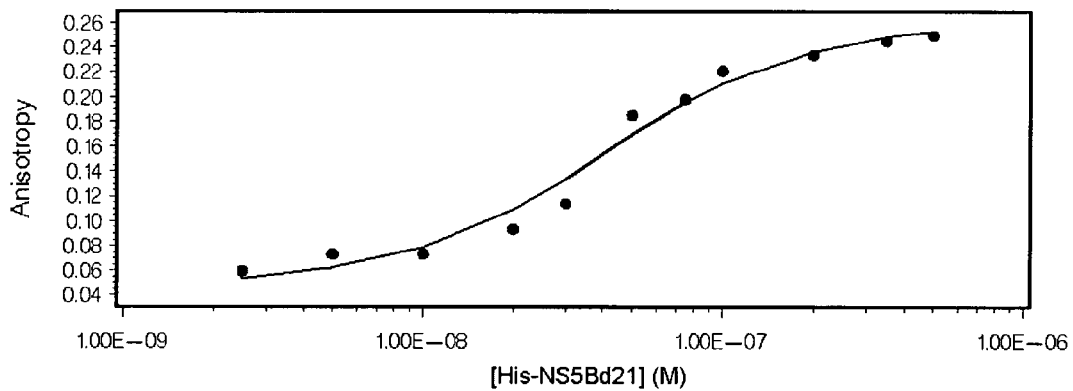

FIG. 10 illustrates the titration of probe (i) with the His-NS5BΔ21 polymerase. Standard conditions of the Fluorescence anisotropy analysis are described in Example 3. The $K_d$ of probe (i) for this N-terminally tagged polymerase is 18.1 nM.

FIG. 11 illustrates the titration of probe (ii) with the GBV-BΔ23-His polymerase. Standard conditions of the Fluorescence anisotropy analysis are described in Example 3. The $K_d$ of probe (ii) for this distantly related polymerase is 1.79 uM (estimated value with an incomplete curve).

FIG. 12 illustrates the titration of probe (ii) with the His-NS5BΔ21(H77c, HCV genotype 1a) polymerase. Standard conditions of the Fluorescence anisotropy analysis are described in Example 3. The $K_d$ of probe (ii) for this HCV genotype 1a polymerase is 18.2 nM.

DETAILED DESCRIPTION OF THE INVENTION

Definitions

The following definitions apply unless otherwise noted:

The term "affinity tag" means a moiety whose strong affinity for a ligand can be used to extract from a solution the entity to which the tag is attached. Examples of such tags include biotin or a derivative thereof, a histidine polypeptide, a polyarginine, an amylose sugar moiety or a defined epitope recognizable by a specific antibody. Such affinity tags are attached to the probe by well-known methods. The corresponding affinity ligands are also well known in the art.

An "analog" of the HCV NS5B polypeptide, for example HCV polymerase or a fragment thereof means a polypeptide modified by varying the amino acid sequence of the protein, e.g. by manipulation of the nucleic acid encoding the protein or by altering the protein itself. Such analogs of the natural amino acid sequence may involve insertion, addition, deletion or substitution of one or more amino acids, and may or may not alter the functional activity of the original HCV NS5B polypeptide. As mentioned above, the HCV NS5B polypeptide or protein used in the assay/method of the invention includes any fragment, derivative, variant or mutant which is derived from a HCV NS5B polypeptide and which retains at least one property or other characteristic of the HCV NS5B polypeptide.

The term "detectable label" refers to any group that is linked to a probe of the present invention such that when the probe is associated with the polymerase target, such label allows recognition either directly or indirectly of the probe such that it can be detected, measured and quantified. Examples of such "detectable labels" are intended to include, but are not limited to: photoreactive groups, fluorescent labels, chemiluminescent labels, colorimetric labels, enzymatic markers, radioactive isotopes. Such labels are attached to the probe by well known methods.

As used herein, the term "linker" refers to a chain of between 1 and 20 atoms selected from the group consisting of C, N, O, and S that covalently connects the aforesaid label to a probe of the present invention. Examples of such a chain include, but are not limited to, the following:

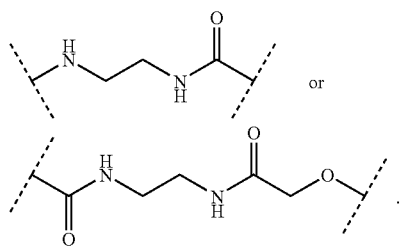

These linkers can also comprise a pair of affinity-tag/affinity-ligand, which together, bind the compound to a detectable label.

The term "photoreactive group" means a group that is transformed, upon activation by light, from an inert group to a reactive species, such as a free radical. Examples of such groups include, but are not limited to, benzophenones, azides, and the like.

As used herein, the term "probe" refer to a compound of formula (I) that is capable of binding to an HCV polymerase in a covalent or non-covalent manner. When the probe is bound in a non-covalent manner, it can be displaced by test compounds. When bound in a covalent manner, the probe can be used for cross-linking experiments wherein the HCV polymerase-probe adduct formation can be quantified and inhibited by test compounds.

As used herein, the terms "$(C_{1-3})$alkyl", "$(C_{1-4})$alkyl" or "$(C_{1-6})$alkyl", either alone or in combination with another radical, are intended to mean acyclic straight or branched chain alkyl radicals containing up to three, four and six carbon atoms respectively. Examples of such radicals include methyl, ethyl, propyl, butyl, hexyl, 1-methylethyl, 1-methylpropyl, 2-methylpropyl, 1,1-dimethylethyl.

As used herein, the term "$(C_{2-6})$ alkenyl", either alone or in combination with another radical, is intended to mean an unsaturated, acyclic straight chain radical containing two to six carbon atoms.

As used herein, the term $(C_{2-6})$alkynyl" either alone or in combination with another group, is intended to mean an unsaturated, acyclic straight chain sp hybridized radical containing 2 to six carbon atoms.

As used herein, the term "$(C_{3-7})$cycloalkyl", either alone or in combination with another radical, means a cycloalkyl radical containing from three to seven carbon atoms and includes cyclopropyl, cyclobutyl, cyclopentyl, cyclohexyl and cycloheptyl.

As used herein, the term "$(C_{5-7})$cycloalkenyl", either alone or in combination with another radical, means an unsaturated cyclic radical containing five to seven carbon atoms.

As used herein, the term "aryl", or "6- or 10-membered aryl" either alone or in combination with another radical means aromatic radical containing six or ten carbon atoms, for example phenyl or naphthyl.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, or boronic acids.

As used herein, the term "functional group equivalent" is intended to mean an element or a substituted derivative thereof, that is replaceable by another element that has similar electronic, hybridization or bonding properties.

As used herein, the term "halo" means a halogen atom and includes fluorine, chlorine, bromine and iodine.

As used herein, the term "haloalkyl" is intended to mean an alkyl that is described above in which each hydrogen atom may be successively replaced by a halogen atom, for example $CH_2Br$ or $CF_3$.

As used herein the term heteroatom means O, S or N.

As used herein, the term "heterocycle", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "heterobicyclic" as used herein, means a heterocycle as defined above fused to one or more other cycle, be it a heterocycle or any other cycle. Examples of such heterocycles include, but are not limited to, pyrrolidine, tetrahydrofuran, thiazolidine, pyrrole, thiophene, coumarin, hydantoin, diazepine, 1H-imidazole, isoxazole, thiazole, tetrazole, piperidine, 1,4-dioxane, 4-morpholine, pyridine, pyridine-N-oxide, pyrimidine, thiazolo[4,5-b]-pyridine, quinoline, or indole, or the following heterocycles:

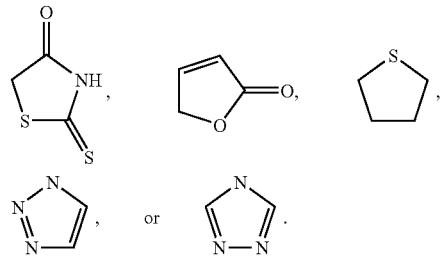

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, thiazolo[4,5-b]-pyridine, quinoline, or indole, or the following:

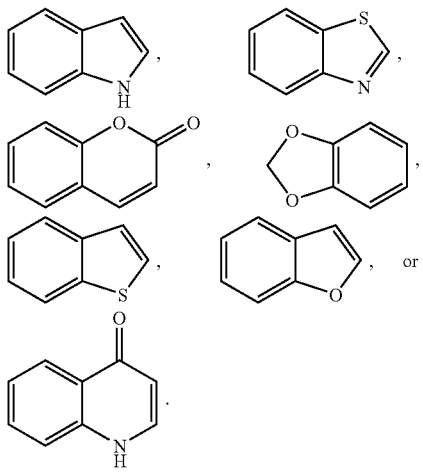

As used herein, the term "Het" defines a 5- or 6-membered heterocycle having 1 to 4 heteroatoms selected from O, N, and S, or a 9- or 10-membered heterobicycle having 1 to 4 heteroatoms selected from O, N and S.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as SOR, $SO_2R$, or $SO_3R$.

It is intended that the term "substituted" when applied in conjunction with a radical having more than one moiety such as $C_{1-6}$alkyl-aryl, or $C_{1-6}$alkyl-Het, such substitution applies to both moieties i.e. both the alkyl and aryl or Het moieties can be substituted with the defined substituents.

DESCRIPTION OF PREFERRED EMBODIMENTS

Preferably, according to the first aspect, the invention provide a method for identifying inhibitors of HCV polymerase comprising the steps of:
a) contacting an HCV polymerase with a probe of formula I so as to form a complex comprising said probe bound to said polymerase;
b) measuring a signal from said complex to establish a base line level;
c) incubating the product of step a) with a test compound;
d) measuring the signal from said complex; and
e) comparing the signal from step d) with the signal from step b);

whereby a decrease in said signal is an indication that said test compound is an inhibitor of said polymerase.

As will be understood by a person skilled in the art, the association of a specific probe of the invention with the NS5B polymerase can be measured directly or indirectly in a variety of ways. The probe and NS5B polymerase need not be labeled and affinity tagged respectively. The association of a specific probe with the HCV NS5B polymerase can be monitored and quantified directly by a change in the intrinsic spectral properties of a tagged or un-tagged NS5B protein and/or by a change in the intrinsic spectral properties of a specific probe. A direct measurement of inhibitor-NS5B association can also be achieved by immobilizing one of these two components on a matrix and measuring association through plasma-resonance detection technology. An assay that quantifies probe-NS5B complex association may also incorporate a photo-reactive label (such as a phenylazide or benzophenone) on the probe (for example probes (v) and (vi) below) and measure the amount of label irreversibly bound to the NS5B (adduct) following photoactivation of the probe.

Preferably, according to a first aspect of the present invention, there is provided a probe of formula:

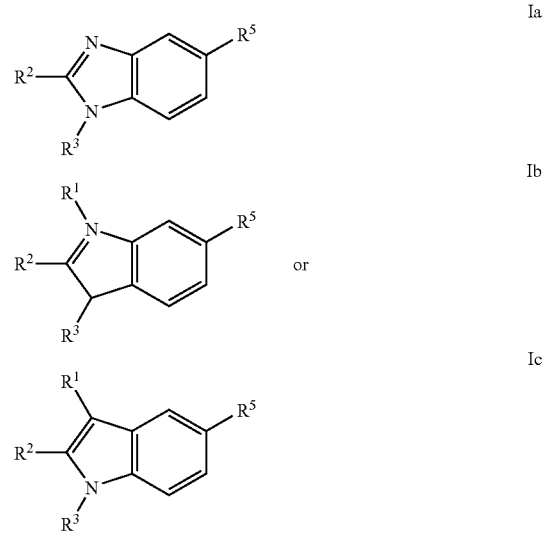

wherein
$R^1$ is selected from the group consisting of: H or $(C_{1-6})$alkyl;
$R^2$ is $CON(R^{22})_2$, wherein each $R^{22}$ is independently H, $(C_{1-6})$alkyl, $(C_{3-7})$cycloalkyl, $(C_{5-7})$cycloalkenyl, 6 or 10-membered aryl or Het, or both $R^{22}$ are bonded together to form a 5, 6 or 7-membered saturated heterocycle with the nitrogen to which they are attached;
or $R^2$ is selected from: H, halogen, $(C_{1-6})$alkyl, haloalkyl, $(C_{2-6})$alkenyl, $(C_{5-7})$cycloalkenyl, 6 or 10-membered aryl or Het; wherein each of said alkyl, haloalkyl, $(C_{2-6})$alkenyl, $(C_{5-7})$cycloalkenyl, aryl or Het is optionally substituted with $R^{20}$, wherein $R^{20}$ is defined as:
1 to 4 substituents selected from: halogen, $NO_2$, cyano, azido, $C(=NH)NH_2$, $C(=NH)NH(C_{1-6})$alkyl or $C(=NH)NHCO(C_{1-6})$alkyl; or
1 to 4 substituents selected from:
a) $(C_{1-6})$alkyl or haloalkyl, $(C_{3-7})$cycloalkyl, $(C_{2-6})$alkenyl, $(C_{2-8})$alkynyl, $(C_{1-6})$ alkyl-$(C_{3-7})$cycloalkyl, all of which optionally substituted with $R^{150}$;
b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;
c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SR^{108}$, $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$ cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$-alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, (C1-6alkyl)aryl or (C1-6alkyl)Het, all of which being optionally substituted with $R^{150}$;

wherein $R^{150}$ is preferably:

1 to 3 substituents selected from: halogen, $NO_2$, cyano or azido; or 1 to 3 substituents selected from:

a) $(C_{1-6})$alkyl or haloalkyl, $(C_{3-7})$cycloalkyl, $(C_{2-6})$alkenyl, $(C_{2-8})$alkynyl, $(C_{1-6})$alkyl-$(C_{3-7})$cycloalkyl, all of which optionally substituted with $R^{160}$;

b) $OR^{104}$ wherein $R^{104}$ is H, $(C_{1-6}$alkyl) or $(C_{3-7})$cycloalkyl, said alkyl or cycloalkyl optionally substituted with $R^{160}$;

d) $SR^{108}$, $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, or both $R^{108}$ are covalently bonded together and to the nitrogen to which they are attached to form a 5, 6 or 7-membered saturated heterocycle, said alkyl, cycloalkyl, aryl, Het and heterocycle being optionally substituted with $R^{160}$;

e) $NR^{111}R^{112}$ wherein $R^{111}$ is H, $(C_{1-6})$alkyl, or $(C_{3-7})$cycloalkyl, and $R^{112}$ is H, $(C_{1-6})$alkyl or $(C_{3-7})$cycloalkyl, $COOR^{115}$ or $SO_2R^{115}$ wherein $R^{115}$ is $(C_{1-6})$alkyl or $(C_{3-7})$cycloalkyl, or both $R^{111}$ and $R^{112}$ are covalently bonded together and to the nitrogen to which they are attached to form a 5, 6 or 7-membered saturated heterocycle, said alkyl, cycloalkyl and heterocycle being optionally substituted with $R^{160}$;

f) $NR^{116}COR^{117}$ wherein $R^{126}$ and $R^{117}$ is each H, $(C_{1-6})$alkyl or $(C_{3-7})$cycloalkyl said $(C_{1-6})$alkyl and $(C_{3-7})$cycloalkyl being optionally substituted with $R^{160}$;

g) $NR^{118}CONR^{119}R^{120}$, wherein $R^{118}$, $R^{119}$ and $R^{120}$ is each H, $(C_{1-6})$alkyl or $(C_{3-7})$cycloalkyl, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, and heterocycle being optionally substituted with $R^{160}$;

h) $NR^{121}COCOR^{122}$ wherein $R^{121}$ is H, $(C_{1-6})$alkyl or $(C_{3-4})$cycloalkyl, said alkyl and cycloalkyl being optionally substituted with $R^{160}$; or $R^{122}$ is $OR^{123}$ or $N(R^{124})_2$ wherein $R^{123}$ and each $R^{124}$ is independently H, $(C_{1-6}$alkyl) or $(C_{3-7})$cycloalkyl, or both $R^{124}$ are covalently bonded together to form a 5, 6 or 7-membered saturated heterocycle, said alkyl, cycloalkyl and heterocycle being optionally substituted with $R^{160}$;

i) $COR^{127}$ wherein $R^{127}$ is H, $(C_{1-6})$alkyl or $(C_{3-7})$cycloalkyl, said alkyl and cycloalkyl being optionally substituted with $R^{160}$;

j) COOR$^{128}$ wherein R$^{128}$ is H, (C$_{1-6}$)alkyl or (C$_{3-7}$) cycloalkyl, said (C$_{1-6}$)alkyl and (C$_{3-7}$)cycloalkyl being optionally substituted with R$^{160}$; and k) CONR$^{129}$R$^{130}$ wherein R$^{129}$ and R$^{130}$ are independently H, (C$_{1-6}$)alkyl or (C$_{3-7}$)cycloalkyl, or both R$^{129}$ and R$^{130}$ are covalently bonded together and to the nitrogen to which they are attached to form a 5, 6 or 7-membered saturated heterocycle, said alkyl, cycloalkyl and heterocycle being optionally substituted with R$^{160}$;

wherein R$^{160}$ is defined as 1 or 2 substituents selected from: halogen, CN, C$_{1-6}$alkyl, haloalkyl, COOR$^{161}$, OR$^{161}$, N(R$^{162}$)$_2$, SO$_2$N(R$^{162}$)$_2$, or CON(R$^{162}$)$_2$, wherein R$^{161}$ and each R$^{162}$ is independently H, (C$_{1-6}$)alkyl, (C$_{3-7}$)cycloalkyl or (C$_{1-6}$) alkyl-(C$_{3-7}$)cycloalkyl; or both R$^{162}$ are covalently bonded together and to the nitrogen to which they are attached to form a 5, 6 or 7-membered saturated heterocycle;

R$^3$ is selected from (C$_{3-7}$)cycloalkyl, (C$_{6-10}$)bicycloalkyl, 6- or 10-membered aryl, or Het;

R$^5$ is —C(O)-Z, wherein

Z is OR$^6$ wherein R$^6$ is C$_{1-6}$alkyl substituted with:

1 to 4 substituents selected from: OPO$_3$H, NO$_2$, cyano, azido, C(=NH)NH$_2$, C(=NH)NH(C$_{1-6}$)alkyl or C(=NH)NHCO(C$_{1-6}$)alkyl; or 1 to 4 substituents selected from:

a) (C$_{1-6}$)alkyl or haloalkyl, (C$_{3-7}$)cycloalkyl, C$_{3-7}$ spirocycloalkyl optionally containing 1 or 2 heteroatom, (C$_{2-6}$)alkenyl, (C$_{2-8}$)alkynyl, (C$_{1-6}$)alkyl-(C$_{3-7}$)cycloalkyl, all of which optionally substituted with R$^{150}$;

b) OR$^{104}$ wherein R$^{104}$ is (C$_{1-6}$alkyl) substituted with R$^{150}$, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said cycloalkyl, aryl, Het, (C$_{1-6}$alkyl)aryl or (C$_{1-6}$alkyl)Het being optionally substituted with R$^{150}$;

c) OCOR$^{105}$ wherein R$^{105}$ is (C$_{1-6}$)alkyl, (C$_{3-7}$)cycloalkyl, (C$_{1-6}$)alkyl-(C$_{3-7}$)cycloalkyl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{150}$;

d) SR$^{108}$, SO$_3$H, SO$_2$N(R$^{108}$)$_2$ or SO$_2$N(R$^{108}$)C(O)R$^{108}$ wherein each R$^{108}$ is independently H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het or both R$^{108}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het or heterocycle being optionally substituted with R$^{150}$;

e) NR$^{111}$R$^{112}$ wherein R$^{111}$ is (C$_{1-6}$)alkyl substituted with R$^{150}$, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het, and R$^{112}$ is CN, (C$_{1-6}$)alkyl substituted with R$^{50}$, (C$_{3-7}$)cycloalkyl or (C$_{1-6}$)alkyl-(C$_{3-7}$)cycloalkyl, aryl, Het, (C$_{1-6}$alkyl)aryl, (C$_{1-6}$alkyl)Het, COOR$^{115}$ or SO$_2$R$^{115}$ wherein R$^{115}$ is (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or both R$^{111}$ and R$^{112}$ are covalently bonded together and to the nitrogen to which they are attached to form a 5, 6 or 7-membered saturated heterocycle, said cycloalkyl, aryl, Het, (C$_{1-6}$alkyl)aryl or (C$_{1-6}$alkyl)Het, or heterocycle being optionally substituted with R$^{150}$;

f) NR$^{116}$COR$^{117}$ wherein R$^{116}$ and R$^{117}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het being optionally substituted with R$^{150}$;

g) NR$^{118}$CONR$^{119}$R$^{120}$, wherein R$^{118}$, R$^{119}$ and R$^{120}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or R$^{118}$ is covalently bonded to R$^{119}$ and to the nitrogen to which they are attached to form a 5, 6 or 7-membered saturated heterocycle; or R$^{119}$ and R$^{120}$ are covalently bonded together and to the nitrogen to which they are attached to form a 5, 6 or 7-membered saturated heterocycle; said alkyl, cycloalkyl, (C$_{1-6}$)alkyl-(C$_{3-7}$)cycloalkyl, aryl, Het, (C$_{1-6}$alkyl)aryl or (C$_{1-6}$alkyl)Het or heterocycle being optionally substituted with R$^{150}$;

h) NR$^{121}$COCOR$^{122}$ wherein R$^{121}$ and R$^{122}$ is each is H, (C$_{1-6}$)alkyl, (C$_{3-7}$)cycloalkyl, (C$_{1-6}$)alkyl-(C$_{3-7}$)cycloalkyl, a 6- or 10-membered aryl, Het, (C$_{1-6}$alkyl)aryl or (C$_{1-6}$alkyl)Het, said alkyl, cycloalkyl, alkyl-cycloalkyl, aryl, Het, (C$_{1-6}$alkyl)aryl or (C$_{1-6}$alkyl)Het being optionally substituted with R$^{150}$; or R$^{122}$ is OR$^{123}$ or N(R$^{124}$)$_2$ wherein R$^{123}$ and each R$^{124}$ is independently H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or R$^{124}$ is OH or O(C$_{1-6}$alkyl) or both R$^{124}$ are covalently bonded together to form a 5, 6 or 7-membered saturated heterocycle, said alkyl, cycloalkyl, alkyl-cycloalkyl, aryl, Het, (C$_{1-6}$alkyl)aryl or (C$_{1-6}$alkyl)Het and heterocycle being optionally substituted with R$^{150}$;

i) COR$^{127}$ wherein R$^{127}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{150}$;

j) COOR$^{128}$ wherein R$^{112}$ is (C$_{1-6}$)alkyl substituted with R$^{150}$, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said (C$_{3-7}$)cycloalkyl, or (C$_{1-6}$)alkyl-(C$_{3-7}$)cycloalkyl, aryl, Het, (C$_{1-6}$alkyl)aryl and (C$_{1-6}$alkyl)Het being optionally substituted with R$^{150}$;

k) CONR$^{129}$R$^{130}$ wherein R$^{129}$ and R$^{130}$ are independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or both R$^{129}$ and R$^{130}$ are covalently bonded together and to the nitrogen to which they are attached to form a 5, 6 or 7-membered saturated heterocycle, said alkyl, cycloalkyl, alkyl-cycloalkyl, aryl, Het, (C$_{1-6}$alkyl)aryl, (C$_{1-6}$alkyl)Het and heterocycle being optionally substituted with R$^{150}$;

l) aryl, Het, (C$_{1-6}$alkyl)aryl or (C$_{1-6}$alkyl)Het, all of which being optionally substituted with R$^{150}$;

1 to 3 substituents selected from: halogen, NO$_2$, cyano, azido or 1 to 3 substituents selected from:

a) (C$_{1-6}$)alkyl or haloalkyl, (C$_{3-7}$)cycloalkyl, C$_{3-7}$ spirocycloalkyl optionally containing 1 or 2 heteroatom, (C$_{2-6}$)alkenyl, (C$_{1-6}$)alkyl-(C$_{3-7}$)cycloalkyl, all of which optionally substituted with R$^{160}$;

b) OR$^{104}$ wherein R$^{104}$ is H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{160}$;

d) SO$_3$H, SO$_2$N(R$^{108}$)$_2$ or SO$_2$N(R$^{108}$)C(O)R$^{108}$ wherein each R$^{108}$ is independently H, (C$_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het or heterocycle being optionally substituted with $R^{160}$;

e) $NR^{111}R^{112}$ wherein $R^{111}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, and $R^{112}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl, ($C_{1-6}$alkyl)Het, COOR$^{113}$ or SO$_2$R$^{115}$ wherein $R^{115}$ is ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het, or heterocycle being optionally substituted with $R^{160}$;

f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{160}$;

g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{119}$ and $R^{120}$ are covalently bonded together and to the nitrogen to which they are attached to form a 5, 6 or 7-membered saturated heterocycle; said alkyl, cycloalkyl, ($C_{1-6}$alkyl-($C_{3-7}$) cycloalkyl, aryl, Het, ($C_{1-6}$alkyl)aryl or ($C_{1-6}$alkyl)Het or heterocycle being optionally substituted with $R^{160}$;

h) $NR^{121}COCOR^{122}$ wherein $R^{121}$ is H, ($C_{1-6}$)alkyl optionally substituted with $R^{160}$; or $R^{122}$ is OR$^{123}$ or N(R$^{124}$)$_2$ wherein $R^{123}$ and each $R^{124}$ is independently H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or $R^{124}$ is OH or O($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{160}$;

j) tetrazole, COOR$^{128}$ wherein $R^{128}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl and ($C_{1-6}$alkyl)Het being optionally substituted with $R^{160}$; and k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, COOR$^{161}$, SO$_3$H, SO$_2$R$^{161}$, OR$^{161}$, N(R$^{162}$)$_2$, SO$_2$N(R$^{162}$)$_2$, or CON(R$^{162}$)$_2$, wherein $R^{161}$ and each $R^{162}$ is independently H, ($C_{1-6}$)alkyl, ($C_{3-7}$)cycloalkyl or ($C_{1-6}$)alkyl-($C_{3-7}$)cycloalkyl; or both $R^{162}$ are covalently bonded together and to the nitrogen to which they are attached to form a 5, 6 or 7-membered saturated heterocycle;

or Z is N(R$^{6a}$)R$^6$, wherein R$^{6a}$ is H or ($C_{1-6}$alkyl); and
R$^6$ is ($C_{1-6}$)alkyl optionally substituted with:
1 to 4 substituents selected from: OPO$_3$H, NO$_2$, cyano, azido, C(═NH)NH$_2$, C(═NH)NH($C_{1-6}$)alkyl or C(═NH)NHCO($C_{1-6}$)alkyl; or 1 to 4 substituents selected from:
a) ($C_{1-6}$)alkyl substituted with $R^{150a}$, haloalkyl, ($C_{3-7}$)cycloalkyl, $C_{3-7}$ spirocycloalkyl optionally containing 1 or 2 heteroatom, ($C_{2-6}$)alkenyl, ($C_{2-8}$)alkynyl, ($C_{1-6}$)alkyl-($C_{3-7}$)cycloalkyl, all of which optionally substituted with $R^{150}$, wherein $R^{150a}$ is the same as $R^{150}$ but is not halogen, OR$^{150b}$, COOR$^{150b}$, N(R$^{150b}$)$_2$, wherein $R^{150b}$ is H or $C_{1-6}$alkyl;

b) OR$^{104}$ wherein $R^{104}$ is ($C_{1-6}$alkyl) substituted with $R^{150}$, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said cycloalkyl, aryl, Het, ($C_{1-6}$alkyl)aryl or ($C_{1-6}$alkyl)Het being optionally substituted with $R^{150}$;

c) OCOR$^{105}$ wherein $R^{105}$ is ($C_{1-6}$)alkyl, ($C_{3-7}$)cycloalkyl, ($C_{1-6}$)alkyl-($C_{3-7}$)cycloalkyl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{150}$;

d) SO$_3$H, SO$_2$N(R$^{108}$)$_2$ or SO$_2$N(R$^{108}$)C(O)R$^{108}$ wherein each $R^{108}$ is independently H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het or heterocycle being optionally substituted with $R^{150}$;

e) $NR^{111}R^{112}$ wherein $R^{111}$ is ($C_{1-6}$)alkyl substituted with $R^{150}$, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, and $R^{112}$ is H, CN, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl, ($C_{1-6}$alkyl)Het or $R^{111}$ is H and $R^{112}$ is SO$_2$R$^{115}$ wherein $R^{111}$ is ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or both $R^{111}$ and $R^{112}$ are covalently bonded together and to the nitrogen to which they are attached to form a 5, 6 or 7-membered saturated heterocycle, said cycloalkyl, aryl, Het, ($C_{1-6}$alkyl)aryl or ($C_{1-6}$alkyl)Het, or heterocycle being optionally substituted with $R^{150}$;

f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$) cycloalkyl, aryl, Het, ($C_{1-6}$alkyl)aryl or ($C_{1-6}$alkyl)Het being optionally substituted with $R^{150}$;

g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle; or $R^{111}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6})$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is $(C_{1-6})$alkyl substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$; and wherein $R^{150}$ is selected from:

1 to 3 substituents selected from: halogen, $NO_2$, cyano, azido or 1 to 3 substituents selected from:

a) $(C_{1-6})$alkyl or haloalkyl, $(C_{3-7})$cycloalkyl, $C_{3-1}$ spirocycloalkyl optionally containing 1 or 2 heteroatom, $(C_{2-6})$alkenyl, $(C_{1-6})$alkyl-$(C_{3-7})$cycloalkyl, all of which optionally substituted with $R^{160}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

d) $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$-alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{160}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{160}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{160}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$-alkyl)Het, or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$ cycloalkyl, aryl, Het, $(C_{1-6}$alkyl)aryl or $(C_{1-6}$alkyl)Het or heterocycle being optionally substituted with $R^{160}$;

h) $NR^{121}COCOR^{122}$ wherein $R^{121}$ is H, $(C_{1-6})$alkyl optionally substituted with $R^{160}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{160}$;

j) tetrazole, $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$ alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{160}$; and k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, $(C_{1-6})$alkyl, $(C_{3-7})$cycloalkyl or $(C_{1-6})$alkyl-$(C_{3-7})$cycloalkyl; or both $R^{162}$ are covalently bonded together and to the nitrogen to which they are attached to form a 5, 6 or 7-membered saturated heterocycle.

or $R^6$ is

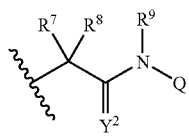

wherein, preferably, $R^7$ and $R^8$ are each independently H, $(C_{1-6})$alkyl, haloalkyl, $(C_{3-7})$cycloalkyl, 6- or 10-membered aryl, Het, $(C_{1-6})$alkyl-aryl, $(C_{1-6})$alkyl-Het, wherein said alkyl, cycloalkyl, aryl, Het, $(C_{1-6})$alkyl-aryl, $(C_{1-6})$alkyl-Het are optionally substituted with $R^{70}$; or $R^7$ and $R^8$ are covalently bonded together to form second $(C_{3-7})$cycloalkyl or a 4, 5- or 6-membered heterocycle having from 1 to 3 heteroatom selected from O, N, and S; or when Z is $N(R^{6a})R^6$, either of $R^7$ or $R^8$ is covalently bonded to $R^{6a}$ to form a nitrogen-containing 5- or 6-membered heterocycle;

wherein, preferably, $R^{70}$ is selected from:

1 to 4 substituents selected from: halogen, $NO_2$, cyano, azido; or 1 to 4 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{150}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$-alkyl) Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; and $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or O$(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$;

wherein, preferably, $R^{150}$ is selected from:

1 to 3 substituents selected from: halogen, $NO_2$, cyano, azido; or 1 to 3 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, all of which optionally substituted with $R^{160}$;

b) $OR^{104}$ wherein $R^{104}$ is H, $(C_{1-6}$alkyl) or $(C_{3-7})$cycloalkyl, said alkyl and cycloalkyl being optionally substituted with $R^{160}$;

d) $SO_2N(R^{108})_2$ wherein $R^{108}$ is H, $(C_{1-6})$alkyl or $(C_{3-7})$cycloalkyl, said alkyl or cycloalkyl being optionally substituted with $R^{160}$;

e) $NR^{111}R^{112}$ wherein $R^{111}$ is H, $(C_{1-6})$alkyl or $(C_{3-7})$cycloalkyl, and $R^{112}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or SO$_2$R$^{115}$ wherein R$^{115}$ is (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or both R$^{111}$ and R$^{112}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het, or heterocycle being optionally substituted with R$^{160}$;

f) NR$^{116}$COR$^{117}$ wherein R$^{116}$ and R$^{117}$ is each H, (C$_{1-6}$)alkyl or (C$_{3-7}$)cycloalkyl, said (C$_{1-6}$)alkyl or (C$_{3-7}$)cycloalkyl being optionally substituted with R$^{160}$;

g) NR$^{118}$CONR$^{119}$R$^{120}$, wherein R$^{118}$, R$^{119}$ and R$^{120}$ is each H, (C$_{1-6}$)alkyl or (C$_{3-7}$)cycloalkyl; or R$^{119}$ and R$^{120}$ are covalently bonded together and to the nitrogen to which they are attached to form a 5, 6 or 7-membered saturated heterocycle; said alkyl, cycloalkyl or heterocycle being optionally substituted with R$^{160}$;

h) NR$^{121}$COCOR$^{122}$ wherein R$^{121}$ is H, (C$_{1-6}$)alkyl or (C$_{3-7}$)cycloalkyl, said alkyl or cycloalkyl being optionally substituted with R$^{160}$; or R$^{122}$ is OR$^{123}$ or N(R$^{124}$)$_2$ wherein R$^{123}$ and each R$^{124}$ is independently H, (C$_{1-6}$alkyl) or (C$_{3-7}$)cycloalkyl, or R$^{124}$ is OH or O(C$_{1-6}$alkyl) or both R$^{124}$ are covalently bonded together to form a 5, 6 or 7-membered saturated heterocycle, said alkyl, cycloalkyl and heterocycle being optionally substituted with R$^{160}$;

j) tetrazole, COOR$^{128}$ wherein R$^{128}$ is H, (C$_{1-6}$)alkyl or (C$_{3-7}$)cycloalkyl, said (C$_{1-6}$)alkyl and (C$_{3-7}$)cycloalkyl being optionally substituted with R$^{160}$; and k) CONR$^{129}$R$^{130}$ wherein R$^{129}$ and R$^{130}$ are independently H, (C$_{1-6}$)alkyl or (C$_{3-7}$)cycloalkyl, or both R$^{129}$ and R$^{130}$ are covalently bonded together and to the nitrogen to which they are attached to form a 5, 6 or 7-membered saturated heterocycle, said alkyl, cycloalkyl and heterocycle being optionally substituted with R$^{160}$;

wherein R$^{160}$ is defined as 1 or 2 substituents selected from: tetrazole, halogen, CN, C$_{1-6}$alkyl, haloalkyl, COOR$^{161}$, OR$^{161}$, N(R$^{162}$)$_2$ or CON(R$^{162}$)$_2$, wherein R$^{161}$ and each R$^{162}$ is independently H or (C$_{1-6}$)alkyl;

R$^9$ is H; or R$^9$ is covalently bonded to either of R$^7$ or R$^8$ to form a 5- or 6-membered heterocycle; and Q is a 6- or 10-membered aryl, Het, all of which being optionally substituted with:

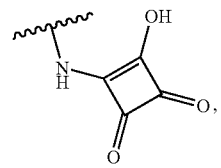

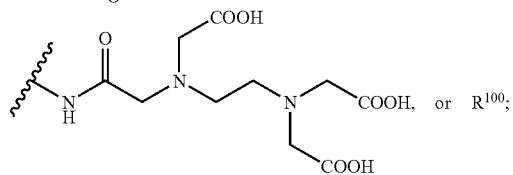, or R$^{100}$;

wherein R$^{100}$ is:
1 to 4 substituents selected from: halogen, NO$_2$, cyano or azido; or
1 to 4 substituents selected from:
a) (C$_{1-6}$)alkyl or haloalkyl, (C$_{3-7}$)cycloalkyl, (C$_{2-6}$)alkenyl, (C$_{2-8}$)alkynyl, (C$_{1-6}$) alkyl-(C$_{3-7}$)cycloalkyl, all of which optionally substituted with R$^{150}$;

b) OR$^{104}$ wherein R$^{104}$ is H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{150}$;

e) NR$^{111}$R$^{112}$ wherein R$^{111}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het, and R$^{112}$ is H, CN, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl, (C$_{1-6}$alkyl)Het, COOR$^{113}$ or SO$_2$R$^{115}$wherein R$^{115}$ is (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or both R$^{111}$ and R$^{112}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het, or heterocycle being optionally substituted with R$^{150}$;

f) NR$^{116}$COR$^{117}$ wherein R$^{116}$ and R$^{117}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het being optionally substituted with R$^{150}$;

g) NR$^{118}$CONR$^{119}$R$^{120}$, wherein R$^{118}$, R$^{119}$ and R$^{120}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or R$^{118}$ is covalently bonded to R$^{119}$ and to the nitrogen to which they are attached to form a 5, 6 or 7-membered saturated heterocycle; or R$^{119}$ and R$^{120}$ are covalently bonded together and to the nitrogen to which they are attached to form a 5, 6 or 7-membered saturated heterocycle; said alkyl, cycloalkyl, (C$_{1-6}$)alkyl-(C$_{3-7}$)cycloalkyl, aryl, Het, (C$_{1-6}$alkyl)aryl or (C$_{1-6}$alkyl)Het or heterocycle being optionally substituted with R$^{150}$;

h) NR$^{121}$COCOR$^{122}$ wherein R$^{121}$ and R$^{122}$ is each is H, (C$_{1-6}$)alkyl, (C$_{3-7}$)cycloalkyl, (C$_{1-6}$)alkyl-(C$_{3-7}$)cycloalkyl, a 6- or 10-membered aryl, Het, (C$_{1-6}$alkyl)aryl or (C$_{1-6}$alkyl)Het, said alkyl, cycloalkyl, alkyl-cycloalkyl, aryl, Het, (C$_{1-6}$alkyl)aryl or (C$_{1-6}$alkyl)Het being optionally substituted with R$^{150}$; or R$^{122}$ is OR$^{123}$ or N(R$^{124}$)$_2$ wherein R$^{123}$ and each R$^{124}$ is independently H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or R$^{124}$ is OH or O(C$_{1-6}$alkyl) or both R$^{124}$ are covalently bonded together to form a 5, 6 or 7-membered saturated heterocycle, said alkyl, cycloalkyl, alkyl-cycloalkyl, aryl, Het, (C$_{1-6}$alkyl)aryl or (C$_{1-6}$alkyl)Het and heterocycle being optionally substituted with R$^{150}$;

j) COOR$^{128}$ wherein R$^{128}$ is H, (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl and (C$_{1-6}$alkyl)Het being optionally substituted with R$^{150}$;

k) CONR$^{129}$R$^{130}$ wherein R$^{129}$ and R$^{130}$ are independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$ alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$;

wherein $R^{150}$ is selected from:

1 to 3 substituents selected from: halogen, $NO_2$, cyano or azido; or 1 to 3 substituents selected from:

a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$ cycloalkyl, all of which optionally substituted with $R^{160}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{160}$;

d) $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl) Het or heterocycle being optionally substituted with $R^{160}$;

e) $NR^{111}R^{112}$ wherein $R^{111}$ is H, $(C_{1-6})$alkyl, $(C_{3-7})$ cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl) Het, or heterocycle being optionally substituted with $R^{160}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$ cycloalkyl, aryl, Het, $(C_{1-6}$alkyl)aryl or $(C_{1-6}$alkyl) Het being optionally substituted with $R^{160}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$ alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{160}$;

h) $NR^{121}COCOR^{122}$ wherein $R^{121}$ is H, $(C_{1-6})$alkyl optionally substituted with $R^{160}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$ alkyl-$(C_{3-7})$cycloalkyl, aryl, Het, $(C_{1-6}$alkyl)aryl or $(C_{1-6}$alkyl)Het, or $R^{124}$ is OH or O($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl) aryl or $(C_{1-6}$alkyl)Het and heterocycle being optionally substituted with $R^{160}$;

j) tetrazole, $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$ alkyl, $(C_{3-7})$cycloalkyl, or $(C_{1-6})$alkyl-$(C_{3-7})$ cycloalkyl, aryl, Het, $(C_{1-6}$alkyl)aryl and $(C_{1-6}$alkyl) Het being optionally substituted with $R^{160}$; and k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$ alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SR^{161}$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, $(C_{1-6})$alkyl, $(C_{3-7})$cycloalkyl or $(C_{1-6})$alkyl-$(C_{3-7})$ cycloalkyl; or both $R^{162}$ are covalently bonded together and to the nitrogen to which they are attached to form a 5, 6 or 7-membered saturated heterocycle;

or a salt thereof;

wherein said probe comprises a detectable label attached to any suitable position, whereby said probe binds to an HCV polymerase or an analog thereof and is capable of being displaced by an inhibitor thereof.

More preferably, the probe of the invention is a compound of formula:

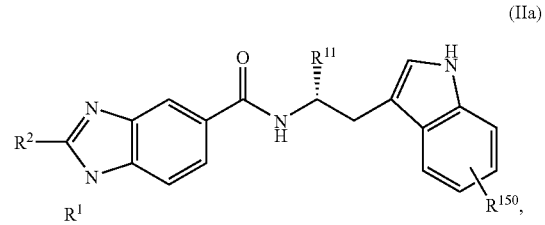

(IIa)

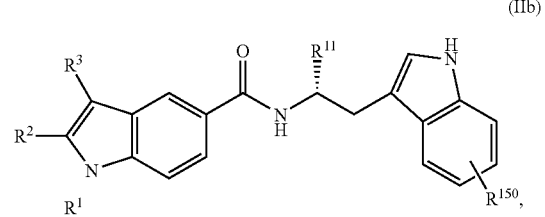

(IIb)

-continued

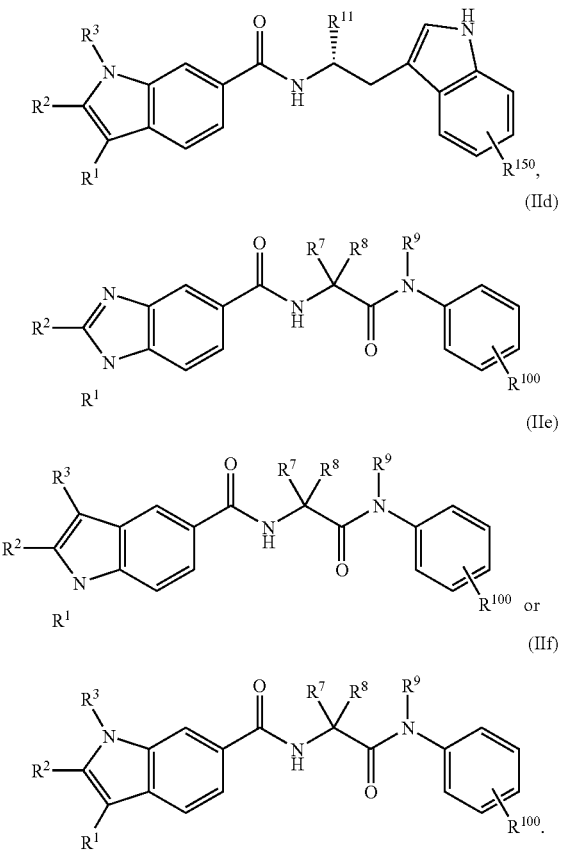

wherein $R^1$ is $(C_{5-6})$cycloalkyl;

$R^2$ is phenyl, or Het both being optionally substituted with $R^{20}$;

$R^3$, $R^7$, $R^8$, $R^9$, $R^{100}$, and $R^{150}$ are as defined above;

$R^{11}$ is $OPO_3H$, $NO_2$, cyano, azido, $C(=NH)NH_2$, $C(=NH)NH(C_{1-6})$alkyl or $C(=NH)NHCO(C_{1-6})$alkyl; or a) $(C_{1-6})$alkyl substituted with $R^{150a}$, haloalkyl, $(C_{3-7})$ cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{150}$, wherein $R^{150a}$ is the same as $R^{150}$ but is not halogen, $OR^{150b}$, $COOR^{150b}$, $N(R^{150b})_2$, wherein $R^{151b}$ is H or $C_{1-6}$alkyl;

b) $OR^{104}$ wherein $R^{104}$ is $(C_{1-6})$alkyl substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said cycloalkyl, aryl, Het, $(C_{1-6}$alkyl)aryl or $(C_{1-6}$alkyl)Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{106}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is $(C_{1-6})$alkyl substituted with $R^{150}$, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het or $R^{111}$ is H and $R^{112}$ is $SO_2R^{115}$ wherein $R^{111}$ is $(C_{1-6})$alkyl, $(C_{3-7})$cycloalkyl, or $(C_{1-6})$alkyl-$(C_{1-6})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-4})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$-alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl) aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is $(C_{1-6})$alkyl substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$-alkyl)Het, said $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$ alkyl)aryl, ($C_{1-6}$alkyl)Het and heterocycle being optionally substituted with $R^{150}$;

l) aryl, Het, ($C_{1-6}$alkyl)aryl or ($C_{1-6}$alkyl)Het, all of which being optionally substituted with $R^{150}$ wherein $R^{150}$ is as defined herein;

or a salt thereof;

wherein said compound is either:
  a) marked with a radioactive isotope at any suitable position;
  b) linked to a detectable moiety by a suitable linker at any suitable position, except $R^1$ and $R^3$; or
  c) linked to an affinity tag at any suitable position, except $R^1$ and $R^3$.

Even more preferably, the probe of the invention is a compound of formula:

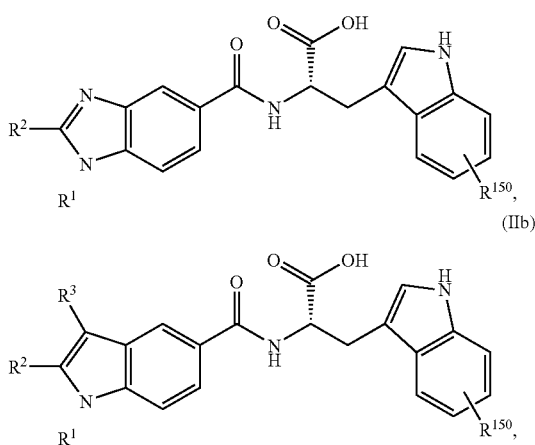

(IIa)

(IIb)

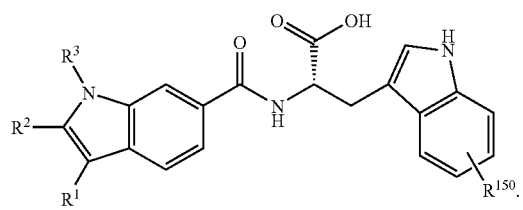

(IIc)

wherein $R^1$ is ($C_{5-6}$)cycloalkyl;

$R^2$ is phenyl, or Het both being optionally substituted with $R^{20}$;

$R^3$ and $R^{150}$ are as defined above;

or a salt thereof;

wherein said compound is optionally:
  a) marked with a radioactive isotope at any suitable position;
  b) linked to a detectable moiety by a suitable linker at any suitable position, except $R^1$ and $R^3$; or
  c) linked to an affinity tag at any suitable position, except $R^1$ and $R^3$.

Specifically, according to a first aspect of the invention, the probe of the present invention is selected from the group consisting of:

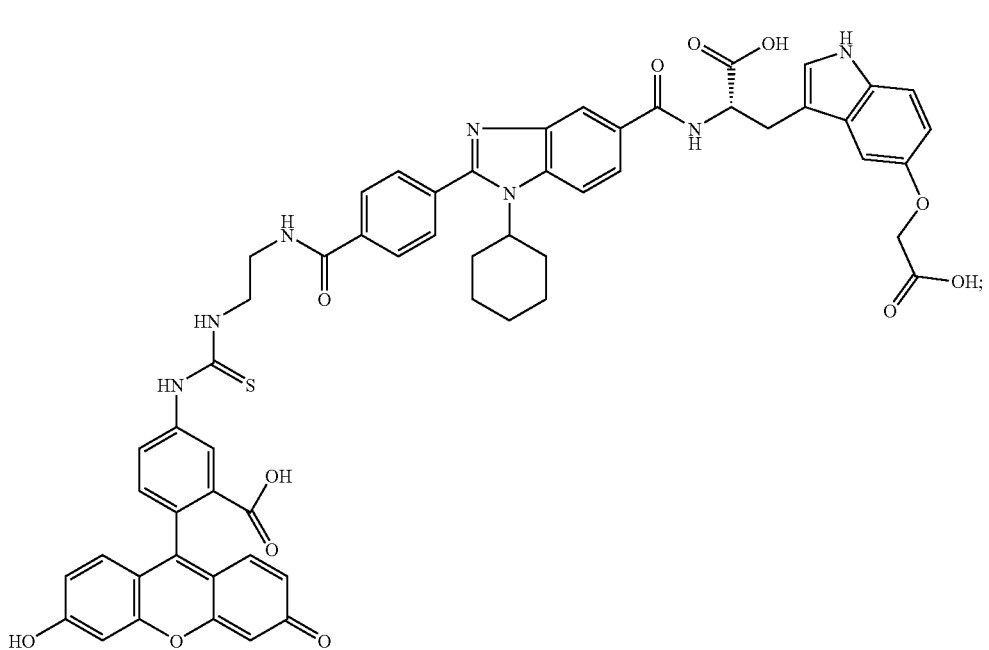

(i)

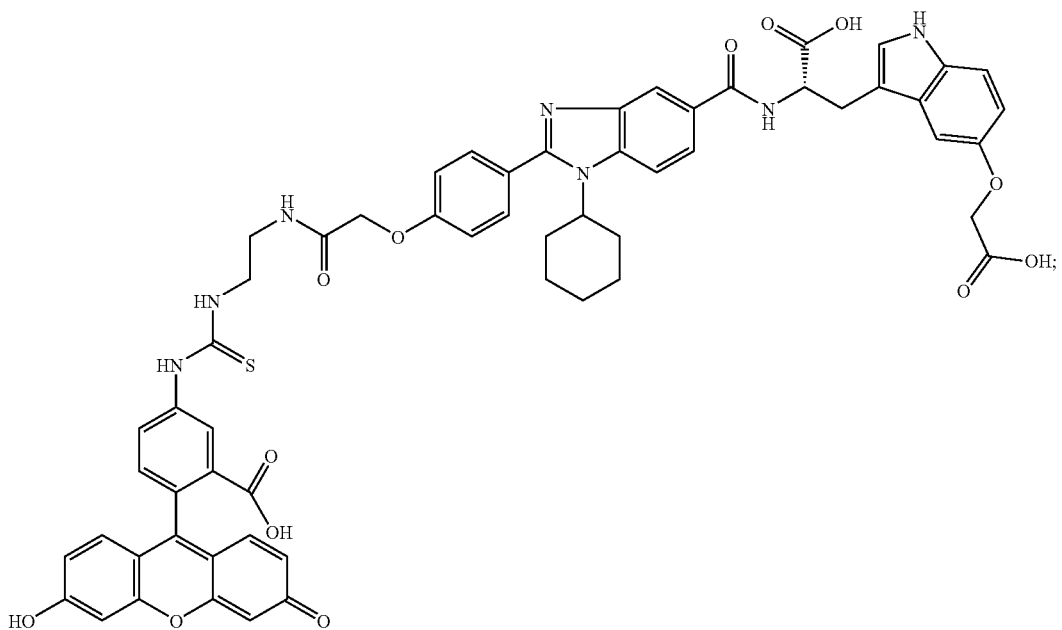
(ii)
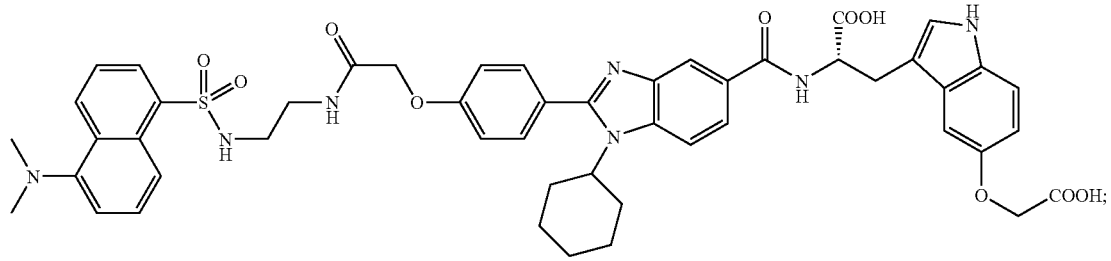
(iii)
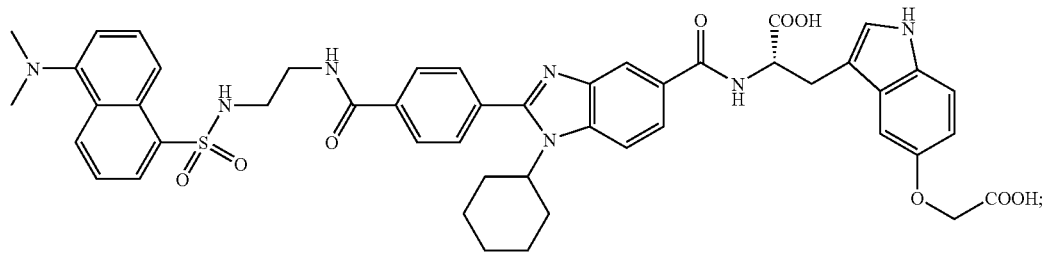
(iv)
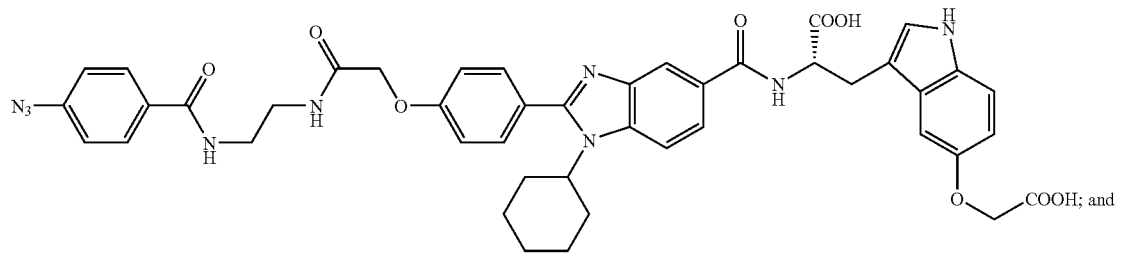
(v)

-continued

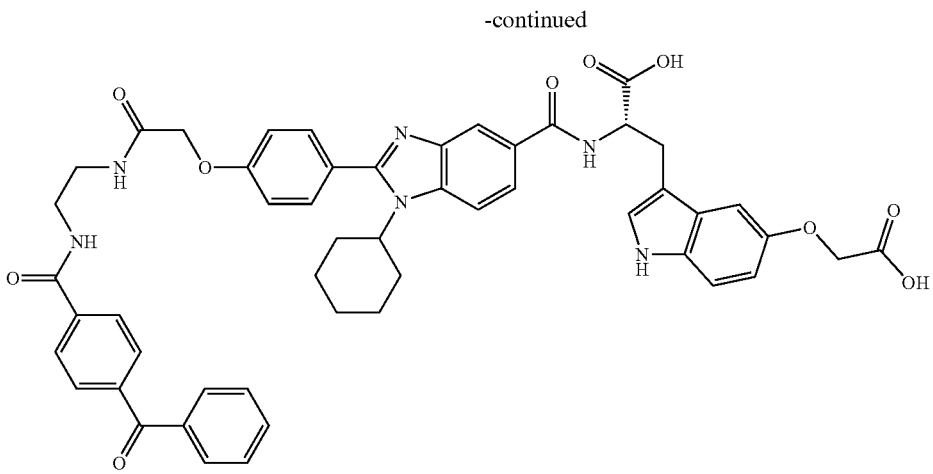

(vi)

According to an alternative aspect of this first embodiment, there is provided a method for identifying compounds that inhibit HCV polymerase comprising the steps of:
a) contacting an HCV polymerase or an analog thereof with a probe of formula I, as defined herein, so as to form a complex having said probe bound to said polymerase;
b) measuring the signal from said complex to establish a base line level;
c) incubating the product of step a) with a test compound; and
d) measuring the signal from said complex; and
e) comparing the signal from step d) with the signal from step b);

whereby a modulation in said signal is an indication that said test compound inhibits said polymerase.

Preferably, the method for identifying compounds capable of inhibiting HCV polymerase, comprises:
f) repeating steps (a) to (e), as defined above in a high throughput screen.

Alternatively, there is provided a probe of formula I:

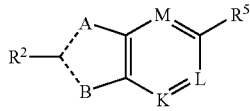

I

A is O, S, NR$^3$, or CR$^3$;
B is NR$^1$ or CR$^1$; with the proviso that, when A is CR$^3$, B is NR$^1$, and when A is O or S, B is CR$^1$;
----- represents either a single or a double bond;
R$^1$ is selected from the group consisting of: (C$_{4-7}$)cycloalkyl optionally substituted with (C$_{1-6}$ alkyl); norbornane, 5-, 6- or 7-membered heterocycle having 1 to 4 heteroatoms selected from O, N, and S, all of which optionally substituted with 1 to 4 substituent selected from the group consisting of:
halo, OH and C$_{1-6}$ alkyl optionally substituted with hydroxy;
R$^2$ is selected from the group consisting of: phenyl, pyridine-N-oxide, 5- or 6-membered aromatic heterocycle having 1 to 4 heteroatoms selected from O, N, and S, and 9- or 10-membered aromatic heterobicycle having 1 to 4 heteroatoms selected from O, N and S;
said phenyl, pyridine-N-oxide, aromatic heterocycle and aromatic heterobicycle being optionally substituted with from 1 to 4 substituents selected from the group consisting of: halogen, C$_{1-6}$ haloalkyl, (C$_{1-6}$)alkyl, C$_{1-6}$ alkoxy, OH, amino optionally mono- or di-substituted with C$_{1-6}$ alkyl;
R$^3$ is selected from the group consisting of: H, (C$_{1-6}$)alkyl, (C$_{1-6}$ alkyl)-(C$_{6-10}$aryl), (C$_{1-6}$ alkyl)-5- or 6-membered heterocycle having 1 to 4 heteroatoms selected from O, N, and S, and 5- or 6-membered heterocycle having 1 to 4 heteroatoms selected from O, N and S,
wherein said aryl and said heterocycle are optionally substituted with from 1 to 4 substituents selected from the group consisting of: COOH, COO(C$_{1-6}$ alkyl), halogen, and (C$_{1-4}$ alkyl);
M is N, CR$^{4a}$, or COR$^{4b}$, wherein R$^{4a}$ is selected from the group consisting of: H, halogen, and (C$_{1-6}$ alkyl); and R$^{4b}$ is selected from the group consisting of: H and (C$_{1-6}$ alkyl);
K and L is each independently N or CR$^6$, wherein R$^6$ is H, halo, C$_{1-6}$ alkyl, OH, or C$_{1-6}$ alkoxy;
R$^5$ is —C(Y)-Z, wherein Y is O or S; and Z is NHR$^{5a}$ or OR$^{5a}$;

wherein:
R$^{5a}$ is selected from the group consisting of: H, (C$_{1-6}$)alkyl, (C$_{2-6}$)alkenyl, (C$_{3-6}$)cycloalkyl optionally substituted with C$_{1-6}$alkyl or C$_{2-6}$alkenyl, (C$_{6-10}$)aryl optionally substituted with C$_{1-6}$alkyl or C$_{2-6}$alkenyl, N-{(C$_{1-6}$)alkyl}$_2$, NHCOO(C$_{1-6}$)alkyl(C$_{6-10}$)aryl, NHCO(C$_{6-10}$)aryl, -5- or 6-atom heterocycle, having 1 to 4 heteroatoms selected from O, N and S, and -9- or 10-atom heterobicycle having 1 to 4 heteroatoms selected from O, N and S;
wherein said alkyl, alkenyl, cycloalkyl, aryl, heterocycle or heterobicycle are all optionally substituted with from 1 to 4 substituents selected from: OH, COOH, (C$_{1-6}$) alkyl, (C$_{2-4}$)alkenyl, (C$_{1-6}$)alkyl-hydroxy, COO(C$_{1-6}$) alkyl, C$_{3-7}$ cycloalkyl, benzyloxy, halogen, (C$_{2-4}$)alkenyl-(C$_{1-6}$)alkyl-COOH, coumarin, (C$_{1-6}$)alkyl-amino, NH(C$_{1-6}$ alkyl), C(halogen)$_3$, —C(O)NH(C$_{1-4}$)alkyl, and —C(O)NH(C$_{6-10}$)aryl, 5- or 6-membered heterocycle having 1 to 4 heteroatoms selected from O, N and S S, 9- or 10-membered heterobicycle having 1 to 4 heteroatoms selected from O, N and S, and 6- or 10-membered aryl;
wherein said alkyl, alkenyl, cycloalkyl, aryl, heterocycle and heterobicycle are all optionally substituted with from 1 to 4 substituents selected from: halogen, OPO$_3$H, sulfonamido, SO$_3$H, SO$_2$CH$_3$, —CONH$_2$, —COCH$_3$, (C$_{1-3}$)alkyl, (C$_{2-4}$alkenyl)COOH, tetrazolyl, COOH, —CONH$_2$, triazolyl, OH, NO$_2$, NH$_2$, —O(C$_{1-6}$ alkyl)COOH, hydantoin, benzoyleneurea, (C$_{1-4}$)alkoxy, cyano, azido, —O—(C$_{1-6}$)alkyl COOH, —O—(C$_{1-6}$)alkyl COO—(C$_{1-6}$)alkyl, NHCO—(C$_{1-6}$alkyl), —NHCOCOOH, —NHCOCONHOH, —NHCOCONH$_2$—NHCOCONHCH$_3$, —NHCO(C$_{1-6}$)alkyl-COOH, —NHCOCONH(C$_{1-6}$) alkyl-COOH, —NHCO(C$_{3-7}$)cycloalkyl-COOH, —NHCONH(C$_{6-10}$)aryl-COOH, —NHCONH (C$_{6-10}$)aryl-COO(C$_{1-6}$)alkyl, —NHCONH(C$_{1-6}$) alkyl-COOH, —NHCONH(C$_{1-6}$)alkyl-COO(C$_{1-6}$) alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$)alkyl COOH, —NH(C$_{1-6}$)alkyl-(C$_{6-10}$)aryl-COOH, —NHCH$_2$COOH, —NHCONH$_2$, —NHCO(C$_{1-6}$) hydroxyalkyl COOH, —OCO(C$_{1-6}$)hydroxyalkyl COOH, (C$_{3-6}$)cycloalkyl COOH,

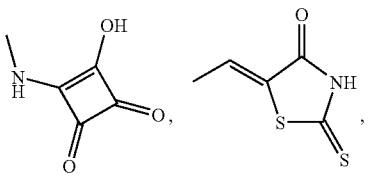

—NHCN, —NHCHO, —NHSO$_2$CH$_3$, —NHSO$_2$CF$_3$; and —O(C$_{1-6}$alkyl)-tetrazol;
or R$^{5a}$ is

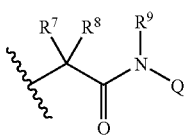

wherein R$^7$ and R$^8$ are each independently H, (C$_{1-6}$ alkyl), (C$_{3-7}$ cycloalkyl), (C$_{1-6}$ alkyl)phenyl, (C$_{1-6}$ alkyl)-(C$_{3-7}$ cycloalkyl), (C$_{3-7}$ cycloalkyl)-(C$_{1-6}$ alkyl), (C$_{3-7}$ cycloalkyl)-(C$_{2-4}$ alkenyl), (C$_{1-6}$ alkyl)-OH, phenyl, CH$_2$biphenyl, 5- or 6-membered heterocycle having from 1 to 4 heteroatoms selected from O, N, and S, 9- or 10-membered heterobicycle having 1 to 4 heteroatoms selected from O, N, and S, (C$_{1-6}$ alkyl)-5- or 6-membered heterocycle having from 1 to 4 heteroatoms selected from O, N, and S, or (C$_{1-6}$ alkyl)-9- or 10-membered heterobicycle having 1 to 4 heteroatoms selected from O, N, and S, or R$^7$ and R$^8$ are covalently bonded together to form (C$_{3-7}$ cycloalkyl), 4-, 5- or 6-membered heterocycle having from 1 to 4 heteroatoms selected from O, N, and S;
or one of R$^7$ or R$^8$ is covalently bonded to R$^9$ to form a pyrrolidine;
wherein said alkyl, cycloalkyl, heterocycle, heterobicycle, phenyl are optionally substituted with from 1 to 4 substituents selected from the group consisting of: OH, COOH, (C$_{1-6}$ alkyl), (C$_{2-4}$ alkenyl), CONH$_2$, NH$_2$, NH(C$_{1-6}$ alkyl), N(C$_{1-6}$ alkyl)$_2$, NHCOCOOH, NHCOCON(C$_{1-6}$ alkyl)$_2$, NHCOCONH(C$_{1-6}$ alkyl), SH, S(C$_{1-6}$ alkyl), NHC(=NH)NH$_2$, halogen, and COO (C$_{1-6}$ alkyl);
R$^9$ is H or (C$_{1-6}$ alkyl); and
Q is selected from the group consisting of: (C$_{1-3}$alkyl) CONHaryl, 6- or 10-membered aryl, biphenyl, 5- or 6-atom heterocycle having 1 to 4 heteroatoms selected from O, N and S, 9- or 10-membered heterobicycle having 1 to 4 heteroatoms selected from O, N and S;
wherein said aryl, biphenyl, heterocycle and heterobicycle are all optionally substituted with from 1 to 4 substituents selected from: OH, COOH, COO(C$_{1-6}$) alkyl, (C$_{1-6}$)alkyl, (C$_{1-6}$)alkylCOOH, (C$_{1-6}$ alkyl)(C$_{2-4}$ alkynyl), (C$_{1-6}$)alkyl-hydroxy, phenyl, benzyloxy, halogen, (C$_{2-4}$)alkenyl, (C$_{2-4}$)alkenyl-(C$_{1-6}$)alkyl-COOH, 5- or 6-membered second heterocycle having 1 to 4 heteroatoms selected from O, N and S, NH-5- or 6-membered second heterocycle having 1 to 4 heteroatoms selected from O, N, and S,
wherein said second heterocycle and phenyl being optionally substituted with from 1 to 4 substituents selected from: (C$_{1-6}$ alkyl), CF$_3$, OH, (C$_{1-6}$alkyl) COOH, O(C$_{1-6}$alkyl)COOH, (C$_{1-6}$alkyl) COO(C$_{1-6}$ alkyl), CH$_2$phenyl, COO(C$_{1-6}$ alkyl), (C$_{1-6}$alkyl)O (C$_{1-6}$alkyl), COOH, NCH(C$_{1-6}$alkyl)$_2$, NCO(C$_{1-6}$ alkyl), NH$_2$, NH(C$_{1-6}$ alkyl), halogen, N(C$_{1-6}$alkyl)$_2$; and C$_{2-6}$ alkenyl-COOH
halogen, OPO$_3$H, benzyl, sulfonamido, SH, SOCH$_3$, SO$_3$H, SO$_2$CH$_3$, S(C$_{1-6}$ alkyl)COOH, —CONH$_2$, —COCH$_3$, (C$_{1-3}$)alkyl, (C$_{2-4}$alkenyl)COOH
wherein said alkenyl is optionally substituted with from 1 to 2 (C$_{1-6}$ alkyl) substituents,
(C$_{2-4}$alkenyl)COO(C$_{1-6}$alkyl), tetrazolyl, COOH, triazolyl, OH, NO$_2$, NH$_2$, —O(C$_{1-6}$ alkyl)COOH, hydantoin, benzoyleneurea, (C$_{1-4}$)alkoxy, (C$_{1-4}$)alkoxy(C$_{1-6}$ alkyl)COOH, cyano, azido, —O—(C$_{1-6}$)alkyl COOH, —O—(C$_{1-6}$)alkyl COO—(C$_{1-6}$)alkyl, —NHCOCOOH, —NHCOCONHOH, —NHCOCONH$_2$, —NHCOCONHCH$_3$, —NHCO(C$_{1-6}$)alkyl-COOH, —NHCOCONH(C$_{1-6}$)alkyl-COOH, —NHCO(C$_{3-7}$) cycloalkyl-COOH, —NHCONH(C$_{6-10}$)aryl-COOH, —NHCONH(C$_{6-10}$)aryl-COO(C$_{1-6}$)alkyl, —NHCONH(C$_{1-6}$)alkyl-COOH, —NHCONH(C$_{1-6}$)alkyl-COO(C$_{1-6}$)alkyl, —NHCONH(C$_{1-6}$)alkyl-(C$_{2-6}$)alkenyl-COOH, —NH(C$_{1-6}$)alkyl-(C$_{6-10}$)aryl-O(C$_{1-6}$) alkyl COOH, —NH(C$_{1-6}$)alkyl-(C$_{6-10}$)aryl-COOH, —NHCH$_2$COOH, —NHCONH$_2$, —NHCO(C$_{1-6}$)hydroxyalkyl COOH, —OCO(C$_{1-6}$)hydroxyalkyl COOH, (C$_{3-6}$)cycloalkyl COOH,

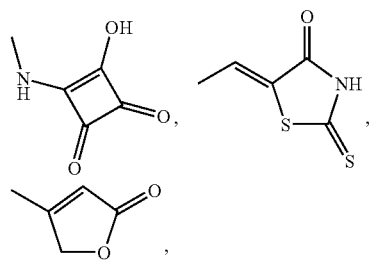

—NHCN, —NHCHO, —NHSO$_2$CH$_3$, —NHSO$_2$CF$_3$, coumarin, (C$_{1-6}$)alkyl-amino, NH(C$_{1-6}$alkyl)$_2$, C(halogen)$_3$, —NH(C$_{2-4}$)acyl, —NH(C$_{6-10}$)aroyl, —CON H(C$_{1-6}$-alkyl), —CO($C_{1-6}$)alkyl-COOH, —CONH($C_{1-6}$)alkyl-COOH, —CO—N H-alanyl, —CONH($C_{2-4}$)alkylN($C_{1-6}$alkyl)$_2$, —CONH($C_{2-4}$)alkyl-Het, —CONH($C_{2-4}$)alkyl-(COOH)-Het, —CONH($C_{1-2}$ alkyl) (OH)($C_{1-2}$ alkyl)OH, —CONH ($C_{1-6}$)alkyl-COOH, —CONH($C_{6-10}$ aryl), —CONH-Het, —CONH($C_{6-10}$)aryl-COOH, —CONH($C_{6-0}$)aryl-COO($C_{1-6}$)alkyl, —CONH($C_{1-6}$)alkyl-COO($C_{1-6}$)alkyl, —CONH($C_{6-10}$)aryl-($C_{1-6}$)alkyl-COOH, and —CONH ($C_{6-10}$)aryl-($C_{2-6}$)alkenyl-COOH;

or a salt thereof;

said probe comprises a detectable label, whereby said probe binds to an HCV polymerase or an analog thereof and is capable of being displaced by an inhibitor thereof.

Labels incorporated into the probe may be paired with appropriate labels attached to the tagged NS5B polymerase such that the close proximity of the two pairs of labels upon probe-polymerase association results in a measurable signal; examples of such detection techniques include, but are not limited to, fluorescence resonance energy transfer (FRET), and time resolved fluorescence (TRF).

Preferably, the detectable label is selected from the group consisting of: a fluorescent label (such as fluorescein, Oregon green, dansyl, rhodamine, Texas-red, phycoerythrin or Eu$^{3=}$), a radioactive atom (such as $^3$H, $^{14}$C, $^{125}$I), a chemiluminescent label (such as luciferase), colorimetric produced by an enzymatic marker (such as β-galactosidase or horseradish peroxidase).

Alternatively, a fluorescent reporter and quencher may be used as pair of labels to monitor association of the probe with the HCV NS5B polymerase. Commonly known reporter/quencher pair may be selected from, for example: EDANS/DABCYL, tryptophan/2,4-dinitrophenyl, tryptophan/DANSYL, 7-methoxycoumarin/2,4-dinitrophenyl, 2-aminobenzoyl/2,4-dinitrophenyl and 2-aminobenzoyl/3-nitrotyrosine.

As will be readily understood by a person skilled in the art, a radioactive label can be incorporated within the probe of formula I at any suitable position. For example, a $^3$H, or $^{14}$C isotope can replace any hydrogen or carbon present in the molecule. Similarly, a $^{125}$I isotope can be substituted on any aromatic ring.

In principle, these tracer methodologies can easily be adapted for the purpose of high-volume screening. Scintillation proximity assay (SPA) methods for radioactive detection have been developed which do not require a separation step and are easily adapted for robotics and microtiter plate format.

Preferably, the detectable label is a fluorescent label or a chemiluminescent label. More preferably, the label is a fluorescent label. Most preferably, the detectable label is a fluorescein.

Non-radioactive detection methods have become increasingly widespread in screening assay because of the costs associated with radiolabeled reagents and their disposal. Fluorescence spectroscopy is one of the most prevalent non-radioactive detection methods. One type of assay in which fluorescence may be used is fluorescence polarization. Polarization is independent of total fluorescence intensity; therefore, this technique may not be as prone to interference as fluorescence amplitude measurements. As disclosed herein, the new type of assay developed uses a fluorescein-labeled inhibitor, though other fluorescent labels or non-fluorescent techniques can also be applied.

Preferably, the polymerase used in the assay may comprise an affinity tag by which the polymerase can be attached to a solid support, and the probe may be labeled so as to provide a detectable signal. An affinity tag incorporated into the probe maybe a biotin that is used to indirectly measure the association of this biotinylated probe to the NS5B polymerase through the secondary use of an avidin-coupled detection technique.

Preferably, the HCV polymerase used in the present assay is selected from the group consisting of: NS5B; NS5BΔ21; NS5BΔ57 or analogs thereof from a variety of genotypes including HCV-1a or 1b strains having optionally a histidine tag at either the N- or C-terminal. Particularly, as will be understood by a person skilled in the art, this binding assay does not require the polymerase activity of the NS5B to be optimal or functional for such a binding assay to perform according to the invention.

EXAMPLES

Probes of formula (I) can generally be synthesized according to the methods described in US 60/216,084; 60/274,374; 60/281,343; PCT CA01/00989; 13/089 filed Jul. 20, 2001 Pierre Louis Beaulieu, Guirez Fazal, George Kukolj, Martin Poirier and Youla Tsantrizos; and 13/090 filed Jul. 25, 2001 Pierre Louis Beaulieu, Guirez Fazal, Sylvie Goulet, George Kukolj, Martin Poirier, Youla Tsantrizos, Eric Jolicoeur, James Gillard and March-Andre Poupart herein incorporated by reference.

Example 1A probe (iii)): (S)-3-(5-Carboxymethoxy-1H-indol-3-yl)-2-({1-[1-cyclohexyl-2-(4-{[2-(5-dimethylamino-naphthalene-1-sulfonylamino)-ethylcarbamoyl]-methoxy}-phenyl)-1H-benzimidazol-5-yl]-methanoyl}-amino)-propionic acid

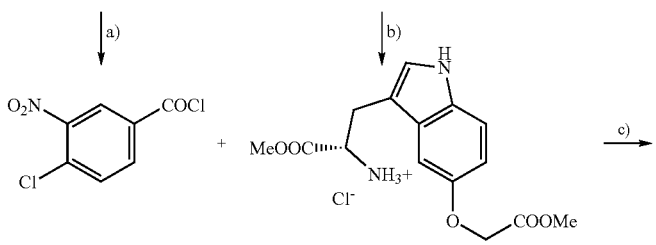

-continued
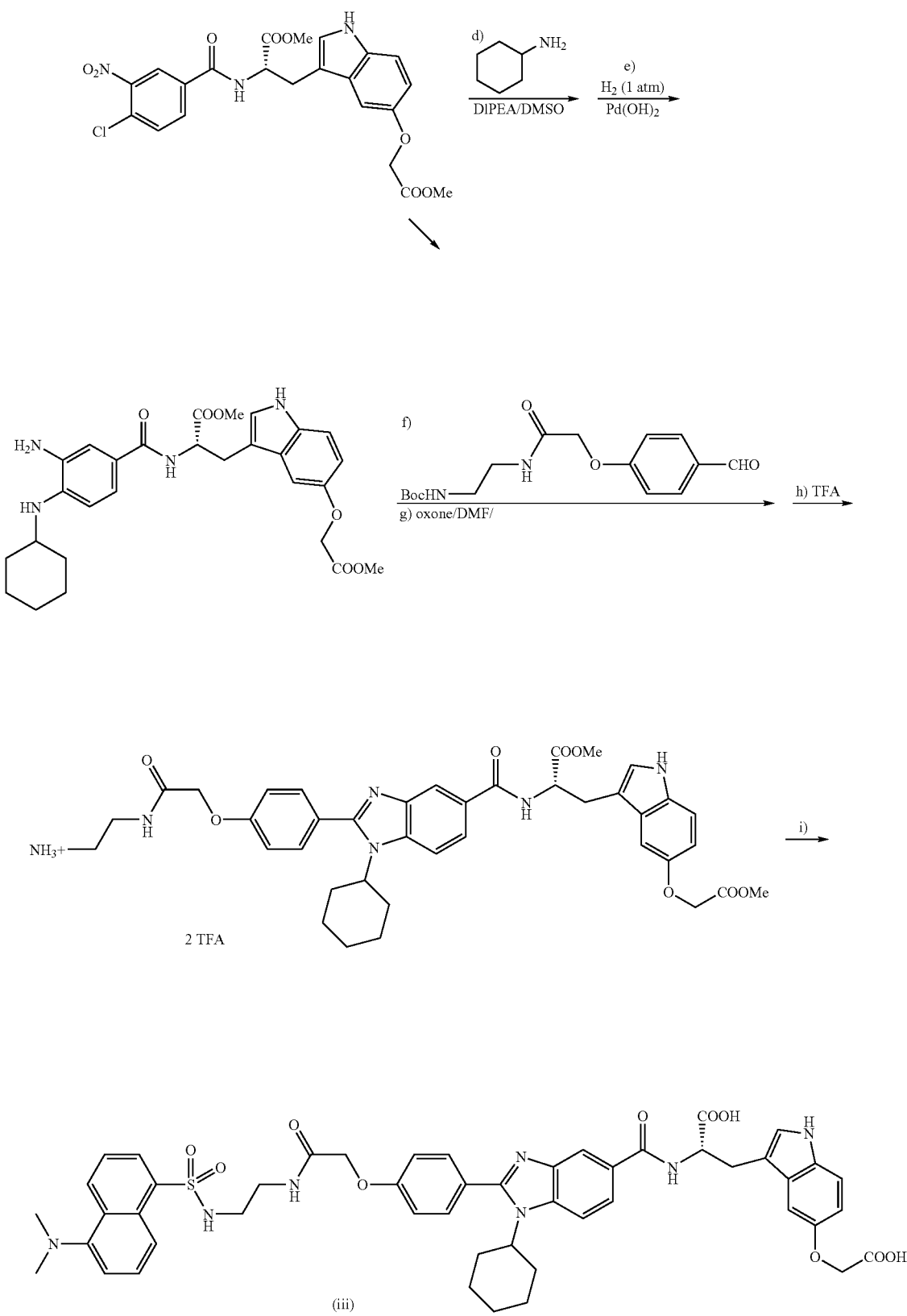

a) 4-Chloro-3-nitrobenzoic acid (40.40 g, 0.20 mole) was suspended in DCM (100 mL) containing 3 drops of DMF. Oxalyl chloride (1.5 equivalents, 0.3 mole, 27 mL) was added in small portions and the mixture stirred overnight at room temperature. After refluxing for an additional hour to complete the reaction, volatiles were removed under reduced pressure and the residue was co-evaporated twice with hexane to give the title compound as a light yellow solid.

b) (S)-5-Hydroxytryptophan methyl ester hydrochloride (1.55 g, 5 mmol) was dissolved in 80% aqueous MeCN (25 mL) and the solution cooled in ice. Sodium bicarbonate (0.850 g, 10 mmol) was added followed by di-telf-butyldicarbonate (1.10 g, 5.1 mmol). The mixture was stirred for 2 h at room temperature, poured into water (200 mL) and extracted with EtOAc (3×). The combined extracts were washed with water and brine, dried (MgSO$_4$) and concentrated to give a beige solid (1.65 g).

The crude product from above (1.50 g, 4.83 mmol) was dissolved in acetone (20 mL) and anhydrous potassium carbonate (1.5 g, 11 mmol) and methyl bromoacetate (0.76 g, 5 mmol) were added. The mixture was reflux for 4 h after which point additional methyl bromoacetate was added to complete the reaction (15 mg portions until complete by HPLC). The reaction mixture was then cooled and filtered to remove solid. Evaporation of the filtrate gave the desired carbamate as an oil (2.0 g).

The crude carbamate from above (2.0 g) was deprotected by stirring with 4N HCl—dioxane for 1 h at room temperature. Removal of volatiles in vacuo gave the desired tryptophan ester derivative as a tan-colored solid (1.51 g).

c) The tryptophan derivative from step b) (0.343 g, 1 mmol) was dissolved in 80% aqueous MeCN (10 mL) and sodium bicarbonate (3 equivalents, 0.260 g) was added. The solution was cooled in ice and 4-chloro-3-nitrobenzoyl chloride from step a) (0.220 g, 1 mmol) was added.The mixture was stirred for one hour at room temperature, concentrated under reduced pressure and the residue purified by flash chromatography (1:2 hexane/EtOAc as eluent) to give compound c) as a yellow foam (0.391 g).

d) The 4-chlorobenzamide derivative from above (0.214 g, 0.45 mmol) was dissolved in DMSO (1 mL) and DIEA (0.2 mL) was added followed by cyclohexylamine (3 equivalents, 0.16 mL). The mixture was stirred at 60-65° C. for 4 h and subsequently diluted with water. The orange precipitate that formed was collected, washed with water and dried (0.200 g).

e) The crude material from above (0.200 g, 0.36 mmol) was hydrogenated (1 atm H$_2$) over 20% Pd(OH)$_2$ on charcoal (60 mg) in MeOH (15 mL). After 2 h, the suspension was filtered to remove the catalyst and concentrated in vacuo to give the title compound as a foam (0.16 g).

f) 4-Formylphenoxyacetic acid (0.306 g, 1.70 mmol) was dissolved in DCM (5 mL). DIEA (0.524 g, 4 mmol) and TBTU (0.550 g, 1.70 mmol) were added followed by tert-butyl N-(2-aminoethyl)carbamate (0.250 g, 1.56 mmol). The mixture was stirred 2 h at room temperature, dissolved in EtOAc and washed sequentially with 5% aqueous K$_2$CO$_3$, KHSO$_4$, water and brine. The extract was dried (MgSO$_4$) and concentrated under reduced pressure to give a yellow solid (0.350 g).

g) The diamine derivative from step e) (0.026 g, 0.05 mmol) and aldehyde from step f) (0.020 g, 0.06 mmol) were dissolved in DMF (0.3 mL) and water (0.03 mL) was added followed by oxone®) (0.024 g, 0.04 mmol). The mixture was stirred 1 h at room temperature and then diluted with water. The resulting precipitate was collected by filtration, washed with water and dried to give a beige solid (0.020 g).

h) The crude carbamate from above was stirred with TFA for 30 min at room temperature. Volatiles were removed under reduced pressure and the residue was purified by preparative C$_{1-8}$ reversed-phase HPLC to give the bis TFA salt.

i) The amine salt (0.019 g, 0.02 mmol) was dissolved in DMSO (0.3 mL) and DIEA (0.06 mL) was added followed by dansyl chloride (0.065 g, 0.02 mmol). The mixture was stirred for 1 h at room temperature. 5N NaOH (0.12 mL) and water (0.05 mL) were added and the saponification was allowed to proceed for 1 h at room temperature. Following acidification with TFA, the probe (iii) was directly isolated from the reaction mixture by preparative C$_{1-8}$ reversed-phase HPLC: MS (ES+) m/z 930 (MH+).

Example 1B probe (ii):5-(3-{2-[2-(4-{5-[(S)-1-Carboxy-2-(5-carboxymethoxy-1-H-indol-3-yl)-ethylcarbamoyl]-1-cyclohexyl-1H-benzimidazol-2-yl}-phenoxy)-ethanoylamino]-ethyl}-thioureido)-2-(6-hydroxy-3-oxo-3H-xanthen-9-yl)-benzoic acid

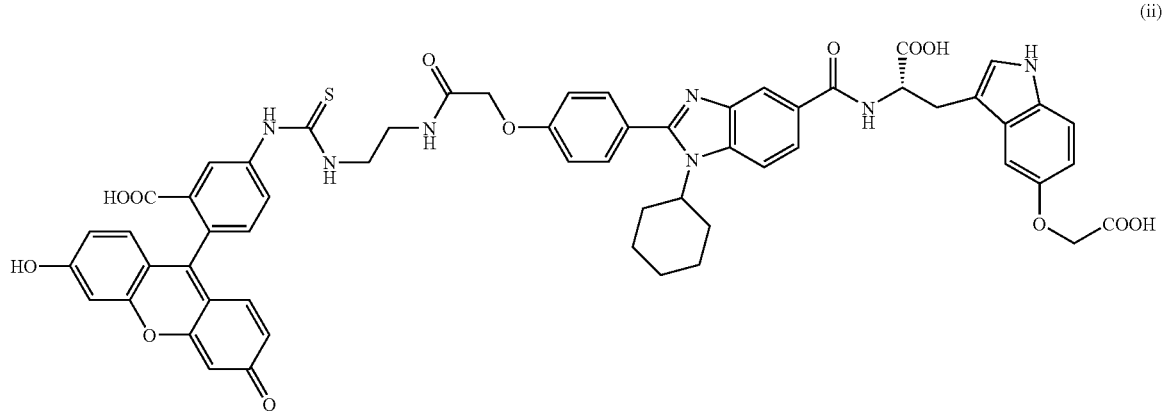

(ii)

The amine salt from step h) of Example 1A (0.06 mmol) was dissolved in DMSO (0.6 mL) and DIEA (0.3 mL) was added followed by fluorescein isothiocyanate isomer 1 (0.026 g, 0.066 mmol). The mixture was stirred for 1 h at room temperature. 5N NaOH (0.3 mL) and water (0.15 mL) were added and stirring resumed for an additional 30 min. Following acidification with TFA, probe (ii) was isolated directly by preparative $C_{1-8}$ reversed-phase HPLC: MS (ES+) m/z 1086 (MH+).

Example 1C probe (v): (S)-2-{[1-(2-{4-[(2-{[1-(4-Azido-phenyl)-methanoyl]-amino}-ethylcarbamoyl)-methoxy]-phenyl}-1-cyclohexyl-1H-benzoimidazol-5-yl)-methanoyl]-amino}-3-(5-carboxymethoxy-1H-indol-3-yl)-propionic acid a yellow solid (0.257 g). The crude carbamate (0.257 g, 0.84 mmol) was deprotected by stirring in 4N HCl—dioxane (15 mL) for 2 h at room temperature. Volatiles were removed under reduced pressure to give a pinkish solid.

b) 4-Formylphenoxyacetic acid (0.200 g, 1.1 mmol) was dissolved in DCM (3 mL) and DIEA (0.5 mL) was added followed by TBTU (0.350 g, 1,1 mmol) and the amine salt from above (0.240 g, 1 mmol). The mixture was stirred 4 h at room temperature, dissolved in EtOAc and washed sequentially with 5% aqueous $K_2CO_3$, $KHSO_4$, water and brine. The extract was dried ($MgSO_4$) and concentrated under reduced pressure to give an off-white solid (0.162 g).

c) The benzaldehyde derivative from above (0.044 g, 0.12 mmol) and the diamine derivative from step e) of

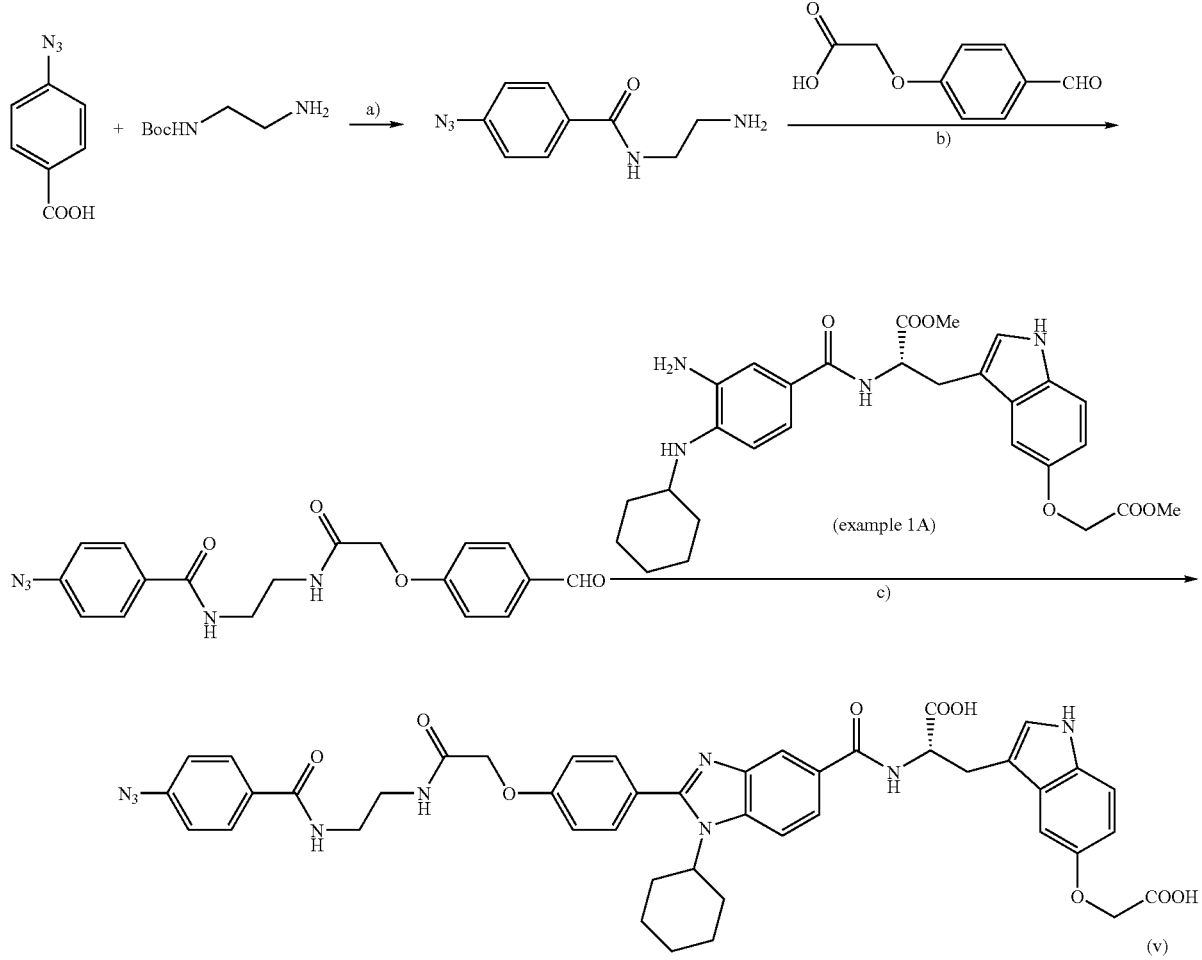

a) 4-Azidobenzoic acid (0.160 g, 1 mmol) was dissolved in DCM (3 mL). DIEA (0.5 mL, 2.5 mmol) and TBTU (0.337 g, 1.05 mmol) were added followed by tert-butyl N-(2-aminoethyl)carbamate (0.165 g, 1.03 mmol). The mixture was stirred 2.5 h at room temperature, dissolved in EtOAc and washed sequentially with 5% aqueous $K_2CO_3$, $KHSO_4$, water and brine. The extract was dried ($MgSO_4$) and concentrated under reduced pressure to give Example 1A (0.052 g, 0.1 mmol) were dissolved in DMF (0.6 mL) and water (0.1 mL). Oxone® (0.050 g, 0.8 mmol) was added and the mixture stirred for 1 h at room temperature. 5N NaOH (0.2 mL) and water (0.1 mL) were added and saponification allowed to proceed for 1 h. Probe (v) was isolated directly by preparative $C_{1-8}$ reversed-phase HPLC (12.5 mg): MS (ES+) m/z 842 (MH+).

Example 1D probe (vi): (S)-3-(5-Carboxymethoxy-1H-indol-3-yl)-2-{(1-[1-cyclohexyl-2-(4-{[2-({1-[4-(1-phenyl-methanoyl)-phenyl]-methanoyl}-amino)-ethylcarbamoyl]-methoxy}-phenyl)-1H-benzoimidazol-5-yl]-methanoyl}-amino)-propionic acid

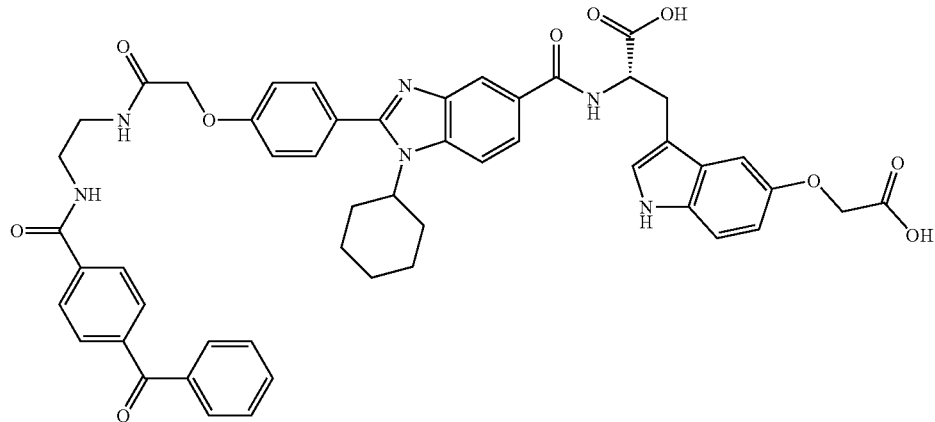
(vi)

Following the procedures described for probe (v) in Example 1C but using 4-benzoylbenzoic acid instead of 4-azidobenzoic acid, probe (vi) was obtained: MS (ES+) m/z 905 (MH+).

Example 1E

Probe (iv) (S)-3-(5-Carboxymethoxy-1H-indol-3-yl)-2-{[1-(1-cyclohexyl-2-{4-[2-(5-dimethylamino-naphthalene-1-sulfonylamino)-ethylcarbamoyl]-phenyl}- 1H-benzimidazol-5-yl)-methanoyl]-amino}-propionic acid

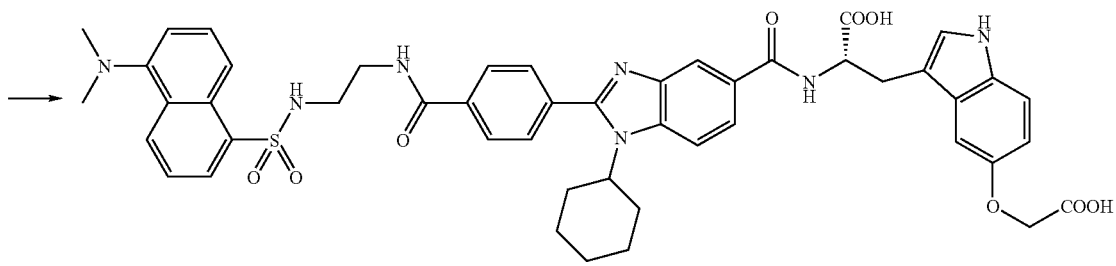
(iv)

a) Following the procedures described for step f) in Example 1A, 4-carboxybenzaldehyde was coupled to tert-butyl N-(2-aminoethyl)carbamate.
b) Following benzimidazole ring formation with the diamine derivative of Example 1A step e) and the aldehyde from above using oxone® as described in Example 1A step g), the Boc protecting group was removed and the resulting amine condensed with dansyl chloride as described in Example 1A step i).
c) Probe (iv) was obtained following saponification of the ester groups under the usual conditions and isolation by preparative $C_{1-8}$ reversed-phase HPLC: MS (ES+) m/z 900 (MH+).

Example 1F (Probe (i):5-[3-(2-{[1-(4-{5-[(S)-1-Carboxy-2-(5-carboxymethoxy-1-H-indol-3-yl)-ethylcarbamoyl]-1-cyclohexyl-1H-benzimidazol-2-yl}-phenyl)-methanoyl]-amino}-ethyl)-thioureido]-2-(6-hydroxy-3-oxo-3H-xanthen-9-yl)-benzoic acid

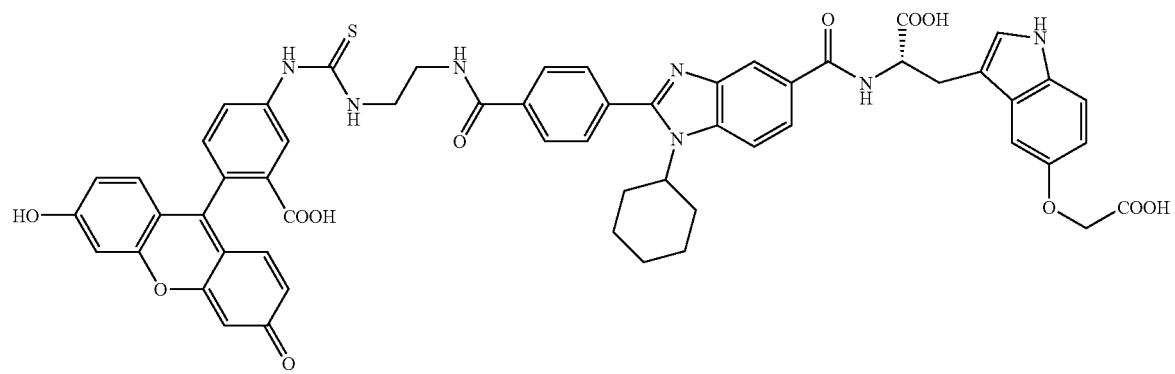

(i)

The procedure described for Example 1E) was used except that fluorescein isothiocyanate isomer 1 was used instead of dansyl chloride. Probe (i) was obtained after purification by preparative $C_{1-8}$ reversed-phase HPLC: MS (ES+) m/z 1056 (MH+).

Example 2

Production and Purification of HCV NS5B polymerase Δ21-His

The recombinant HCV NS5B polymerase can be produced in soluble form by expression of a variant that lacks the C-terminal 21 amino acids normally found on the mature NS5B (Yamashita et al. 1998, J. Biol. Chem. 273:15479-15486; Ferrari et al., 1999, J. Virol. 73: 1649-1654). We have expressed this so called NS5BΔ21 with a C-terminal hexa-histidine (termed NS5BΔ21-His; SEQ ID. NO. 1) and with an N-terminal hexa-histidine tag (termed His-NS5BΔ21; SEQ ID NO. 2) (either proteins being referred to as "his-tag NS5B"). Expression of these genes from pET vectors in *E. coli* strain JM109 (DE3) is induced with 0.4 mM IPTG for 3 hours at 22° C. Cells are harvested and lysed in a microfluidizer in lysis buffer (Tris-HCl pH 7.5, 10% glycerol, 1 mM EDTA, 2 mM 2-mercaptoethanol, 500 mM NaCl, 1 mM PMSF, 1 μg/ml antipain, 1 μg/ml pepstatin A and 1 μg/ml leupeptin). The lysate is clarified by a 30 000 g centrifugation and then supplemented with imidazole to final concentration of 10 mM. The lysate is then loaded onto a metal-chelating resin (Ni-NTA; Qiagen) previously equilibrated with buffer A (Tris-HCl pH 7.5, 10% glycerol, 500 mM NaCl, 10 mM imidazole), washed extensively and then the protein is eluted with gradient of buffer A containing 500 mM imidazole. Peak fractions containing the his-tag NS5BΔ21 are pooled and diluted with buffer C (20 mM Tris-HCl pH 7.5, 10% glycerol, 5 mM DTT) to reduce the NaCl concentration to 300 mM and then applied to a DEAE-Sepharose column to remove any nucleic acid. The flow-through from the DEAE-Sepharose column is diluted with buffer C to reduce the NaCl to 200 mM and then applied to a heparin-Sepharose column. The his-tag NS5B is eluted from the heparin-Sepharose in buffer C with a 200 mM to 1 M NaCl gradient. Peak fractions containing the his-tag NS5B are pooled and diluted with buffer C to achieve a final NaCl of 200 mM and loaded onto a Resource S column. Concentrated His-tag NS5B is eluted from the resource S, loaded and size fractionated on a Superdex 200 column in buffer C containing 300 mM NaCl. Peak fractions contain highly pure his-tag NS5B and are stored at −80° C. until use.

Example 3

Fluorescence Anisotropy Analysis

Figure 1:
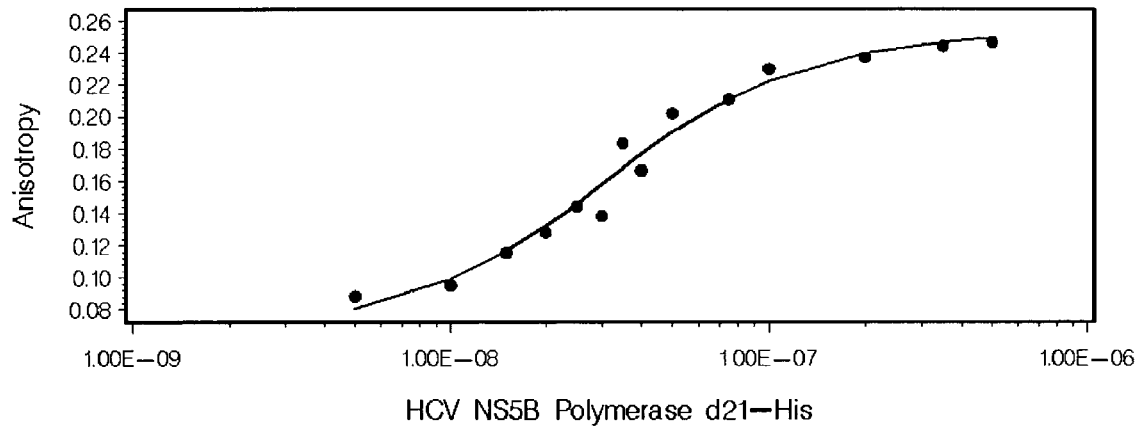
FIG. 1 illustrates the titration of probe (i) with the NS5BΔ21-His polymerase. Standard conditions for the Fluorescence anisotropy analysis are described in Example 3. The determined $K_d$ value of probe (i) for this polymerase is 12.6 nM.

Titration of the probe with the enzyme was performed as follows:

The fluorescein labeled probe was diluted to the desired concentration in 20 mM Tris-HCl pH 7.5, 1 mM EDTA, 5 mM MgCl$_2$, 1 mM DTT and 10% DMSO. The NS5BΔ21-His protein was serially diluted in 25 mM Tris-HCl pH 7.5, 300 mM NaCl, 5 mM DTT, 1 mM EDTA, 30% glycerol and 0.1% IGEPAL. Total volume of the reaction was 500 μL and final assay buffer was 20 mM Tris-HCl pH 7.5, 1 mM EDTA, 5 mM MgCl$_2$, 1 mM DTT, 30 mM NaCl, 3% glycerol, 0.01% IGEPAL and 5% DMSO. Anisotropy measurements were performed on a SLM Aminco 8100 Spectrofluorometer equipped with a 450-W xenon arc lamp and a T-optics configuration. Excitation wavelength was at 493 nm and emission was monitored at 530 nm. In each anisotropy measurement, the parallel and perpendicular intensities of the background buffer solution was subtracted from the measured values of the sample and the anisotropy was calculated. Data were processed on SAS program (SAS Institute Inc., NC, USA) for a non linear regression to obtain the direct binding equilibrium constant and other parameters, and the plot of the regressed fit over the experimental data. An example of a titration curve obtained with probe (i) is shown on FIG. 1. $K_d$ values for probes (i) and (ii) with the polymerase were respectively of 15 nM and 6 nM.

Example 4

96-Well Plate Polarization Assay

To obtain $K_d$ values of different compounds competing with these probes (test compounds), this assay was transformed to a more amenable format and a binding assay was made suitable for a 96-well microplate reader. The probe was diluted in order to obtain the desired final concentration (from 4 to 25 nM, depending on its $K_d$ towards the enzyme and on the conditions of the assay). The tested compounds were serially diluted by a factor of 2 or 3-fold in 20 mM Tris-HCL pH 7.5, 1 mM EDTA, 5 mM $MgCl_2$, 1 mM DTT and 15% DMSO. The NS5BΔ21-His concentration in the assay was calculated to obtain 70% of binding of the probe; these conditions allowed for the displacement of the probe by test compounds. The assay reactions finally contained 50 μL of the serial dilutions of the tested compounds that were transferred in 96-well black plates (Packard); a complete row was however free of compound to obtain a positive control value and verify real percent of bound probe in the experiment. 50 μL of the probe were then added to each well, except in one column for blank subtraction. Lastly, 150 μL of enzyme were added to all wells, except in one row, which was used to determine the 0% and 100% bound values. In this row of 8 wells, enzyme buffer was added to the first 4 wells (to determine the anisotropy value of the free probe or $r_f$) and a 10-fold excess of the concentration of the enzyme used in the assay was added to the other 4 wells (to determine the anisotropy value when 100% of the probe is bound i.e. the $r_b$ value). These values were required to calculate the $K_d$ values. The final buffer conditions of the assay were identical to the ones used for $K_d$ determination of the probes, i.e. 20 mM Tris-HCl pH 7.5, 1 mM EDTA, 5 mM $MgCl_2$, 1 mM DTT, 30 mM NaCl, 3% glycerol, 0.01% IGEPAL and 5% DMSO. The reactions were incubated for 90 minutes at room temperature in the dark. Readings of polarization were then performed on a POLARstar Galaxy, equipped with a high-energy xenon flash lamp, using an excitation filter of 485 nm and an emission filter of 520 nm. Polarization values can be converted easily to anisotropy values with the following calculation (Owicki et al., 2000, J. Biomol. Screen. 5:297-306):

$$a = 2 \times P/(3-P) \text{ where}$$

a: anisotropy value
P: Polarization value

Figure 2:
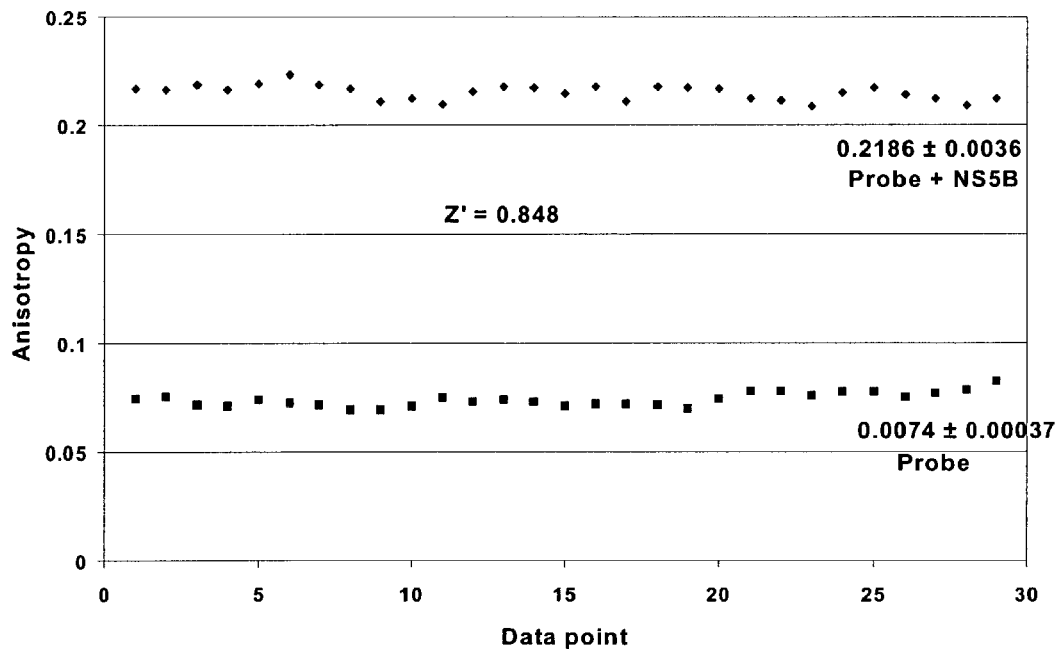
FIG. 2 illustrates Z' evaluation for the Fluorescence Polarization assay. A series of positive and negative controls were tested in the 96-well plate polarization assay, using the standard conditions, to determine the standard deviation (SD) of both controls. The Z' value was then obtained from the following calculation.

Anisotropy values can then be used to obtain two types of results fitted to SAS nonlinear regression analysis to obtain apparent $K_d$ values, using for the calculations as positive control the anisotropy value at ~70% binding, and as negative control the anisotropy value of the free probe ($r_f$); fitted to the Anisotropy equation:

$$a = \frac{(-K_d - I + E_o) + \sqrt{((K_d + I - E_o)^2 + 4 * K_d * E_o)}}{2 \left[ \frac{(a * Q * r_b + K_p * r_f)}{(K_p + a * Q)} \right]}$$

where a: anisotropy
$K_d$: dissociation constant for the inhibitor
I: Concentration of compound (or inhibitor) tested
$E_o$: NS5B concentration ($E_o$ has to be >>[probe])
$Q = Q_b/Q_f$ = total fluorescence for probe 100% bound/total fluorescence for free probe
$r_b$: anisotropy value when the probe is 100% bound
$r_f$: anisotropy value when the probe is free
$K_p$: dissociation constant for the probe This high throughput assay was evaluated and validated by the determination of the statistical parameter Z' (J.-H. Zhang et al., 1999, J. of Biomol. Screening, 4:67-73). Results of this experiment are illustrated on FIG. 2. The anisotropy values for a series of positive and negative controls were very similar, resulting in very low standard deviations; 0.2186±0.0036 A units for the positive controls and 0.0738±0.0037 A units for the negative controls. The Z' value obtained for the assay was of 0.85, implying that we have excellent conditions to detect compounds that would compete with the probe.

Example 5

Inhibitor Testing

We have identified potent compounds that can effectively displace the probe in this binding assay. FIGS. 3 and 4 show examples of some of them, with $K_d$ values ranging from 31 nM to 1 μM. The anisotropy equation was defined in the Grafit Software (Erithacus Software Ltd., UK) and plotted such that inhibitor concentration was the X-variable and anisotropy was the Y variable; parameters calculated by the software were the inhibitor $K_d$ and $Q_b/Q_f$ ratio. Supplied constants were the $K_p$, $E_O$, $r_b$ and $r_f$.

Example 6

Modified Conditions for the Polarization Assay

Figure 5:
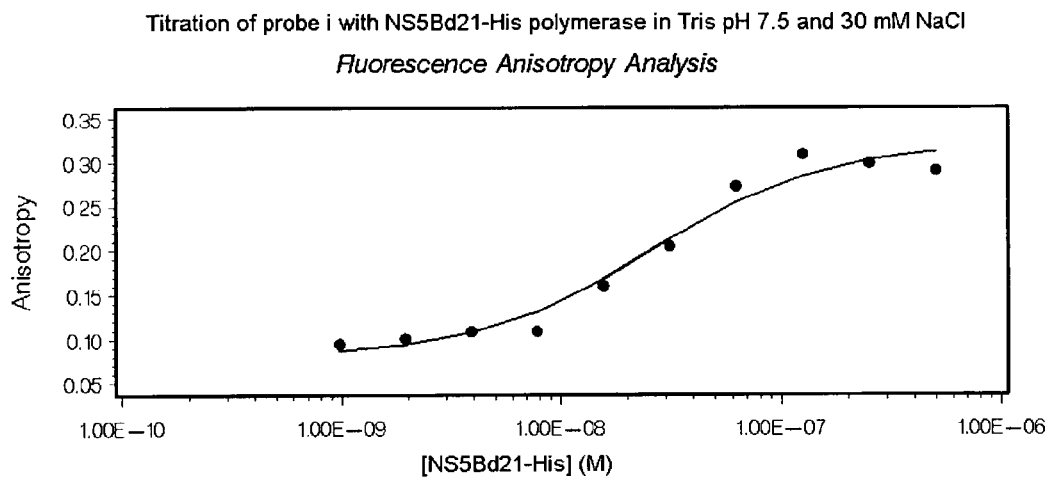
Figure 6:
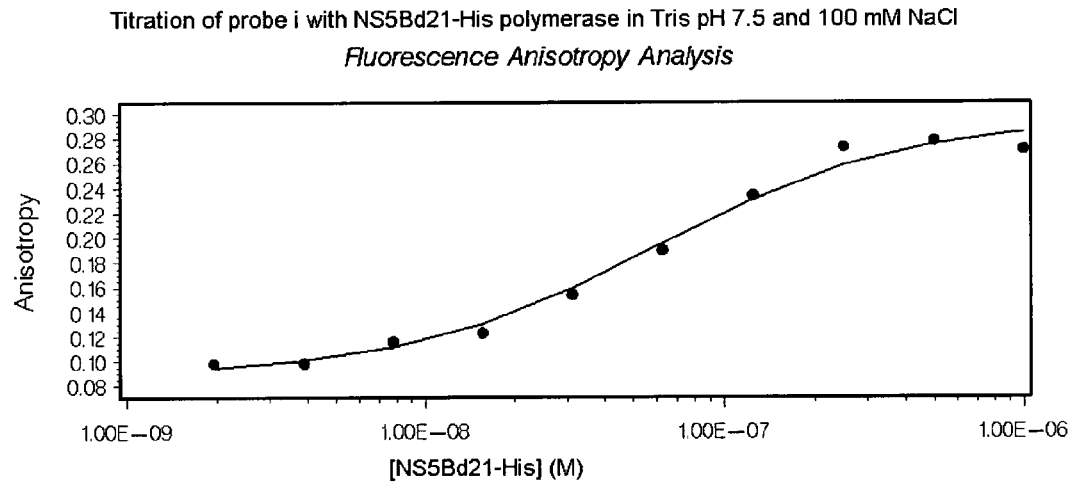
Figure 7:
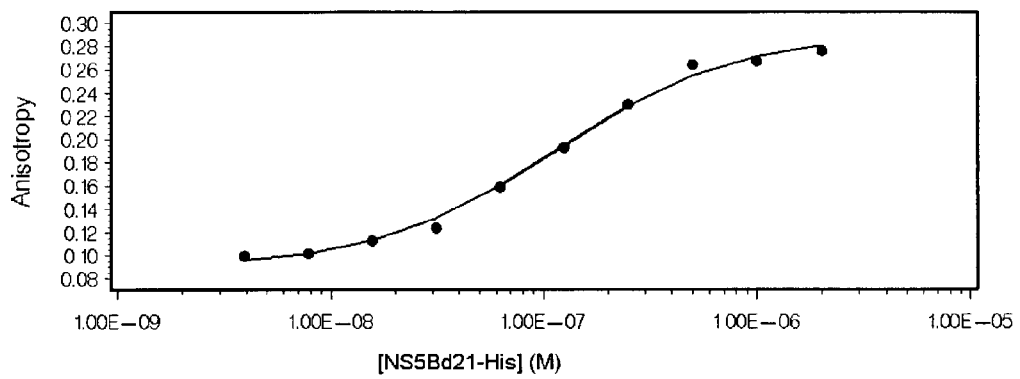
Figure 8:
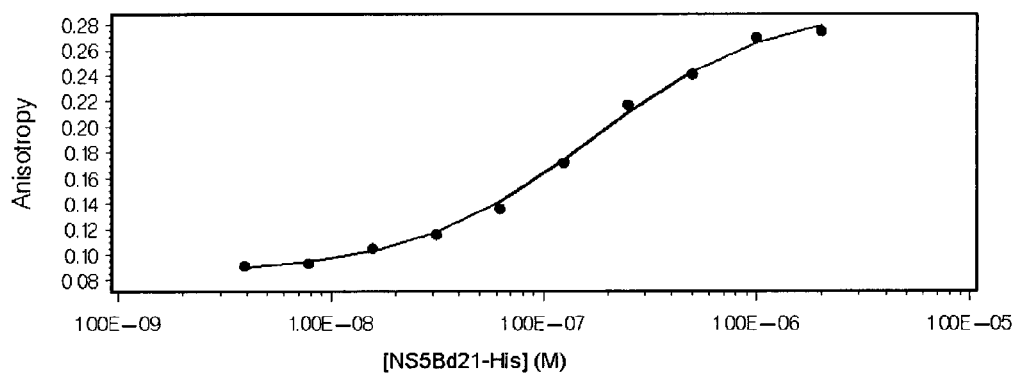

The usefulness of this polarization assay is evident when binding of compounds has to be studied under different conditions. For example, binding constants of the probes have been determined at different concentrations of salts and pH. FIGS. 5 to 8 show the binding curves of probe (i) in final NaCl concentrations ranging from 30 mM to 200 mM. FIG. 5 shows the NaCl concentration at 30 mM. FIG. 6 shows the NaCl concentration at 100 mM. FIG. 7 shows the NaCl concentration at 150 mM. FIG. 8 shows the NaCl concentration at 200 mM. All other reagents in the assay were as described in the standard protocol (Example 3). As shown on these Figures, $K_d$ values gradually increase with salt concentration from $K_d$=15 nM (at 30 mM NaCl) to $K_d$=122 nM (at 200 mM NaCl). Studies at pH 6.5 were also performed to determine the $K_d$ of the probe (i) at lower pH. For these assays, 20 mM Phosphate buffer pH 6.5 was used in place of Tris; all other reagents of the assay were as described in the 96-well Polarization assay (Example 4). An example of these types of experiments is shown in FIG. 9. The $K_d$ value obtained at pH 6.5 with probe (i) was of 33 nM. Having established these $K_d$ values under different experimental conditions, it is then trivial to determine what concentrations of probe and enzyme should be used to obtain 70% of binding of the probe with the equilibrium equation. Once these values are obtained, compounds of interest can easily be studied under the new conditions to determine their $K_d$ values.

Example 7

Fluorescence Polarization Assay With a Modified Enzyme

The Fluorescence polarization assay was also used with other constructs of our HCV polymerase enzyme. In addition to the C-terminally tagged NS5BΔ21-His polymerase, the NS5B enzyme with the His-tag at the N-terminal position was also used in the fluorescence polarization assay. Determination of the $K_d$ for the probe (i) with this enzyme was performed, using the same conditions described in the standard 96-well format assay. FIG. 10 shows that the $K_d$ obtained with probe (i) was similar, i.e. 18 nM. A comparison was made between the $IC_{50}$ and the $K_d$ for three compounds, using these two different constructs of the enzymes (NS5BΔ21-His and His-NS5BΔ21).

$IC_{50}$'s are determined using the Scintillation Proximity Assay (SPA) according to the following assay:

The substrates are: (i) a 12 nucleotide RNA oligo-uridylate (or oligo-uridine-monophosphate) (oligo-U) primer modified with biotin at the free 5° C. position; (ii) a complementary poly-adenylate (or adenosine monophospahte) (polyA) template of heterogeneous length (1000-10000 nucleotides); and (iii) UTP-[5,6 $^3$H]. Polymerase activity is measured as the incorporation of UMP-[5,6 $^3$H] into the chain elongated from the oligo-U primer. The $^3$H-labelled reaction product is captured by SPA-beads coated with streptavidin and quantified on the TopCount (Packard). Inhibitors are tested at various concentrations in a reaction containing: 1 to 5 nM of the his-tagged NS5B, 1 μg/ml of biotinylated oligo U primer, 10 μg/ml of polyA template, 20 mM Tris-HCl pH 7.5, 5 mM MgCl$_2$, 25 mM KCl, 1 mM EDTA, 1 mM DTT, 0.33% n-dodecyl maltoside, 5% DMSO, 0.0083 μCi/μl [0.25 μM] UTP-[5,6-$^3$H], 0.75 μUTP, 1.67 μl RNAsin™. The reaction was incubated at room temperature for 1.5 hours. STOP solution (20 μl; 0.5 M EDTA, 150 ng/μl tRNA) was added, followed by 30 μl streptavidin coated PVT beads (8 mg/ml in 20 mM Tris-HCl, pH 7.5, 25 mM KCl, 0.025% NaN$_3$). The plate was then shaken for 30 minutes. A solution of CsCl was added (70 μl, 5 M), to bring the CsCl concentration to 1.95 M. The mixture was then allowed to stand for 1 hour. The beads were then counted on a Hewlett Packard TopCount™ instrument. Based on the results at ten different concentrations of test compound, standard concentration-% inhibition curves were plotted and analysed to determine $IC_{50}$'s for the compounds.

Results of this experiment are illustrated in Table I. The $K_d$ values were similar with both enzymes for the three compounds tested, whereas the $IC_{50}$ values obtained with the two enzymes show significant differences and reflect the differences in substrate affinity.

Example 8

Specificity of the Fluorescence Polarization Assay

The utility of the Fluorescence polarization assay was examined with another distantly related viral polymerase and with a closely related genotype (1a) HCV polymerase.

The GBV-B polymerase enzyme (termed GBV-BΔ23-His; SEQ ID NO. 3) (Simons, J. N. et al., 1995, Proc. Natl. Acad. Sci. USA 92, 3401-3405; Bukh, J. et al., 1999, Virology 262, 470-478) was produced and purified as described in Example 2 with the following modifications:

Expression of the gene from pET vectors in *E. coli* strain JM109 (DE3) was induced with 0.5 mM IPTG for 3 hours at 22° C. Cells were harvested and lysed in a microfluidizer in buffer A (Tris-HCl pH 7.5, 10% glycerol, 1 mM EDTA, 2 mM 2-mercaptoethanol, 500 mM NaCl, 1 mM PMSF, 1 ug/ml antipain, 1 ug/ml pepstatin A, 1 ug/ml leupeptin and 0.5% dodecyl-β-D-maltoside). The lysate was clarified by a 30 000 g centrifugation and then supplemented with imidazole to a final concentration of 10 mM. The lysate was then loaded onto a metal-chelating resin (Ni-NTA; Qiagen) previously equilibrated with buffer A containing 10 mM imidazole, washed extensively and then the protein was eluted with a gradient of buffer A containing 500 mM imidazole. Peak fractions containing the his-tag GBV-BΔ23 were pooled and diluted with buffer C (20 mM Tris-HCl pH 7.5, 10% glycerol, 5 mM DTT, 0.01% dodecyl-β-D-maltoside) to reduce the NaCl concentration to 300 mM and then applied to a DEAE-Speharose column to remove any nucleic acid. The flow-through from the DEAE-Speharose column was diluted with buffer C to reduce the NaCl to 200 mM and then applied to a heparin-Sepharose column. The his-tag GBV-B was eluted from the heparin-Sepharose in buffer C with a 200 mM to 1 M NaCl gradient. Peak fractions containing the pure his-tag GBV-B were then pooled and stored at −80° C. until use.

The HCV genotype 1a NS5B polymerase [termed His-NS5BΔ21 (H77c, 1a); SEQ ID NO. 4] (Yanagi, M. et al., 1997, Proc. Natl. Acad. Sci. USA 94, 8738-8743) was produced and purified as described in Example 2 with the following modifications:

Expression of the gene from pET vectors in *E. coli* strain JM109 (DE3) was induced with 0.4 mM IPTG for 3 hours at 22° C. Cells were harvested and lysed in a microfluidizer in buffer A (Tris-HCl pH 8.0, 10% glycerol, 1 mM EDTA, 2 mM 2-mercaptoethanol, 500 mM NaCl, 1 mM PMSF, 1 ug/ml antipain, 1 ug/ml pepstatin A, 1 ug/ml leupeptin, 1% dodecyl-β-D-maltoside, 1% Triton X-100 and 0.1% CHAPS). The lysate was clarified by a 30 000 g centrifugation and then supplemented with imidazole to a final concentration of 10 mM. The lysate was then loaded onto a metal-chelating resin (Ni-NTA; Qiagen) previously equilibrated with buffer A containing 10 mM imidazole, 0.1% NP-40, without CHAPS, and with lower concentrations of the other detergents (0.2% dodecyl-β-D-maltoside, 0.05% Triton X-100); after extensive washing, the protein was eluted with a gradient of buffer A containing 500 mM imidazole. Peak fractions containing the his-tag NS5BΔ21 (H77c, 1a) were pooled and diluted with buffer C (20 mM Tris-HCl pH 8.0, 10% glycerol, 5 mM DTT, 0.2% dodecyl-β-D-maltoside) to reduce the NaCl concentration to 300 mM and then applied to a DEAE-Sepharose column to remove any nucleic acid. The flow-through from the DEAE-Sepharose column was diluted with buffer C to reduce the NaCl to 200 mM and then applied to a heparin-Sepharose column. The his-tag NS5BΔ21(H77c, 1a) was eluted from the heparin-Sepharose in buffer C with a 200 mM to 1 M NaCl gradient. Peak fractions containing the polymerase were then pooled and diluted with buffer C to achieve a final NaCl of 200 mM and loaded onto a Resource S column. Peak fractions containing the his-tag NS5B(H77c, 1a) were pooled, loaded and size fractionated on a Superose 12 column in buffer C containing 600 mM NaCl. Peak fractions contain highly pure his-tag NS5B were pooled and stored at −80° C. until use.

The GBV-B and the HCV 1a polymerases were used to titrate probe ii, using the protocol described in Example 3. FIGS. 11 and 12 show the titration curves observed with the GBV-B polymerase and the NS5B(H77c, 1a) polymerase, respectively. The $K_d$ value of probe ii for the GBV-B enzyme was 1.8 uM (estimated value with an incomplete curve and an $r_b$ value of 0.21), illustrating the weak binding of the probe to this distantly related polymerase. In contrast, the $K_d$ for the HCV 1a polymerase was 18 nM, revealing that the 1a genotype enzyme binds probe ii with the same affinity as the HCV 1b genotype polymerase. $K_d$ values for a series of compounds were determined with these two HCV (genotypes 1a and 1b) polymerases, using the assay format described in Example 4.

Results of this experiment are illustrated in Table 2. These results show that the $K_d$ values for this series of inhibitors are in the same range with the two genotypically related HCV enzymes.

TABLE 1

Comparison of compound $K_d$ and $IC_{50}$ values with two different HCV NS5B polymerases

| | $K_d$ value (nM) | | $IC_{50}$ value (nM) | |
|---|---|---|---|---|
| Cpd | His-NS5BΔ21-His | NS5BΔ21 | NS5BΔ21-His | His-NS5BΔ21 |
| X | 44 | 41 | 867 | 66 |
| Y | 22 | 31 | 348 | 68 |
| Z | 92 | 88 | 735 | 34 |

TABLE 2

Comparison of compound $K_d$ values with NS5B polymerases from two HCV genotypes

| | $K_d$ values (nM) | |
|---|---|---|
| Cpd | His-NS5BΔ21(1b) | His-NS5BΔ21(H77c, 1a) |
| A | 2.7 | 1.8 |
| B | 12 | 8.0 |
| C | 5.3 | 7.2 |
| D | 3.5 | 7.1 |
| E | 2.4 | 2.7 |

Discussion

The HCV NS5B polymerase is a prime target in the search for inhibitors of HCV replication. The HCV NS5B enzymatic activity has been studied in vitro with a variety of RNA substrates (Behrens et al., 1996; and many references thereafter). Different preparations of the HCV polymerase exhibit varying efficiencies of product formation with a variety of RNA substrates. Estimations are that only a small fraction (i.e. <1%) of the common preparations of purified recombinant HCV NS5B polymerase interact with RNA substrate to reconstitute processive RNA product synthesis (Carroll SS, et al., 2000. Biochemistry, 39:8243-8249). Moreover, the activity of purified recombinant NS5B polymerase varies significantly with specific RNA substrates; a characteristic that presumably reflects the capability of the NS5B of forming productive replication-competent complexes with these substrates (Zhong W, et al., 2000, J Virol, 74, 9134-9143).

In an effort to overcome the limitations of HCV polymerase assays that use sub-optimal and poorly characterized RNA substrates, the Applicants have developed an assay for specific inhibitors of the HCV polymerase that is independent of the presence of RNA. The assay is based upon the use of a characterized inhibitor specific for the HCV polymerase. In the examples presented above, the inhibitor was labeled with a fluorescein moiety and the interaction of this probe with the NS5B was measured and quantified by fluorescence polarization. However, the interaction can also be measured by the use of a radiolabel, or other common labels placed on the inhibitor and applying common techniques for assessing the association of the labeled probe with an appropriately tagged target HCV polymerase. Binding equilibrium with the fluorescein labeled probe is clearly evident in Example 3, as the fraction of bound probe increased with the amount of HCV polymerase. An HCV polymerase assay with components at equilibrium is an advantage over previous assays with RNA substrates, as the active HCV polymerase that stably associates with RNA substrates in processive complexes does not readily dissociate (Carroll SS, et al., 2000 Biochemistry, 39:8243-8249; Zhong W, et al., 2000 J Virol, 74, 9134-9143; Tomei L, et al. 2000 J. Gen. Virol. 81, 759-767). Though these labeled probes readily dissociate from the HCV polymerase, they do so with low nM dissociation constants and provide the required sensitivity (in the low nM range) to detect potent and specific inhibitors. The assay format is adaptable to screening in 96-well (or higher density) plate format as demonstrated in Example 4. A particular advantage of this high throughput screening format is the extremely stable signal and minimal well-to-well variation that the assay provides, particularly in a convenient non-radioactive format. Specific inhibitors of the HCV polymerase were identified and potencies easily determined with this assay (FIGS. 3 and 4).

The direct binding assay described herein overcomes other limitations of the enzymatic HCV polymerase assay. The in vitro RNA polymerase activity of NS5B is extremely sensitive to ionic strength, and KCl or NaCl concentrations exceeding 100 mM inhibit the reaction (Lohmann V, et a., 1998 Virology 249,108-118; Luo G, et al., 2000, J. Virol., 74, 851-63.) Hence the ability to determine the potency of inhibitors at various salt concentrations is restricted by this limitation of standard enzymatic reactions. The direct binding assay of this invention is amenable to adjustments in salt concentration or pH levels as demonstrated in Example 6. The potencies and interaction of specific inhibitors with the NS5B target can easily be determined under conditions not suitable for enzymatic RNA polymerization studies (such as the absence of divalent cation).

Established HCV polymerase enzymatic assays provide $IC_{50}$ values as representative measurements of inhibitor potencies. For inhibitors that are competitive with either RNA or NTP, the $IC_{50}$ value is proportional to the concentration of substrates in the assay and will vary depending on the concentration of these components. The assay described herein permits a direct measurement of inhibitor potencies (reflected by $K_d$ values), under defined conditions, irrespective of the substrate concentration. In enzymatic reactions that use either the N-terminal tag His-NS5BΔ21 or the C-terminal tag NS5BΔ21-His, significantly disparate IC$_{50}$ values are obtained for identical compounds assayed under identical conditions. The His-NS5BΔ21 and NS5BΔ21-His polymerases have different affinities for the primer/template RNA substrate thereby resulting in the disparate IC$_{50}$ for the identical compounds (Example 7, Table 1). A major advantage that is exemplified by the direct binding assay described in this invention is that these differences are reconciled by the relatively similar K$_d$ values that the individual inhibitors display with the two different HCV polymerases.

The direct binding assay described herein has also been shown to be specific for HCV polymerase enzymes. Example 8, in which a K$_d$ at least 100-fold higher for the probe ii was obtained with the GBV-B polymerase, illustrates the weak binding of the probe to this polymerase and the specificity of binding to the HCV polymerases. Moreover, Example 8 also demonstrates that the polymerases from two distinct and clinically relevant HCV genotypes bind the probe with similar affinities.

The direct inhibitor-binding assay of this invention alleviates many restrictions of conventional HCV polymerase enzymatic assays described to date. The Applicants have exemplified how the use of a characterized inhibitor as a competitive probe provides a number of improvements and advancements in the search for specific inhibitors of the NS5B polymerase. This assay may accelerate the identification and characterization of candidate therapeutics for the treatment of HCV related diseases.

All documents referred to herein are hereby incorporated by reference in their entirety.

What is claimed is:

1. A method for identifying compounds binding to Hepatitis C Virus polymerase comprising the steps of:
   a) contacting said Hepatitis C Virus polymerase with a probe being capable of binding to said Hepatitis C Virus polymerase, so as to form a complex comprising said probe bound to said polymerase;
   b) measuring a signal emitted from said probe in said complex to establish a base line level;
   c) incubating said complex from step a) with a test compound;
   d) measuring said signal from said complex from step c); and
   e) comparing said signal from step d) with said signal from step b)

wherein said probe is comprised of a compound according to general formula Ia:

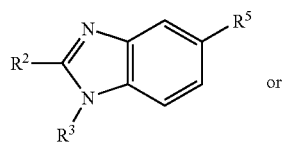

or wherein $R^2$ is $CON(R^{22})_2$, wherein each $R^{22}$ is independently H, $(C_{1-6})$alkyl, $(C_{3-7})$cycloalkyl, $(C_{5-7})$cycloalkenyl, 6 or 10-membered aryl or Het, or both $R^{22}$ are bonded together to form a 5, 6 or 7-membered saturated heterocycle with the nitrogen to which they are attached;

or $R^2$ is selected from: H, halogen, $(C_{1-6})$alkyl, haloalkyl, $(C_{2-6})$alkenyl, $(C_{5-7})$cycloalkenyl, 6 or 10-membered aryl or Het; wherein each of said alkyl, haloalkyl, $(C_{2-6})$alkenyl, $(C_{5-7})$cycloalkenyl, aryl or Het is optionally substituted with $R^{20}$, wherein $R^{20}$ is defined as:

1 to 4 substituents selected from: halogen, $NO_2$, cyano, azido, $C(=NH)NH_2$, $C(=NH)NH(C_{1-6})$alkyl or $C(=NH)NHCO(C_{1-6})$alkyl; or 1 to 4 substituents selected from:

a) $(C_{1-6})$alkyl or haloalkyl, $(C_{3-7})$cycloalkyl, $(C_{2-6})$alkenyl, $(C_{2-8})$alkynyl, $(C_{1-6})$ alkyl-$(C_{3-7})$cycloalkyl, all of which optionally substituted with $R^{150}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$ alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{150}$;

d) $SR^{108}$, $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6})$Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$ alkyl)Het or heterocycle being optionally substituted with $R^{150}$;

e) $NR^{111}R^{112}$ wherein $R^{111}$ is H, $(C_{1-6})$alkyl, $C_{(3-7)}$cycloalkyl or $(C_{1-6})$alkyl-$(C_{3-7})$cycloalkyl, aryl, Het, $(C_{1-6}$alkyl)aryl or $(C_{1-6}$alkyl)Het and $R^{112}$ is H, CN, $(C_{1-6})$alkyl, $(C_{3-7})$cycloalkyl or $(C_{1-6})$ alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$ alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$ cycloalkyl, aryl, Het $(C_{1-6}$alkyl)aryl or $(C_{1-6}$alkyl) Het, said $(C_{1-6})$alkyl, $(C_{3-7})$cycloalkyl, $(C_{1-6})$ alkyl-($C_{3-7}$)cyclocalkyl, aryl, Het, ($C_{1-6}$alkyl)aryl or ($C_{1-6}$alkyl)Het being optionally substituted with $R^{150}$;

g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$) alkyl-($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, ($C_{1-6}$)alkyl-($C_{3-7}$)cycloalkyl, aryl, Het, ($C_{1-6}$alkyl)aryl or ($C_{1-6}$ alkyl)Het or heterocycle being optionally substituted with $R^{150}$;

h) $NR^{121}COCOR^{122}$ wherein $R^{121}$ and $R^{122}$ is each is H, ($C_{1-6}$)alkyl, ($C_{3-7}$)cycloalkyl ($C_{1-6}$)alkyl-($C_{3-7}$)cycloalkyl, a 6- or 10-membered aryl, Het, ($C_{1-6}$ alkyl)aryl or ($C_{1-6}$alkyl)Het, said alkyl, cycloalkyl, alkyl-cycloalkyl, aryl, Het, ($C_{1-6}$alkyl)aryl or ($C_{1-6}$alkyl)Het being optionally substituted with $R^{150}$; or $R^{122}$ is $OR^{123}$ or $N(R^{124})_2$ wherein $R^{123}$ and each $R^{124}$ is independently H, ($C_{1-6}$alkyl), ($C_{3-7}$)cycloalkyl, aryl, Het, ($C_{1-6}$alkyl)aryl or ($C_{1-6}$ alkyl)Het, or $R^{124}$ is OH or O ($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{150}$;

i) $COR^{127}$ wherein $R^{127}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het ($C_{1-6}$alkyl)aryl or ($C_{1-6}$alkyl)Het being optionallyl substituted with $R^{150}$;

j) $COOR^{128}$ wherein $R^{128}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl and ($C_{1-6}$alkyl)Het being optionally substituted with $R^{150}$;

k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$ alkyl)Het and heterocycle being optionally substituted with $R^{150}$;

l) aryl, Het, (C1-6alkyl)aryl or (C1-6alkyl)Het, all of which being optionally substituted with $R^{150}$;

wherein $R^{150}$ is preferably:

1 to 3 substituents selected from: halogen, $NO_2$, cyano or azido; or 1 to 3 substituents selected from:

a) ($C_{1-6}$)alkyl or haloalkyl, ($C_{3-7}$)cycloalkyl, ($C_{2-6}$) alkenyl, ($C_{2-8}$)alkynyl, ($C_{1-6}$)alkyl-($C_{3-7}$)cycloalkyl, all of which optionally substituted with $R^{160}$;

b) $OR^{104}$ wherein $R^{104}$ is H, ($C_{1-6}$)alkyl) or said alkyl or cycloalkyl optionally substituted with $R^{160}$;

d) $SR^{108}$, $SO_3H$, $SO_2N(R^{108})C(O)R^{108}$ wherein each $R^{108}$ is independently H, ($C_{1-6}$)alkyl, ($C_{3-7}$)cyloalkyl or ($C_{1-6}$)alkyl-($C_{3-7}$)cycloalkyl, aryl, Het, or both $R^{108}$ are covalently bonded together and to the nitrogen to which they are attached to form a 5, 6 or 7-membered saturated heterocycle said alkyl cycloalkyl, aryl, Het and heterocycle being optionally sustituted with $R^{160}$;

e) $NR^{111}R^{112}$ wherein $R^{111}$ is H, ($C_{1-6}$)alkyl, or ($C_{3-7}$)cycloalkyl, and $R^{112}$ is H, ($C_{1-6}$)alkyl or ($C_{3-7}$cycloalkyl, $COOR^{115}$ or $SO_2R^{115}$ wherein $R^{115}$ is ($C_{1-6}$)alkyl or ($C_{3-7}$)cycloalkyl, or both $R^{111}$ and $R^{112}$ are covalently bonded together and to the nitrogen to which they are attached to form a 5, 6 or 7-membered saturated heterocycle, said alkyl, cycloalkyl and heterocycle being optionally substituted with $R^{160}$;

f) $NR^{116}COR^{117}$ wherein $R^{116}$ and $R^{117}$ is each H, ($C_{1-6}$)alkyl or ($C_{3-7}$)cycloalkyl said ($C_{1-6}$)alkyl and ($C_{3-7}$)cycloalkyl being optionally substituted with $R^{160}$;

g) $NR^{118}CONR^{119}R^{120}$, wherein $R^{118}$, $R^{119}$ and $R^{120}$ is each H, ($C_{1-6}$)alkyl or ($C_{3-7}$)cycloalkyl, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which the are attached to form a 5, 6 or 7-membered saturated heterocycle; said alkyl, cycloalkyl, and heterocycle being optionally substituted with $R^{160}$;

h) $NR^{121}COCOR^{122}$ wherein $R^{121}$ is H, ($C_{1-6}$)alkyl or $(_{3-7})$cycloalkyl, said alkyl and cycloalkyl being optionally substituted with $R^{160}$; or $R^{122}$ is $OR^{123}$ or $N(R^{124})_2$ wherein $R^{123}$ and each $R^{124}$ is independently H, ($C_{1-6}$alkyl) or ($C_{3-7}$)cycloalkyl, or both $R^{124}$ are covalently bonded together to form a 5, 6 or 7-membered saturated heterocycle, said alkyl, cycloalkyl and heterocycle being optionally substituted with $R^{160}$;

i) $COR^{127}$ wherein $R^{127}$ is H, ($C_{1-6}$)alkyl or ($C_{3-7}$) cycloalkyl, said alkyl and cycloalkyl being optionally substituted with $R^{160}$;

j) $COOR^{128}$ wherein $R^{128}$ is H, ($C_{1-6}$)alkyl or ($C_{3-7}$) cycloalkyl, said ($C_{1-6}$)alkyl and ($C_{3-7}$)cycloalkyl being optionally substituted with $R^{160}$; and k) $CONR^{129}R^{130}$ wherein $R^{129}$ and $R^{130}$ are independently H, ($C_{1-6}$)alkyl or ($C_{3-7}$)cycloalkyl or both $R^{129}$ and $R^{130}$ are covalently bonded together and to the nitrogen to which they are attached to form a 5, 6 or 7-membered saturated heterocycle, said alkyl, cycloalkyl and heterocycle being optionally substituted with $R^{160}$;

wherein $R^{160}$ is defined as 1 or 2 substituents selected from: halogen CN, $C_{1-6}$alkyl, haloalkyl, $COOR^{161}$, $OR^{161}$, $N(R^{162})_2$, $SO_2N(R^{162})_2$, or $CON(R^{162})_2$, wherein $R^{161}$ and each $R^{162}$ is independently H, ($C_{1-6}$)alkyl, ($C_{3-7}$)cycloalkyl or ($C_{1-6}$)alkyl-($C_{3-7}$)cycloalkyl; or both $R^{162}$ are covalently bonded together and to the nitrogen to which they are attached to form a 5, 6 or 7-membered saturated heterocycle;

$R^3$ is selected from ($C_{3-7}$)cycloalkyl, ($C_{6-10}$)bicycloalkl, 6- or 10-membered aryl, or Het;

$R^5$ is —C(O)-Z, wherein

Z is $OR^6$ wherein $R^6$ is $C_{1-6}$alkyl substituted with:

1 to 4 substituents selected from: $OPO_3H$, $NO_2$, cyano, azido, C(=NH)$NH_2$, C(=NH)NH($C_{1-6}$)alkyl or C(=NH)NHCO($C_{1-6}$)alkyl; or 1 to 4 substituents selected from:
- a) $(C_{1-6})$alkyl or haloalkyl, $(C_{3-7})$cycloalkyl, $C_{3-7}$spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{150}$;
- b) $OR^{104}$ wherein $R^{104}$ is $(C_{1-6}$alkyl) substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said cycloalkyl, aryl, Het, $(C_{1-6}$alkyl)aryl or $(C_{1-6}$alkyl)Het being optionally substituted with $R^{150}$;
- c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;
- d) $SR^{108}$, $SO_3H$, $SO_2N(R^{108})_2$ or $SO^2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl aryl, Het, $(C_{1-6}$alkyl)aryl or $(C_{1-6}$alkyl)Het or heterocycle being optionally substituted with $R^{150}$;
- e) $NR^{111}R^{112}$ wherein $R^{111}$ is $(C_{1-6})$alkyl substituted with $R^{150}$, $(C_{3-7})$cycloakyl or $(C_{1-6})$akyl-$(C_{3-7})$cycloalkyl, aryl, Het, $(C_{1-6}$alkyl)aryl or $(C_{1-6}$alkyl)Het, and $R^{112}$ is CN, $(C_{1-6})$alkyl substituted with $R^{150}$, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)aryl, Het, $COOR^{115}$ or $SO_2R^{115}$ wherein $R^{115}$ is $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said cycloalkyl, aryl, Het, $(C_{1-6}$alkyl)aryl or $(C_{1-6}$alkyl)Het, or heterocycle being optionally substituted with $R^{150}$;
- f) $NR^{116}COR^{117}$ wherein $R^{116}$ and $R^{117}$ is each H, $(C_{1-6})$akyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;
- g) $NR^{118}CONR^{119}R^{120}$, wherein $R^{118}$, $R^{119}$ and $R^{120}$ is each H, $(C_{1-6})$alkyl, $(C_{3-7})$cycloakyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6}$alkyl)-$(C_{3-7})$cycloalkyl, aryl, Het, $(C_{1-6}$alkyl)aryl or $(C_{1-6})$Het or heterocycle being optionally substituted with $R^{150}$;
- h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl) aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl) aryl or $C_{1-6}$alkyl)Het and heterocycle being optionally substituted with $R^{150}$;
- i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6})$Het being optionally substituted with $R^{150}$;
- j) $COOR^{128}$ wherein $R^{128}$ is $(C_{1-6})$alkyl substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{3-7})$cycloalkyl or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;
- k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;
- l) aryl, Het, $(C_{1-6}$alkyl)aryl or $(C_{1-6}$alkyl)Het, all of which being optionally substituted with $R^{150}$;

wherein $R^{150}$ is:

1 to 3 substituents selected from: halogen, $NO_2$, cyano, azido or 1 to 3 substituents selected from:
- a) $(C_{1-6})$alkyl or haloalkyl, $(C_{3-7})$cycloalkyl, $C_{3-7}$spirocycloalkyl optionally containing 1 or 2 heteroatom, $(C_{2-6})$alkenyl, $(C_{1-6})$alkyl-$(C_{3-7})$cycloalkyl, all of which optionally substituted with $R^{160}$;
- b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)laryl or $(C_{1-6}$alkyl)Het being optionally substituted with $R^{160}$;
- d) $SO_3H$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{160}$;
- e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het, or heterocycle being optionally substituted with $R^{150}$;
f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{160}$;
g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{119}$ and $R^{120}$ are covalently bonded together and to the nitrogen to which they are attached to form a 5, 6 or 7-membered saturated heterocycle; said alkyl, cycloalkyl, ($C_{1-6}$)alkyl-($C_{3-7}$)cycloalkyl, aryl, Het, ($C_{1-6}$alkyl)aryl or ($C_{1-6}$alkyl)Het or heterocycle being optionally substituted with $R^{160}$;
h) $NR^{121}COCOR^{122}$ wherein $R^{123}$ is H, ($C_{1-6}$)alkyl optionally substituted with $R^{160}$; or $R^{122}$ is $OR^{123}$ or $N(R^{124})_2$ wherein $R^{123}$ and each $R^{124}$ is independently H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or $R^{124}$ is OH or O($C_{1-6}$alkyl) or both $R^{124}$ are covalently bonded together to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{160}$;
j) tetrazole, $COOR^{128}$ wherein $R^{128}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl and ($C_{1-6}$alkyl)Het being optionally substituted with $R^{160}$; and
k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, ($C_{1-6}$)alkyl, ($C_{3-7}$)cycloalkyl or ($C_{1-6}$)alkyl-($C_{3-7}$)cycloalkyl: or both $R^{162}$ are covalently bonded together and to the nitrogen to which they are attached to form a 5, 6 or 7-membered saturated heterocycle;

or Z is $N(R^{6a})R^6$, wherein $R^{6a}$ is H or ($C_{1-6}$alkyl) and $R^6$ is ($C_{1-6}$alkyl) optionally substituted with:
  1 to 4 substituents selected from: $OPO_3H$, $NO_2$, cyano, azido, $C(=NH)NH_2$, $C(=NH)NH(C_{1-6})$alkyl or $C(=NH)NHCO(C_{1-6})$alkyl; or
  1 to 4 substituents selected from:

a) ($C_{1-6}$)alkyl substituted with $R^{150a}$, haloalkyl, ($C_{3-7}$)cycloalkyl, $C_{3-7}$ spirocycloalkyl optionally containing 1 or 2 heteroatom, ($C_{2-6}$)alkenyl, ($C_{2-8}$)alkynyl, ($C_{1-6}$)alkyl-($C_{3-7}$)cycloalkyl, all of which optionally substituted with $R^{150}$, wherein $R^{150a}$ is the same as $R^{150}$ but is not halogen, $OR^{150b}$, $COOR^{150b}$, $N(R^{150b})_2$, wherein $R^{150b}$ is H or $C_{1-6}$alkyl;
b) $OR^{104}$ wherein $R^{104}$ is ($C_{1-6}$alkyl) substituted with $R^{150}$, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said cycloalkyl, aryl, Het, ($C_{1-6}$alkyl)aryl or ($C_{1-6}$alkyl)Het being optionally substituted with $R^{150}$;
c) $OCOR^{105}$ wherein $R^{105}$ is ($C_{1-6}$)alkyl, ($C_{3-7}$)cycloalkyl, ($C_{1-6}$)alkyl-($C_{3-7}$)cycloalkyl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{150}$;
d) $SO_3H$, $SO_2N(R^{108})_2$ or $SO_2N(R^{108})C(O)R^{108}$ wherein each $R^{108}$ is independently H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het or heterocycle being optionally substituted with $R^{150}$;
e) $NR^{111}R^{112}$ wherein $R^{111}$ is ($C_{1-6}$)alkyl substituted with $R^{150}$, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, and $R^{112}$ is H, CN, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl, ($C_{1-6}$alkyl)Het or $R^{111}$ is H and $R^{112}$ is $SO_2R^{115}$ wherein $R^{115}$ is ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or both $R^{111}$ and $R^{112}$ are covalently bonded together and to the nitrogen to which they are attached to form a 5, 6 or 7-membered saturated heterocycle, said cycloalkyl, aryl, Het, ($C_{1-6}$alkyl)aryl or ($C_{1-6}$alkyl)Het, or heterocycle being optionally substituted with $R^{150}$;
f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{150}$;
g) $NR^{118}CONR^{119}R^{120}$, wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, ($C_{1-6}$)alkyl-($C_{3-7}$)cycloalkyl, aryl, Het, ($C_{1-6}$alkyl)aryl or ($C_{1-6}$alkyl)Het or heterocycle being optionally substituted with $R^{150}$;
h) $NR^{121}COCOR^{122}$ wherein $R^{121}$ and $R^{122}$ is each is H, ($C_{1-6}$)alkyl, ($C_{3-7}$)cycloalkyl, ($C_{1-6}$)alkyl-($C_{3-7}$)cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6}$)alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;
i) $COR^{127}$ wherein $R^{127}$ is H, $(C_{1-6}$)alkyl, $(C_{3-7})$cycloalkyl or $(C_{1-6}$)alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{150}$;
j) $COOR^{128}$ wherein $R^{128}$ is $(C_{1-6}$)alkyl substituted with $R^{150}$, $(C_{3-7})$cycloalkyl, or $(C_{1-6}$)alkyl-$(C_{3-7})$cycloalkyl, aryl, Het, $(C_{1-6}$alkyl)aryl or $(C_{1-6}$ alkyl)Het, said $(C_{3-7})$cycloalkyl, or $(C_{1-6}$)alkyl-$(C_{3-7})$cycloalkyl, aryl, Het, $(C_{1-6}$alkyl)aryl and $(C_{1-6}$alkyl)Het being optionally substituted with $R^{150}$;
k) $CONR^{129}R^{130}$ wherein $R^{129}$ and $R^{130}$ are independently H, $(C_{1-6}$)alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$ alkyl)Het and heterocycle being optionally substituted with $R^{150}$;
l) aryl, Het, $(C_{1-6}$alkyl)aryl or $(C_{1-6}$alkyl)Het, all of which being optionally substituted with $R^{150}$; and wherein $R^{150}$ is selected from:

1 to 3 substituents selected from: halogen, $NO_2$, cyano, azido or 1 to 3 substituents selected from:
a) $(C_{1-6}$)alkyl or haloalkyl, $(C_{3-7})$cycloalkyl, $C_{3-7}$ spirocycloalkyl optionally containing 1 or 2 heteroatom, $(C_{2-6})$alkenyl, $(C_{1-6}$)alkyl-$(C_{3-7})$cycloalkyl, all of which optionally substituted with $R^{160}$;
b) $OR^{104}$ wherein $R^{104}$ is H, $(C_{1-6}$alkyl), $(C_{3-7})$cycloalkyl, or $(C_{1-6}$)alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{160}$;
d) $SO_3H$, $SO_2N(R^{108})_2$ or $SO_2N(R^{108})C(O)R^{108}$ wherein each $R^{108}$ is independently H, $(C_{1-6}$)alkyl, $(C_{3-7})$cycloalkyl or $(C_{1-6}$)alkyl-$(C_{3-7})$cycloalkyl, aryl, Het, $(C_{1-6}$-alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$ alkyl)Het or heterocycle being optionally substituted with $R^{160}$;
e) $NR^{111}R^{112}$ wherein $R^{111}$ is H, $(C_{1-6}$)alkyl, $(C_{3-7})$cycloalkyl or $(C_{1-6}$)alkyl-$(C_{3-7})$cycloalkyl, aryl, Het, $(C_{1-6}$alkyl)aryl or $(C_{1-6}$alkyl)Het, and $R^{112}$ is H, $(C_{1-6}$)alkyl, $(C_{3-7})$cycloalkyl or $(C_{1-6}$)alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6}$)alkyl, $(C_{3-7})$cycloalkyl, or $(C_{1-6}$)alkyl-$(C_{3-7})$cycloalkyl, aryl, Het, $(C_{1-6}$alkyl)aryl or $(C_{1-6}$ alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{160}$;

f) $NR^{116}COR^{117}$ wherein $R^{116}$ and $R^{117}$ is each H, $(C_{1-6}$)alkyl, $(C_{3-7})$cycloalkyl, $(C_{1-6}$)alkyl-$(C_{3-7})$cycloalkyl, aryl, Het, $(C_{1-6}$alkyl)aryl or $(C_{1-6}$ alkyl)Het, said $(C_{1-6}$)alkyl, $(C_{3-7})$cycloalkyl, $(C_{1-6}$)alkyl-$(C_{3-7})$cycloalkyl, aryl, Het, $(C_{1-6}$alkyl)aryl or $(C_{1-6}$alkyl)Het being optionally substituted with $R^{160}$;

g) $NR^{118}CONR^{119}R^{120}$, wherein $R^{118}$, $R^{119}$ and $R^{120}$ is each H, $(C_{1-6}$)alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$-alkyl)Het, or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{160}$;

h) $NR^{121}COCOR^{122}$ wherein $R^{121}$ is H, $(C_{1-6}$)alkyl optionally substituted with $R^{160}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6}$)alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$ alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{160}$;

j) tetrazole, $COOR^{128}$ wherein $R^{128}$ is H, $(C_{1-6}$)alkyl, $(C_{3-7})$cycloalkyl, or $(C_{1-6}$)alkyl-$(C_{3-7})$cycloalkyl, aryl, Het, $(C_{1-6}$alkyl)aryl or $(C_{1-6}$alkyl)Het, said $(C_{1-6}$)alkyl, $(C_{3-7})$cycloalkyl, or $(C_{1-6}$)alkyl-$(C_{3-7})$cycloalkyl, aryl, Het, $(C_{1-6}$alkyl)aryl and $(C_{1-6}$ alkyl)Het being optionally substituted with $R^{160}$; and k) $CONR^{129}R^{130}$ wherein $R^{129}$ and $R^{130}$ are independently H, $(C_{1-6}$)alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$ alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, $(C_{1-6}$)alkyl, $(C_{3-7})$cycloalkyl or $(C_{1-6}$)alkyl-$(C_{3-7})$cycloalkyl; or both $R^{162}$ are covalently bonded together and to the nitrogen to which they are attached to form a 5, 6 or 7-membered saturated heterocycle;

or $R^6$ is

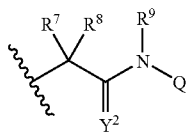

wherein, preferably, $R^7$ and $R^8$ are each independently H, $(C_{1-6})$alkyl, haloalkyl, $(C_{3-7})$cycloalkyl, 6- or 10-membered aryl, Het, $(C_{1-6})$alkyl-aryl, $(C_{1-6})$alkyl-Het, wherein said alkyl, cycloalkyl, aryl, Het, $(C_{1-6})$alkyl-aryl, $(C_{1-6})$alkyl-Het are optionally substituted with $R^{70}$; or $R^7$ and $R^8$ are covalently bonded together to form second $(C_{3-7})$cycloalkyl or a 4, 5- or 6-membered heterocycle having from 1 to 3 heteroatom selected from O, N, and S; or when Z is $N(R^{6a})R^6$, either of $R^7$ or $R^8$ is covalently bonded to $R^{6a}$ to form a nitrogen-containing 5- or 6-membered heterocycle;

wherein $R^{70}$ is selected from:

1 to 4 substituents selected from: halogen, $NO_2$, cyano, azido; or 1 to 4 substituents selected from:
- a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$alkyl-$(C_{3-7})$cycloalkyl, all of which optionally substituted with $R^{150}$;
- b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;
- d) $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$ alkyl)Het or heterocycle being optionally substituted with $R^{150}$;
- e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$ alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;
- f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$ alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl) aryl or $(C_{1-6}$-alkyl)Het being optionally substituted with $R^{150}$;
- g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$ alkyl)Het or heterocycle being optionally substituted with $R^{150}$;
- h) $NR^{121}COCOR^{122}$ wherein $R^{121}$ is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl) Het being optionally substituted with $R^{150}$; and $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$ alkyl)Het and heterocycle being optionally substituted with $R^{150}$;
- i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{150}$;
- j) $COOR^{128}$ wherein $R^{128}$ is H, $(C_{1-6})$alkyl, $(C_{3-7})$ cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$ alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl) Het being optionally substituted with $R^{150}$;
- k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$ alkyl)Het and heterocycle being optionally substituted with $R^{150}$;
- l) aryl, Het, $(C_{1-6}$alkyl)aryl or (C1-6alkyl)Het, all of which being optionally substituted with $R^{150}$;

wherein $R^{150}$ is selected from:

1 to 3 substituents selected from: halogen, $NO_2$, cyano, azido; or 1 to 3 substituents selected from:
- a) $(C_{1-6})$alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, all of which optionally substituted with $R^{160}$;
- b) $OR^{104}$ wherein $R^{104}$ is H, $(C_{1-6}$alkyl) or $(C_{3-7})$ cycloalkyl, said alkyl and cycloalkyl being optionally substituted with $R^{160}$;
- d) $SO_2N(R^{108})_2$ wherein $R^{108}$ is H, $(C_{1-6})$alkyl or $(C_{3-7})$cycloalkyl, said alkyl or cycloalkyl being optionally substituted with $R^{160}$;

e) $NR^{111}R^{112}$ wherein $R^{111}$ is H, $(C_{1-6})$alkyl or $(C_{3-7})$cycloalkyl, and $R^{112}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{160}$;

f) $NR^{116}COR^{117}$ wherein $R^{116}$ and $R^{117}$ is each H, $(C_{1-6})$alkyl or $(C_{3-7})$cycloalkyl, said $(C_{1-6})$alkyl or $(C_{3-7})$cycloalkyl being optionally substituted with $R^{160}$;

g) $NR^{118}CONR^{119}R^{120}$, wherein $R^{118}$, $R^{119}$ and $R^{120}$ is each H, $(C_{1-6})$alkyl or $(C_{3-7})$cycloalkyl; or $R^{119}$ and $R^{120}$ are covalently bonded together and to the nitrogen to which they are attached to form a 5, 6 or 7-membered saturated heterocycle; said alkyl, cycloalkyl or heterocycle being optionally substituted with $R^{160}$;

h) $NR^{121}COCOR^{122}$ wherein $R^{121}$ is H, $(C_{1-6})$alkyl or $(C_{3-7})$cycloalkyl, said alkyl or cycloalkyl being optionally substituted with $R^{160}$; or $R^{122}$ is $OR^{123}$ or $N(R^{124})_2$ wherein $R^{123}$ and each $R^{124}$ is independently H, $(C_{1-6}$alkyl) or $(C_{3-7})$cycloalkyl, or $R^{124}$ is OH or O$(C_{1-6}$alkyl) or both $R^{124}$ are covalently bonded together to form a 5, 6 or 7-membered saturated heterocycle, said alkyl, cycloalkyl and heterocycle being optionally substituted with $R^{160}$;

j) tetrazole, $COOR^{128}$ wherein $R^{128}$ is H, $(C_{1-6})$alkyl or $(C_{3-7})$cycloalkyl, said $(C_{1-6})$alkyl and $(C_{3-7})$ cycloalkyl being optionally substituted with $R^{160}$; and k) $CONR^{129}R^{130}$ wherein $R^{129}$ and $R^{130}$ are independently H, $(C_{1-6})$alkyl or $(C_{3-7})$cycloalkyl, or both $R^{129}$ and $R^{130}$ are covalently bonded together and to the nitrogen to which they are attached to form a 5, 6 or 7-membered saturated heterocycle, said alkyl, cycloalkyl and heterocycle optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $OR^{161}$, $N(R^{162})_2$ or $CON(R^{162})_2$, wherein $R^{161}$ and each $R^{162}$ is independently H or $(C_{1-6})$alkyl;

$Y^2$ is O or S;

$R^9$ is H; or $R^9$ is covalently bonded to either of $R^7$ or $R^8$ to form a 5- or 6-membered heterocycle; and Q is a 6- or 10-membered aryl, Het, all of which being optionally substituted with:

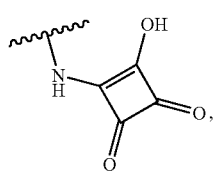

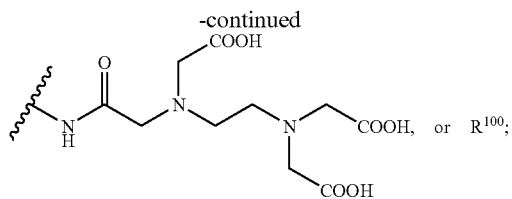

wherein $R^{100}$ is:

1 to 4 substituents selected from: halogen, $NO_2$, cyano or azido; or 1 to 4 substituents selected from:

a) $(C_{1-6})$alkyl or haloalkyl, $(C_{3-7})$cycloalkyl, $(C_{2-6})$ alkenyl, $(C_{2-8})$alkynyl, $(C_{1-6})$ alkyl-$(C_{3-7})$cycloalkyl, all of which optionally substituted with $R^{150}$;

b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{150}$;

e) $NR^{111}R^{112}$ wherein $R^{111}$ is H, $(C_{1-6})$alkyl, $(C_{3-7})$ cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$ alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$ alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$ cycloalkyl, aryl, Het, $(C_{1-6}$alkyl)aryl or $(C_{1-6}$ alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl) aryl or $(C_{1-6}$alkyl)Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$ alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6})$alkyl-$(C_{3-7})$cycloalkyl, aryl, Het, $(C_{1-6}$alkyl)aryl or $(C_{1-6}$ alkyl)Het or heterocycle being optionally substituted with $R^{150}$;

h) $NR^{121}COCOR^{122}$ wherein $R^{121}$ and $R^{122}$ is each is H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl) aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl) aryl or $(C_{1-6}$alkyl)Het and heterocycle being optionally substituted with $R^{150}$;

j) $COOR^{128}$ wherein $R^{128}$ is H, $(C_{1-6}$)alkyl, $(C_{3-7}$) cycloalkyl, or $(C_{1-6}$)alkyl-$(C_{3-7}$)cycloalkyl, aryl, Het, $(C_{1-6}$alkyl)aryl or $(C_{1-6}$alkyl)Het, said $(C_{1-6}$) alkyl, $(C_{3-7}$)cycloalkyl, or $(C_{1-6}$)alkyl-$(C_{3-7}$)cycloalkyl, aryl, Het, $(C_{1-6}$alkyl)aryl and $(C_{1-6}$alkyl) Het being optionally substituted with $R^{150}$;

k) $CONR^{129}R^{130}$ wherein $R^{129}$ and $R^{130}$ are independently H, $(C_{1-6}$)alkyl, $(C_{3-7}$)cycloalkyl, $(C_{1-6}$) alkyl-$(C_{3-7}$)cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$ alkyl)Het and heterocycle being optionally substituted with $R^{150}$;

l) aryl, Het, $(C_{1-6}$alkyl)aryl or $(C_{1-6}$alkyl)Het, all of which being optionally substituted with $R^{150}$;

wherein $R^{150}$ is selected from:

1 to 3 substituents selected from: halogen, $NO_2$, cyano or azido; or 1 to 3 substituents selected from:
a) $(C_{1-6}$)alkyl or haloalkyl, $(C_{3-7}$)cycloalkyl, $C_{3-7}$ spirocycloalkyl optionally containing 1 or 2 heteroatom, $(C_{2-6}$)alkenyl, $(C_{2-8}$)alkynyl, $(C_{1-6}$) alkyl-$(C_{3-7}$)cycloalkyl, all of which optionally substituted with $R^{160}$;

b) $OR^{104}$ wherein $R^{104}$ is H, $(C_{1-6}$alkyl), $(C_{3-7}$)cycloalkyl, or $(C_{1-6}$)alkyl-$(C_{3-7}$)cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$ alkyl)Het being optionally substituted with $R^{160}$;

d) $SO_3H$, $SO_2N(R^{108})_2$ or $SO_2N(R^{108})C(O)R^{108}$ wherein each $R^{108}$ is independently H, $(C_{1-6}$)alkyl, $(C_{3-7}$)cycloalkyl or $(C_{1-6}$)alkyl-$(C_{3-7}$)cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$ alkyl)Het or heterocycle being optionally substituted with $R^{160}$;

e) $NR^{111}R^{112}$ wherein $R^{111}$ is H, $(C_{1-6}$)alkyl, $(C_{3-7}$) cycloalkyl or $(C_{1-6}$)alkyl-$(C_{3-7}$)cycloalkyl, aryl, Het, $(C_{1-6}$alkyl)aryl or $(C_{1-6}$alkyl)Het, and $R^{112}$ is H, CN, $(C_{1-6}$)alkyl, $(C_{3-7}$)cycloalkyl or $(C_{1-6}$) alkyl-$(C_{3-7}$)cycloalkyl, aryl, Het, $(C_{1-6}$alkyl)aryl, $(C_{1-6}$alkyl)Het or $SO_2R^{115}$ wherein $R^{115}$ is $(C_{1-6}$) alkyl, $(C_{3-7}$)cycloalkyl, or $(C_{1-6}$)alkyl-$(C_{3-7}$)cycloalkyl, aryl, Het, $(C_{1-6}$alkyl)aryl or $(C_{1-6}$alkyl) Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$ alkyl)aryl or $(C_{1-6}$alkyl)Het, or heterocycle being optionally substituted with $R^{160}$;

f) $NR^{116}COR^{117}$ wherein $R^{116}$ and $R^{117}$ is each H, $(C_{1-6}$)alkyl, $(C_{3-7}$)cycloalkyl, $(C_{1-6}$)alkyl-$(C_{3-7}$) cycloalkyl, aryl, Het, $(C_{1-6}$alkyl)aryl or $(C_{1-6}$ alkyl)Het, said $(C_{1-6}$)alkyl, $(C_{3-7}$)cycloalkyl, $(C_{1-6}$)alkyl-$(C_{3-7}$)cycloalkyl, aryl, Het, $(C_{1-6}$alkyl) aryl or $(C_{1-6}$alkyl)Het being optionally substituted with $R^{160}$;

g) $NR^{118}CONR^{119}R^{120}$, wherein $R^{118}$, $R^{119}$ and $R^{120}$ is each H, $(C_{1-6}$)alkyl, $(C_{3-7}$)cycloalkyl, $(C_{1-6}$) alkyl-$(C_{3-7}$)cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6}$)alkyl-$(C_{3-7}$)cycloalkyl, aryl, Het, $(C_{1-6}$alkyl)aryl or $(C_{1-6}$ alkyl)Het or heterocycle being optionally substituted with $R^{160}$;

h) $NR^{121}COCOR^{122}$ wherein $R^{121}$ is H, $(C_{1-6}$)alkyl optionally substituted with $R^{160}$; or $R^{122}$ is $OR^{123}$ or $N(R^{124})_2$ wherein $R^{123}$ and each $R^{124}$ is independently H, $(C_{1-6}$alkyl), $(C_{3-7}$)cycloalkyl, or $(C_{1-6}$)alkyl-$(C_{3-7}$)cycloalkyl, aryl, Het, $(C_{1-6}$alkyl) aryl or $(C_{1-6}$alkyl)Het, or $R^{124}$ is OH or $O(C_{1-6}$ alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{160}$;

j) tetrazole, $COOR^{128}$ wherein $R^{128}$ is H, $(C_{1-6}$)alkyl, $(C_{3-7}$)cycloalkyl, or $(C_{1-6}$)alkyl-$(C_{3-7}$)cycloalkyl, aryl, Het, $(C_{1-6}$alkyl)aryl or $(C_{1-6}$alkyl)Het, said $(C_{1-6}$)alkyl, $(C_{3-7}$)cycloalkyl, or $(C_{1-6}$)alkyl-$(C_{3-7}$) cycloalkyl, aryl, Het, $(C_{1-6}$alkyl)aryl and $(C_{1-6}$ alkyl)Het being optionally substituted with $R^{160}$; and k) $CONR^{129}R^{130}$ wherein $R^{129}$ and $R^{130}$ are independently H, $(C_{1-6}$)alkyl, $(C_{3-7}$)cycloalkyl, $(C_{1-6}$) alkyl-$(C_{3-7}$)cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$ alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SR^{161}$, $SO_2R^{161}$, $OR^{161}$, $N(R^{162})_2$, $SO_2N(R^{162})_2$, or $CON(R^{162})_2$, wherein $R^{161}$ and each $R^{162}$ is independently H, $(C_{1-6}$)alkyl, $(C_{3-7}$)cycloalkyl or $(C_{1-6}$)alkyl-$(C_{3-7}$)cycloalkyl; or both $R^{162}$ are covalently bonded together and to the nitrogen to which they are attached to form a 5, 6 or 7-membered saturated heterocycle;

or an enantiomer, diastereomer or tautomer thereof, including a salt thereof;

wherein said probe comprises a detectable label attached to any suitable position, whereby said probe binds to an HCV polymerase and is capable of being displaced by an inhibitor thereof and whereby a modulation in said signal is an indication that said test compound binds to said polymerase.

2. The method according to claim 1 wherein the detectable label is selected from the group consisting of: a fluorescent label, a radioactive atom, a chemiluminescent label, and a colorimetric label.

3. The method according to claim 2 wherein said label is a fluorescent label or chemiluminescent label.

4. The method according to claim 3, wherein the fluorescent label is selected from the group consisting of: fluorescein, Oregon green, dansyl, rhodamine, Texas-red, phycoerythrin and Eu+.

5. The method according to claim 4, wherein the fluorescent label is fluorescein.

6. The method according to claim 2, wherein the radioactive atom is selected from the group consisting of $^3$H, $^{14}$C and $^{125}$I.

7. The method according to claim 1, wherein the detectable label is a fluorescent reporter/quencher pair.

8. The method according to claim 7, wherein the reporter/quencher pair is selected from the group consisting of: EDANS/DABCYL, tryptophan/2,4-dinitrophenyl, tryptophan/DANSYL, 7-methoxycoumarin/2,4-dinitrophenyl, 2-aminobenzoyl/2,4-dinitrophenyl and 2-aminobenzoyl/3-nitrotyrosine.

9. The method according to claim 1, wherein the probe is selected from:

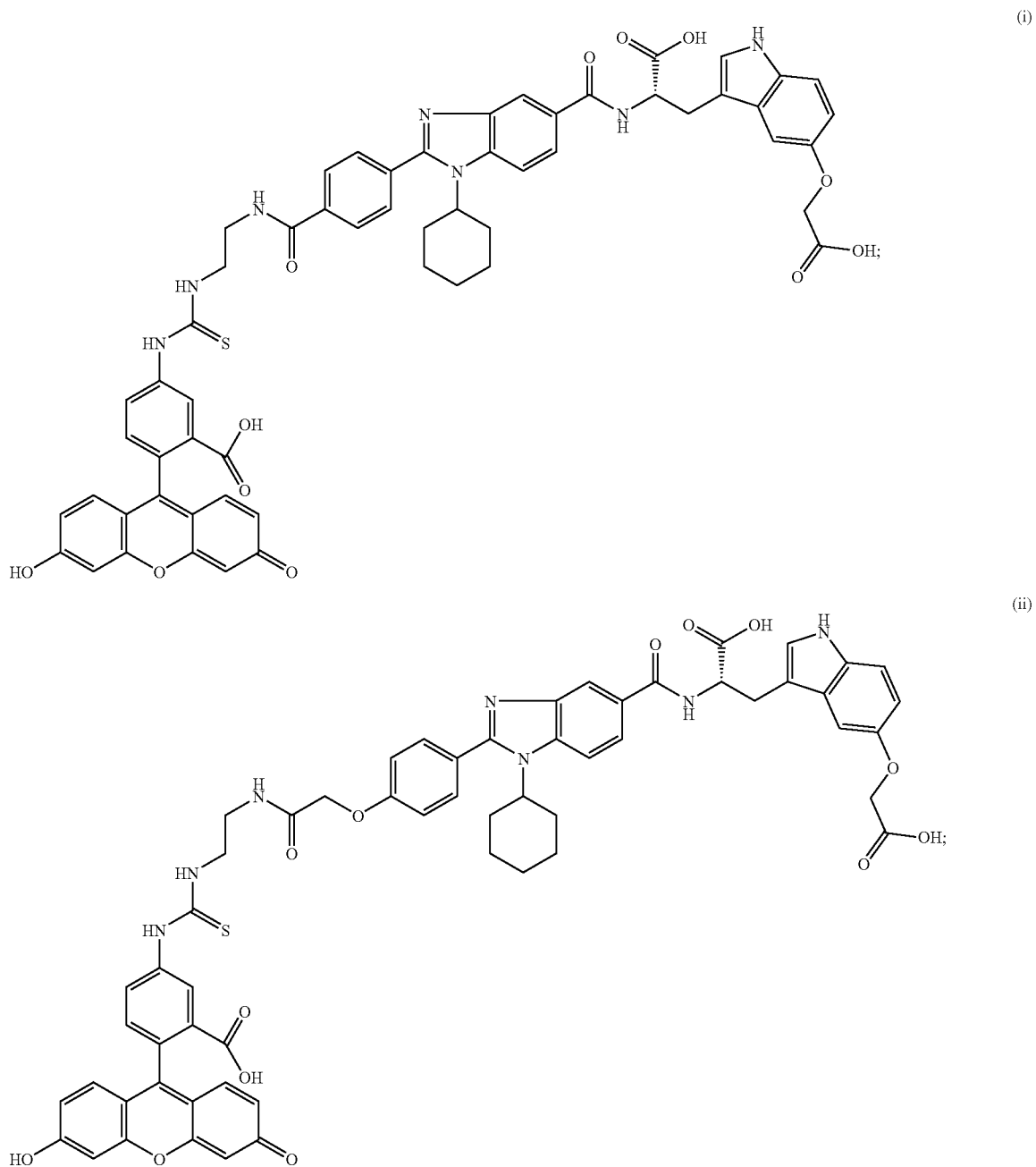

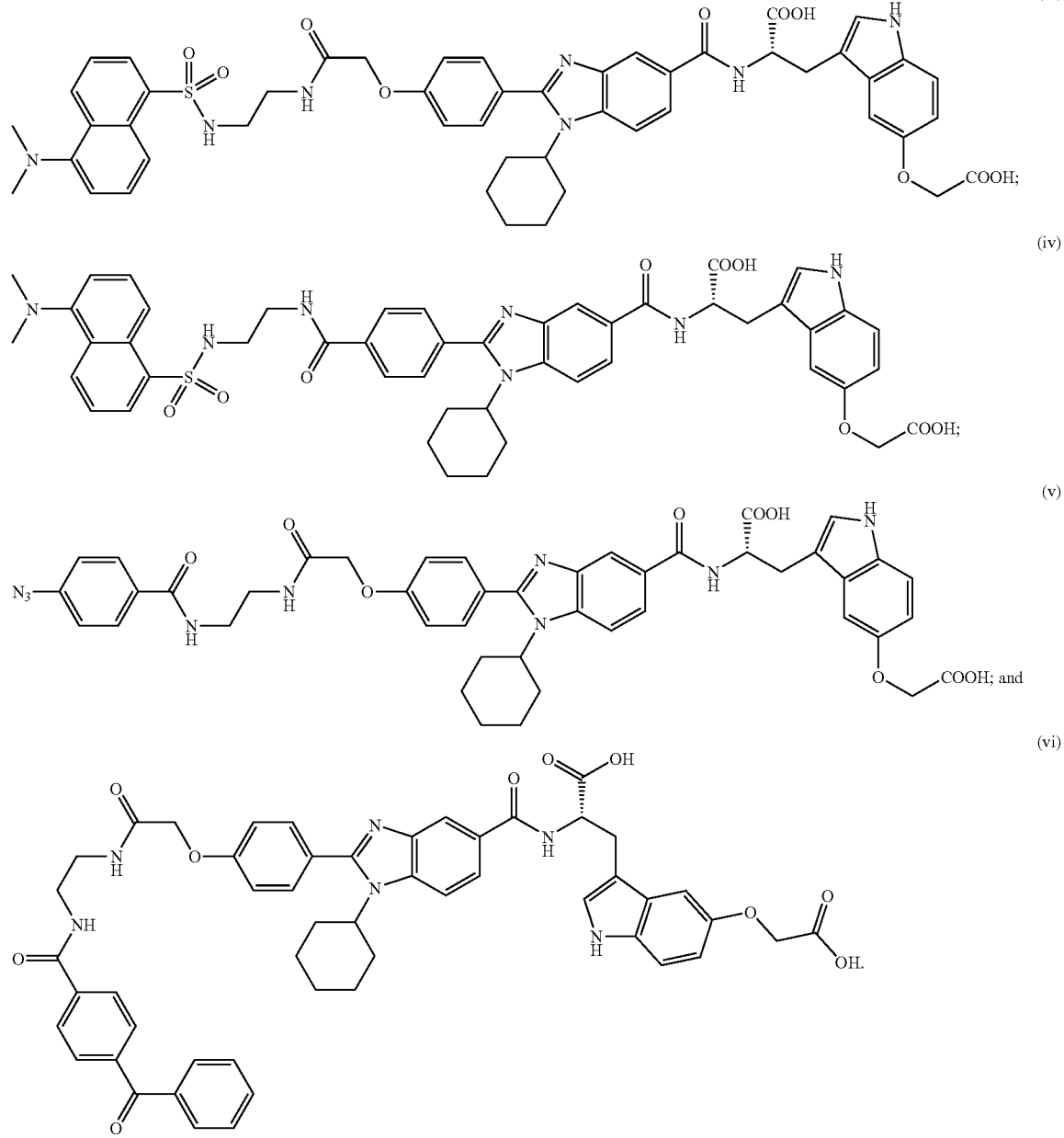

10. A method for development of an assay for identifying inhibitors of Hepatitis C Virus polymerase said method comprising using a probe of formula I, according to claim 1, in the development of an assay for identifying inhibitors of HCV polymerase.

11. A method for identifying compounds that inhibit Hepatitis C Virus polymerase comprising the steps of:
 a) contacting an Hepatitis C Virus polymerase with a probe of formula Ia, according to claim 1, so as to form a complex having said probe bound to said polymerase;
 b) measuring the signal emitted from said probe in said complex to establish a base line signal;
 c) incubating 4complex from step a) with a test compound; and
 d) measuring said signal from said complex from step C): and
 e) comparing said signal from step d) with said signal from step b); whereby a modulation in said signal is an indication that said test compound inhibits said polymerase.

12. A method for identifying compounds capable of inhibiting Hepatitis C Virus polymerase, comprising:
 f) repeating steps (a) to (e), according to claim 11 in a high throughput screen.

13. The method according to claim 11, wherein the Hepatitis C Virus polymerase is selected from the group consisting of NS5B; NSSBΔ21: and NS5BΔ57.

14. The method according to claim 11, wherein the Hepatitis C virus polymerase is obtained from genotype HCV-1a or HCV-1b strains optionally having a histidine tag at either the N- or C-terminal.

15. The method according to claim 1, wherein said probe is a compound having the following formula:

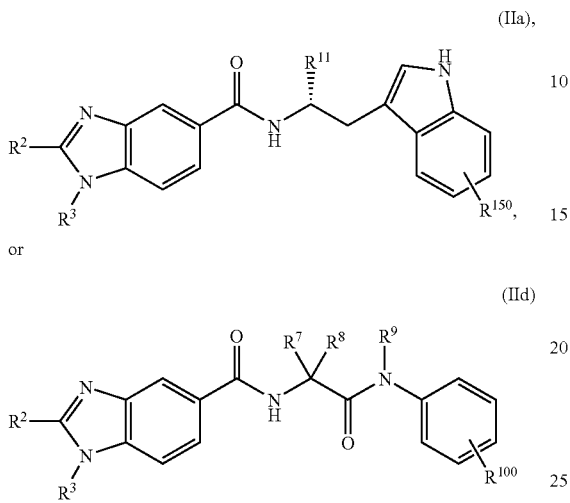

wherein $R^3$ is $(C_{5-6})$cycloalkyl;

$R^2$ is phenyl, or Het both being optionally substituted with $R^{20}$;

$R^7$, $R^8$, $R^9$, $R^{100}$, and $R^{150}$ are as defined according to claim 1;

$R^{11}$ is $OPO_3H$, $NO_2$, cyano, azido, $C(=NH)NH_2$, $C(=NH)NH(C_{1-6})$alkyl or $C(=NH)NHCO(C^{1-6})$alkyl; or a) $(C^{1-6})$alkyl substituted with $R^{150a}$, haloalkyl, $(C_{3-7})$cycloalkyl, $C_{3-7}$ spirocycloalkyl optionally containing 1 or 2 heteroatom, $(C_{2-6})$alkenyl, $(C_{2-6})$alkynyl, $(C_{1-6})$alkyl-$(C_{3-7})$cycloalkyl, all of which optionally substituted with $R^{150}$, wherein $R^{150a}$ is the same as $R^{150}$ but is not halogen, $OR^{150b}$, $COOR^{150b}$, $N(R^{150b})_2$, wherein $R^{150b}$ is H or $C_{1-6}$alkyl;

b) $OR^{104}$ wherein $R^{104}$ is $(C_{1-6}$alkyl) substituted with $R^{150}$, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said cycloalkyl, aryl, Het, $(C_{1-6}$alkyl)aryl or $(C_{1-6}$alkyl)Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SO_3H$, $SO_2N(R^{108})_2$ or $SO_2N(R_{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is $(C_{1-6})$alkyl substituted with $R^{150}$, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het or $R^{111}$ is H and $R^{112}$ is $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7membered saturated heterocycle, said cycloalkyl, aryl, Het, $(C_{1-6}$alkyl)aryl or $(C_{1-6}$alkyl)Het, or heterocycle being optionally substituted with $R^{150}$;

f) $NR^{118}R^{117}$ wherein $R^{118}$ and $R^{117}$ is each H, $(C_{1-6})$alkyl, $(C_{3-7})$cycloalkyl, $(C_{1-6}$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6}$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{118}CONR^{110}R^{120}$, wherein $R^{118}$, $R^{119}$ and $R^{120}$ is each H, $(C_{1-6})$alkyl, $(C_{1-6})$alkyl, $C_{3-7})$cycloalkyl, $(C_{1-6})$alkyl-$(C_{1-6})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle; or $R^{119}$ and $R^{120}$ are covalently bonded together and to the nitrogen to which they are attached to form a 5, 6 or 7-membered saturated heterocycle; said alkyl, cycloalkyl, $(C_{1-6}$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R_{122}$ is each is H, $(C_{1-6})$alkyl, $(C^{3-7})$cycloalkyl, $(C_{1-6}$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{123})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl) Het being optionally substituted with $R^{150}$;

j) $COOR^{128}$ wherein $R^{128}$ is H or $(C_{1-6})$alkyl substituted with $R^{150}$, $(C_{3-7})$cycloalkyl, or $(C_{1-6})$alkyl-$(C_{3-7}$ cycloalkyl, aryl, Het, $(C_{1-6}$alkyl)aryl or $(C_{1-6}$alkyl) Het, said $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl) Het being optionally substituted with $R^{150}$;

k) $CONR^{129}R^{130}$ wherein $R^{129}$ and $R^{130}$ are independently H, ($C_{1-6}$alkyl, ($C^{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently-bonded together and to the nitrogen to which they are attached to form a 5, 6 or 7-membered saturated heterocycle, said alkyl, cycloalkyl, alkyl-cycloalkyl, aryl, Het, ($C^{1-6}$alkyl)aryl, ($C_{1-6}$alkyl)Het and heterocycle being optionally substituted with $R^{150}$;

l) aryl, Het, ($C_{1-6}$alkyl)aryl or ($C_{1-6}$alkyl)Het, all of which being optionally substituted with $R^{150}$ wherein $R^{150}$ is as defined in claim 1;
or a salt thereof;
wherein said compound is optionally:
  a) marked with a radioactive isotope at any suitable position,
  b) linked to a detectable moiety by a suitable linker at any suitable position, except $R^3$; or
  c) linked to an affinity tag at any suitable position, except $R^3$.

16. The method according to claim 1, wherein said probe is a compound having the following formula:

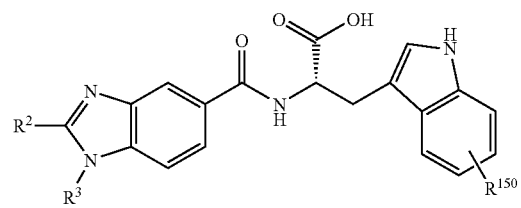

(IIa)

wherein $R^3$ is ($C_{5-6}$)cycloalkyl;
$R^2$ is phenyl, or Het both being optionally substituted with $R^{20}$;
$R^{150}$ are as defined in claim 1;
or a salt thereof:
wherein said compound is optionally:
  a) marked with a radioactive isotope at any suitable position;
  b) linked to a detectable moiety by a suitable linker at any suitable position, except $R^3$; or
  c) linked to an affinity tag at any suitable position, except $R^3$.

* * * * *

SEQUENCE LISTING

<160> NUMBER OF SEQ ID NOS: 4

<210> SEQ ID NO 1
<211> LENGTH: 578
<212> TYPE: PRT
<213> ORGANISM: HCV

<400> SEQUENCE: 1

```
Ser Met Ser Tyr Thr Trp Thr Gly Ala Leu Ile Thr Pro Cys Ala Ala
1               5                   10                  15

Glu Glu Ser Gln Leu Pro Ile Asn Ala Leu Ser Asn Ser Leu Val Arg
            20                  25                  30

His Arg Asn Met Val Tyr Ser Thr Ser Arg Ser Ala Ala Leu Arg
        35                  40                  45

Gln Lys Lys Val Thr Phe Asp Arg Leu Gln Val Leu Asp Asp His Tyr
    50                  55                  60

Arg Asp Val Leu Lys Glu Met Lys Ala Lys Ala Ser Thr Val Lys Ala
65                  70                  75                  80

Lys Leu Leu Ser Val Glu Glu Ala Cys Lys Leu Thr Pro Pro His Ser
                85                  90                  95

Ala Lys Ser Lys Phe Gly Tyr Gly Ala Lys Asp Val Arg Asn Leu Ser
            100                 105                 110

Ser Lys Ala Val Asp His Ile Arg Ser Val Trp Lys Asp Leu Leu Glu
        115                 120                 125

Asp Thr Glu Thr Pro Ile Asp Thr Thr Ile Met Ala Lys Asn Glu Val
    130                 135                 140

Phe Cys Val Gln Pro Glu Lys Gly Gly Arg Lys Pro Ala Arg Leu Ile
145                 150                 155                 160

Val Phe Pro Asp Leu Gly Val Arg Val Cys Glu Lys Met Ala Leu Tyr
                165                 170                 175

Asp Val Val Ser Thr Leu Pro Gln Ala Val Met Gly Ser Ser Tyr Gly
            180                 185                 190

Phe Gln Tyr Ser Pro Lys Gln Arg Val Glu Phe Leu Val Asn Ala Trp
        195                 200                 205

Lys Ser Lys Lys Cys Pro Met Gly Phe Ser Tyr Asp Thr Arg Cys Phe
    210                 215                 220

Asp Ser Thr Val Thr Glu Ser Asp Ile Arg Val Glu Glu Ser Ile Tyr
225                 230                 235                 240

Gln Cys Cys Asp Leu Ala Pro Glu Ala Arg Gln Ala Ile Lys Ser Leu
                245                 250                 255
```

Thr Glu Arg Leu Tyr Ile Gly Gly Pro Leu Thr Asn Ser Lys Gly Gln
            260                 265                 270

Asn Cys Gly Tyr Arg Arg Cys Arg Ala Ser Gly Val Leu Thr Thr Ser
        275                 280                 285

Cys Gly Asn Thr Leu Thr Cys Tyr Leu Lys Ala Ser Ala Ala Cys Arg
    290                 295                 300

Ala Ala Lys Leu Gln Asp Cys Thr Met Leu Val Asn Gly Asp Asp Leu
305                 310                 315                 320

Val Val Ile Cys Glu Ser Ala Gly Thr Gln Glu Asp Ala Ala Asn Leu
                325                 330                 335

Arg Val Phe Thr Glu Ala Met Thr Arg Tyr Ser Ala Pro Pro Gly Asp
            340                 345                 350

Leu Pro Gln Pro Glu Tyr Asp Leu Glu Leu Ile Thr Ser Cys Ser Ser
        355                 360                 365

Asn Val Ser Val Ala His Asp Ala Ser Gly Lys Arg Val Tyr Tyr Leu
    370                 375                 380

Thr Arg Asp Pro Thr Thr Pro Leu Ala Arg Ala Ala Trp Glu Thr Ala
385                 390                 395                 400

Arg His Thr Pro Ile Asn Ser Trp Leu Gly Asn Ile Ile Met Tyr Ala
                405                 410                 415

Pro Thr Leu Trp Ala Arg Met Val Leu Met Thr His Phe Phe Ser Ile
            420                 425                 430

Leu Leu Ala Gln Glu Gln Leu Glu Lys Ala Leu Asp Cys Gln Ile Tyr
        435                 440                 445

Gly Ala Cys Tyr Ser Ile Glu Pro Leu Asp Leu Pro Gln Ile Ile Glu
    450                 455                 460

Arg Leu His Gly Leu Ser Ala Phe Ser Leu His Ser Tyr Ser Pro Gly
465                 470                 475                 480

Glu Ile Asn Arg Val Ala Ser Cys Leu Arg Lys Leu Gly Val Pro Pro
                485                 490                 495

Leu Arg Val Trp Arg His Arg Ala Arg Ser Val Arg Ala Lys Leu Leu
            500                 505                 510

Ser Gln Gly Gly Arg Ala Ala Thr Cys Gly Lys Tyr Leu Phe Asn Trp
        515                 520                 525

Ala Val Arg Thr Lys Leu Lys Leu Thr Pro Ile Pro Ala Ala Ser Arg
    530                 535                 540

Leu Asp Leu Ser Gly Trp Phe Val Ala Gly Tyr Asn Gly Gly Asp Ile
545                 550                 555                 560

Tyr His Ser Leu Ser Arg Ala Arg Pro Arg Leu Glu His His His His
                565                 570                 575

His His

<210> SEQ ID NO 2
<211> LENGTH: 591
<212> TYPE: PRT
<213> ORGANISM: HCV

<400> SEQUENCE: 2

Met Gly Ser Ser His His His His His His Ser Ser Gly Leu Val Pro
1               5                   10                  15

Arg Gly Ser His Met Ser Met Ser Tyr Thr Trp Thr Gly Ala Leu Ile
            20                  25                  30

Thr Pro Cys Ala Ala Glu Glu Ser Gln Leu Pro Ile Asn Ala Leu Ser
        35                  40                  45

```
Asn Ser Leu Val Arg His Arg Asn Met Val Tyr Ser Thr Thr Ser Arg
    50                  55                  60

Ser Ala Ala Leu Arg Gln Lys Lys Val Thr Phe Asp Arg Leu Gln Val
65                  70                  75                  80

Leu Asp Asp His Tyr Arg Asp Val Leu Lys Glu Met Lys Ala Lys Ala
                85                  90                  95

Ser Thr Val Lys Ala Lys Leu Leu Ser Val Glu Glu Ala Cys Lys Leu
                100                 105                 110

Thr Pro Pro His Ser Ala Lys Ser Lys Phe Gly Tyr Gly Ala Lys Asp
            115                 120                 125

Val Arg Asn Leu Ser Ser Lys Ala Val Asp His Ile Arg Ser Val Trp
    130                 135                 140

Lys Asp Leu Leu Glu Asp Thr Glu Thr Pro Ile Asp Thr Thr Ile Met
145                 150                 155                 160

Ala Lys Asn Glu Val Phe Cys Val Gln Pro Glu Lys Gly Gly Arg Lys
                165                 170                 175

Pro Ala Arg Leu Ile Val Phe Pro Asp Leu Gly Val Arg Val Cys Glu
            180                 185                 190

Lys Met Ala Leu Tyr Asp Val Val Ser Thr Leu Pro Gln Ala Val Met
    195                 200                 205

Gly Ser Ser Tyr Gly Phe Gln Tyr Ser Pro Lys Gln Arg Val Glu Phe
    210                 215                 220

Leu Val Asn Ala Trp Lys Ser Lys Lys Cys Pro Met Gly Phe Ser Tyr
225                 230                 235                 240

Asp Thr Arg Cys Phe Asp Ser Thr Val Thr Glu Ser Asp Ile Arg Val
            245                 250                 255

Glu Glu Ser Ile Tyr Gln Cys Cys Asp Leu Ala Pro Glu Ala Arg Gln
                260                 265                 270

Ala Ile Lys Ser Leu Thr Glu Arg Leu Tyr Ile Gly Gly Pro Leu Thr
    275                 280                 285

Asn Ser Lys Gly Gln Asn Cys Gly Tyr Arg Arg Cys Arg Ala Ser Gly
    290                 295                 300

Val Leu Thr Thr Ser Cys Gly Asn Thr Leu Thr Cys Tyr Leu Lys Ala
305                 310                 315                 320

Ser Ala Ala Cys Arg Ala Ala Lys Leu Gln Asp Cys Thr Met Leu Val
            325                 330                 335

Asn Gly Asp Asp Leu Val Val Ile Cys Glu Ser Ala Gly Thr Gln Glu
            340                 345                 350

Asp Ala Ala Asn Leu Arg Val Phe Thr Glu Ala Met Thr Arg Tyr Ser
            355                 360                 365

Ala Pro Pro Gly Asp Leu Pro Gln Pro Glu Tyr Asp Leu Glu Leu Ile
    370                 375                 380

Thr Ser Cys Ser Ser Asn Val Ser Val Ala His Asp Ala Ser Gly Lys
385                 390                 395                 400

Arg Val Tyr Tyr Leu Thr Arg Asp Pro Thr Thr Pro Leu Ala Arg Ala
                405                 410                 415

Ala Trp Glu Thr Ala Arg His Thr Pro Ile Asn Ser Trp Leu Gly Asn
            420                 425                 430

Ile Ile Met Tyr Ala Pro Thr Leu Trp Ala Arg Met Val Leu Met Thr
            435                 440                 445

His Phe Phe Ser Ile Leu Leu Ala Gln Glu Gln Leu Glu Lys Ala Leu
    450                 455                 460
```

```
Asp Cys Gln Ile Tyr Gly Ala Cys Tyr Ser Ile Glu Pro Leu Asp Leu
465                 470                 475                 480

Pro Gln Ile Ile Glu Arg Leu His Gly Leu Ser Ala Phe Ser Leu His
            485                 490                 495

Ser Tyr Ser Pro Gly Glu Ile Asn Arg Val Ala Ser Cys Leu Arg Lys
        500                 505                 510

Leu Gly Val Pro Pro Leu Arg Val Trp Arg His Arg Ala Arg Ser Val
    515                 520                 525

Arg Ala Lys Leu Leu Ser Gln Gly Gly Arg Ala Thr Cys Gly Lys
530                 535                 540

Tyr Leu Phe Asn Trp Ala Val Arg Thr Lys Leu Lys Leu Thr Pro Ile
545                 550                 555                 560

Pro Ala Ala Ser Arg Leu Asp Leu Ser Gly Trp Phe Val Ala Gly Tyr
                565                 570                 575

Asn Gly Gly Asp Ile Tyr His Ser Leu Ser Arg Ala Arg Pro Arg
            580                 585                 590

<210> SEQ ID NO 3
<211> LENGTH: 576
<212> TYPE: PRT
<213> ORGANISM: HCV

<400> SEQUENCE: 3

Met Ser Met Ser Tyr Thr Trp Thr Asp Val Ile Ser Phe Lys Thr Ala
1               5                   10                  15

Ser Lys Val Leu Ser Ala Thr Arg Ala Ile Thr Ser Gly Phe Leu Lys
            20                  25                  30

Gln Arg Ser Leu Val Tyr Val Thr Glu Pro Arg Asp Ala Glu Leu Arg
        35                  40                  45

Lys Gln Lys Val Thr Ile Asn Arg Gln Pro Leu Phe Pro Pro Ser Tyr
    50                  55                  60

His Lys Gln Val Arg Leu Ala Lys Glu Lys Ala Ser Lys Val Val Gly
65                  70                  75                  80

Val Met Trp Asp Tyr Asp Glu Val Ala Ala His Thr Pro Ser Lys Ser
                85                  90                  95

Ala Lys Ser His Ile Thr Gly Leu Arg Gly Thr Asp Val Arg Ser Gly
            100                 105                 110

Ala Ala Arg Lys Ala Val Leu Asp Leu Gln Lys Cys Val Glu Ala Gly
        115                 120                 125

Glu Ile Pro Ser His Tyr Arg Gln Thr Val Ile Val Pro Lys Glu Glu
    130                 135                 140

Val Phe Val Lys Thr Pro Gln Lys Pro Thr Lys Lys Pro Pro Arg Leu
145                 150                 155                 160

Ile Ser Tyr Pro His Leu Glu Met Arg Cys Val Glu Lys Met Tyr Tyr
                165                 170                 175

Gly Gln Val Ala Pro Asp Val Val Lys Ala Val Met Gly Asp Ala Tyr
            180                 185                 190

Gly Phe Val Asp Pro Arg Thr Arg Val Lys Arg Leu Leu Ser Met Trp
        195                 200                 205

Ser Pro Asp Ala Val Gly Ala Thr Cys Asp Thr Val Cys Phe Asp Ser
    210                 215                 220

Thr Ile Thr Pro Glu Asp Ile Met Val Glu Thr Asp Ile Tyr Ser Ala
225                 230                 235                 240

Ala Lys Leu Ser Asp Gln His Arg Ala Gly Ile His Thr Ile Ala Arg
                245                 250                 255
```

Gln Leu Tyr Ala Gly Gly Pro Met Ile Ala Tyr Asp Gly Arg Glu Ile
                260                 265                 270

Gly Tyr Arg Arg Cys Arg Ser Ser Gly Val Tyr Thr Thr Ser Ser Ser
            275                 280                 285

Asn Ser Leu Thr Cys Trp Leu Lys Val Asn Ala Ala Glu Gln Ala
        290                 295                 300

Gly Met Lys Asn Pro Arg Phe Leu Ile Cys Gly Asp Asp Cys Thr Val
305                 310                 315                 320

Ile Trp Lys Ser Ala Gly Ala Asp Ala Asp Lys Gln Ala Met Arg Val
                325                 330                 335

Phe Ala Ser Trp Met Lys Val Met Gly Ala Pro Gln Asp Cys Val Pro
                340                 345                 350

Gln Pro Lys Tyr Ser Leu Glu Glu Leu Thr Ser Cys Ser Ser Asn Val
            355                 360                 365

Thr Ser Gly Ile Thr Lys Ser Gly Lys Pro Tyr Tyr Phe Leu Thr Arg
        370                 375                 380

Asp Pro Arg Ile Pro Leu Gly Arg Cys Ser Ala Glu Gly Leu Gly Tyr
385                 390                 395                 400

Asn Pro Ser Ala Ala Trp Ile Gly Tyr Leu Ile His Tyr Pro Cys
                405                 410                 415

Leu Trp Val Ser Arg Val Leu Ala Val His Phe Met Glu Gln Met Leu
                420                 425                 430

Phe Glu Asp Lys Leu Pro Glu Thr Val Thr Phe Asp Trp Tyr Gly Lys
            435                 440                 445

Asn Tyr Thr Val Pro Val Glu Asp Leu Pro Ser Ile Ile Ala Gly Val
        450                 455                 460

His Gly Ile Glu Ala Phe Ser Val Val Arg Tyr Thr Asn Ala Glu Ile
465                 470                 475                 480

Leu Arg Val Ser Gln Ser Leu Thr Asp Met Thr Met Pro Pro Leu Arg
                485                 490                 495

Ala Trp Arg Lys Lys Ala Arg Ala Val Leu Ala Ser Ala Lys Arg Arg
                500                 505                 510

Gly Gly Ala His Ala Lys Leu Ala Arg Phe Leu Leu Trp His Ala Thr
            515                 520                 525

Ser Arg Pro Leu Pro Asp Leu Asp Lys Thr Ser Val Ala Arg Tyr Thr
        530                 535                 540

Thr Phe Asn Tyr Cys Asp Val Tyr Ser Pro Glu Gly Asp Val Phe Val
545                 550                 555                 560

Thr Pro Gln Arg Arg Leu Gln Lys Leu Glu His His His His
                565                 570                 575

```
<210> SEQ ID NO 4
<211> LENGTH: 591
<212> TYPE: PRT
<213> ORGANISM: HCV

<400> SEQUENCE: 4
```

Met Gly Ser Ser His His His His His His Ser Ser Gly Leu Val Pro
1               5                   10                  15

Arg Gly Ser His Met Ser Met Ser Tyr Thr Trp Thr Gly Ala Leu Ile
                20                  25                  30

Thr Pro Cys Ala Ala Glu Glu Ser Gln Leu Pro Ile Asn Ala Leu Ser
            35                  40                  45

Asn Ser Leu Val Arg His Arg Asn Met Val Tyr Ser Thr Thr Ser Arg

```
                50                  55                  60
Ser Ala Ala Leu Arg Gln Lys Lys Val Thr Phe Asp Arg Leu Gln Val
 65                  70                  75                  80

Leu Asp Asp His Tyr Arg Asp Val Leu Lys Glu Met Lys Ala Lys Ala
                     85                  90                  95

Ser Thr Val Lys Ala Lys Leu Leu Ser Val Glu Glu Ala Cys Lys Leu
                    100                 105                 110

Thr Pro Pro His Ser Ala Lys Ser Lys Phe Gly Tyr Gly Ala Lys Asp
                    115                 120                 125

Val Arg Asn Leu Ser Ser Lys Ala Val Asp His Ile Arg Ser Val Trp
130                 135                 140

Lys Asp Leu Leu Glu Asp Thr Glu Thr Pro Ile Asp Thr Thr Ile Met
145                 150                 155                 160

Ala Lys Asn Glu Val Phe Cys Val Gln Pro Glu Lys Gly Gly Arg Lys
                    165                 170                 175

Pro Ala Arg Leu Ile Val Phe Pro Asp Leu Gly Val Arg Val Cys Glu
                    180                 185                 190

Lys Met Ala Leu Tyr Asp Val Val Ser Thr Leu Pro Gln Ala Val Met
                    195                 200                 205

Gly Ser Ser Tyr Gly Phe Gln Tyr Ser Pro Lys Gln Arg Val Glu Phe
210                 215                 220

Leu Val Asn Ala Trp Lys Ser Lys Lys Cys Pro Met Gly Phe Ser Tyr
225                 230                 235                 240

Asp Thr Arg Cys Phe Asp Ser Thr Val Thr Glu Ser Asp Ile Arg Val
                    245                 250                 255

Glu Glu Ser Ile Tyr Gln Cys Cys Asp Leu Ala Pro Glu Ala Arg Gln
                    260                 265                 270

Ala Ile Lys Ser Leu Thr Glu Arg Leu Tyr Ile Gly Gly Pro Leu Thr
                    275                 280                 285

Asn Ser Lys Gly Gln Asn Cys Gly Tyr Arg Arg Cys Arg Ala Ser Gly
290                 295                 300

Val Leu Thr Thr Ser Cys Gly Asn Thr Leu Thr Cys Tyr Leu Lys Ala
305                 310                 315                 320

Ser Ala Ala Cys Arg Ala Ala Lys Leu Gln Asp Cys Thr Met Leu Val
                    325                 330                 335

Asn Gly Asp Asp Leu Val Val Ile Cys Glu Ser Ala Gly Thr Gln Glu
                    340                 345                 350

Asp Ala Ala Asn Leu Arg Val Phe Thr Glu Ala Met Thr Arg Tyr Ser
                    355                 360                 365

Ala Pro Pro Gly Asp Leu Pro Gln Pro Glu Tyr Asp Leu Glu Leu Ile
370                 375                 380

Thr Ser Cys Ser Ser Asn Val Ser Val Ala His Asp Ala Ser Gly Lys
385                 390                 395                 400

Arg Val Tyr Tyr Leu Thr Arg Asp Pro Thr Thr Pro Leu Ala Arg Ala
                    405                 410                 415

Ala Trp Glu Thr Ala Arg His Thr Pro Ile Asn Ser Trp Leu Gly Asn
                    420                 425                 430

Ile Ile Met Tyr Ala Pro Thr Leu Trp Ala Arg Met Val Leu Met Thr
                    435                 440                 445

His Phe Phe Ser Ile Leu Leu Ala Gln Glu Gln Leu Glu Lys Ala Leu
                    450                 455                 460

Asp Cys Gln Ile Tyr Gly Ala Cys Tyr Ser Ile Glu Pro Leu Asp Leu
465                 470                 475                 480
```

```
Pro Gln Ile Ile Glu Arg Leu His Gly Leu Ser Ala Phe Ser Leu His
            485                 490                 495

Ser Tyr Ser Pro Gly Glu Ile Asn Arg Val Ala Ser Cys Leu Arg Lys
            500                 505                 510

Leu Gly Val Pro Pro Leu Arg Val Trp Arg His Arg Ala Arg Ser Val
            515                 520                 525

Arg Ala Lys Leu Leu Ser Gln Gly Gly Arg Ala Ala Thr Cys Gly Lys
            530                 535                 540

Tyr Leu Phe Asn Trp Ala Val Arg Thr Lys Leu Lys Leu Thr Pro Ile
545                 550                 555                 560

Pro Ala Ala Ser Arg Leu Asp Leu Ser Gly Trp Phe Val Ala Gly Tyr
                565                 570                 575

Asn Gly Gly Asp Ile Tyr His Ser Leu Ser Arg Ala Arg Pro Arg
            580                 585                 590
```